United States Patent [19]

Skalkos et al.

[11] Patent Number: 5,512,559
[45] Date of Patent: *Apr. 30, 1996

[54] METHOD OF TREATING CANCER TUMORS WITH IMINE PORPHYRIN COMPOUNDS

[75] Inventors: Dimitris Skalkos; Steven H. Selman, both of Toledo; James A. Hampton, Waterville, all of Ohio

[73] Assignee: The University of Toledo and Medical College of Ohio, Toledo, Ohio

[*] Notice: The term of this patent shall not extend beyond the expiration date of Pat. No. 5,424,305.

[21] Appl. No.: 375,629

[22] Filed: Jan. 19, 1995

Related U.S. Application Data

[63] Continuation of Ser. No. 158,020, Nov. 24, 1993, which is a continuation of Ser. No. 901,597, Jun. 19, 1992, abandoned.

[51] Int. Cl.$^6$ .................. A61K 31/40; C07D 487/22
[52] U.S. Cl. .................. 514/185; 540/145; 514/410; 534/11; 534/12
[58] Field of Search .................. 514/185, 410; 540/145

[56] References Cited

U.S. PATENT DOCUMENTS 5,424,305  6/1995  Skalkos et al. .................. 514/185

Primary Examiner—Mukund J. Shah
Assistant Examiner—Pavanaram K. Sripada
Attorney, Agent, or Firm—Marshall & Melhorn

[57] ABSTRACT

Purified imines of porphyrins, chlorins, bateriochlorins, chlorophylls, bacteriochlorophylls, purpurins, reduced purpurins, verdins, Diels Alder adducts, benzochlorins and metal complexes of the foregoing imines are disclosed. The formulas of the benzochlorinimines and of the benzochlorinimine metal complexes are set forth below:

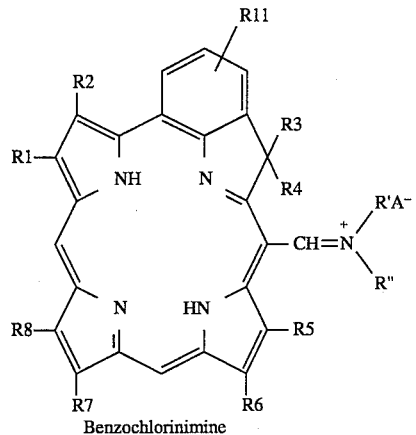

Benzochlorinimine

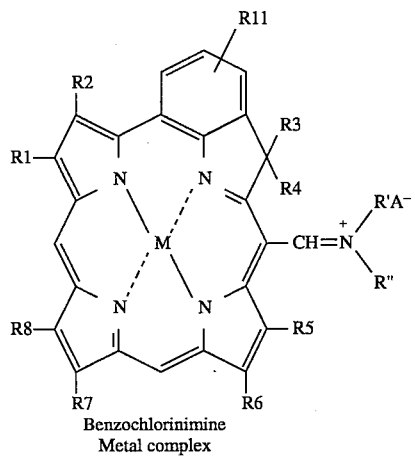

Benzochlorinimine
Metal complex

In specific examples, M in the metal complexes is a copper cation that is complexed with two of the nitrogens of the benzochlorinimine R' and R"" are methyl, and R1 through R8 are ethyl.

12 Claims, No Drawings

METHOD OF TREATING CANCER TUMORS WITH IMINE PORPHYRIN COMPOUNDS

This application is a continuation of application Ser. No. 08/158,020, filed Nov. 24, 1993 which is a continuation of application Ser. No. 07/901,597, filed Jun. 19, 1992 abandoned.

FIELD OF THE INVENTION

This invention relates to the production and use of imines of porphyrins, of porphyrins, and of related compounds, including metal complexes, e.g., benzochlorinimines and benzochlorinimine metal complexes, which are useful in photodynamic therapy. The invention also relates to compositions containing such imines. Specific examples of the benzochlorinimines and of the benzochlorinimine metal complexes of the invention have the following structures:

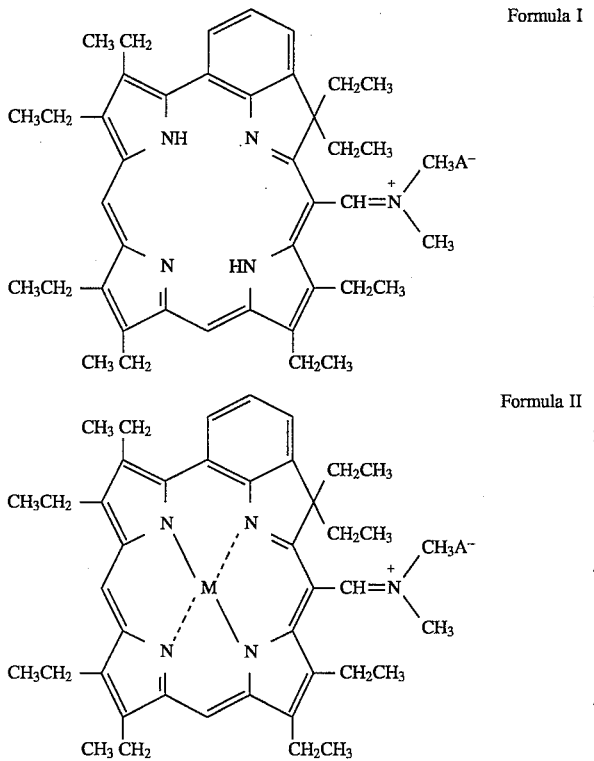

where M comprises a metal cation that is complexed with two of the nitrogens of the benzochlorin and is Ag, Al, Ce, Co, Cr, Cu, Dy, Er, Eu, Fe, Ga, Gd, Hf, Ho, In, La, Lu, Mn, Mo, Nd, Ni, Pb, Pd, Pr, Pt, Rh, Sb, Sc, Sm, Sn, Tb, $^{99m}$Tc, Th, Ti, Tl, Tm, U, V, Y, Yb, Zn or Zr, and A is a physiologically acceptable anion, e.g., chloride.

The benzochlorins, benzochlorin metal complexes, and the other imines and imine metal complexes according to the instant invention are photo sensitizers; i.e., excitation at a suitable wavelength promotes them to the singlet state, from which they decay to the ground state primarily by non-radiative pathways, releasing their energy in several forms, including heat, electron transfer, and probably forming at least one active oxygen species, free radicals, or both. Further, when they are suitably administered, for example, intravenously, to a living patient, they are rejected by healthy tissue, but not by tumors and, as a consequence, they are still present, a suitable time after administration, in tumors of the patient to whom they were administered, but are no longer present in adjacent healthy tissue so that they can be promoted to the singlet state by excitement at a suitable wavelength and will then destroy the tumor as they decay to the ground state. Photothermal sensitizers, which destroy tumors by the release of heat after they have been promoted to the singlet state, are discussed by Jori, G. et al., *Journal of Photochemistry and Photobiology, B: Biology*, 6 (1990), pages 93–101. Sensitizers that, after they have been promoted to the singlet state, produce active oxygen species, probably including singlet oxygen, which then destroys tumors are also known, being disclosed, for example, in "Morgan et al. I", U.S. Pat. No. 4,988,808, Jan. 29, 1991 and in references cited therein.

DISCUSSION OF RELATED ART

Benzochlorin metal complexes and benzochlorins having the formulas of FIGS. 1 and 2, below, are disclosed in Morgan et al. I:

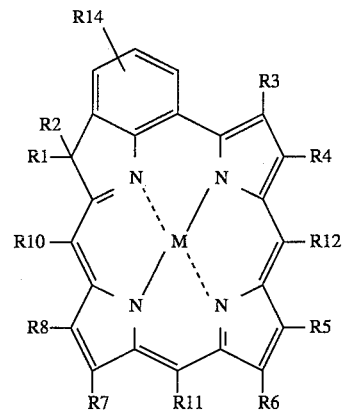

FIG. 1

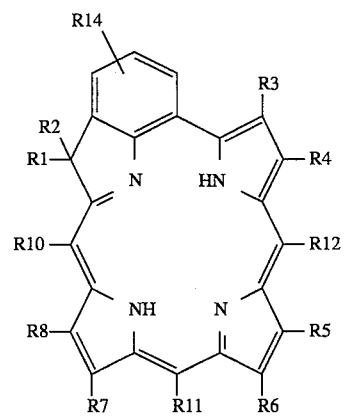

FIG. 2

Compounds having the structures of FIGS. 1 and 2 are also disclosed by Morgan et al., "Photodynamic Action of Benzochlorins", *SPIE* Vol. 1066-Photodynamic Therapy: Mechanisms (1989), pages 146 et seq. and by Vicente et al. "Vilsmeier Reactions of Porphyrins and Chlorins with 3-(Dimethylamimo)acrolein To Give meso-(2-Formylvinyl)porphyrins: * * * " *J. Org. Chem.* 1991, 56, pages 4407–4418 (see, also, Arnold, D. P. et al., *Journal of The Chemical Society, Perkin Transactions I* (1979), pages 1660 et seq.). The specific benzochlorins disclosed by Morgan et al. are compounds where each of R1 through R8 is ethyl, each of R10 through R12 is hydrogen, and (a) the compound has the structure of FIG. 1, R14 is SO$_3$Na and M is Sn;

(b) the compound has the structure of FIG. 2 and R14 is H;

3

(c) the compound has the structure of FIG. 2 and R14 is SO$_3$Na; and (d) the compound has the structure of FIG. 1, R14 is H, and M is Sn.

Similarly, porphyrins, chlorins, bacteriochlorins, chlorophylls, bacteriochlorophylls, purpurins, reduced purpurins, verdins, Diels-Alder Adducts, isobacteriochlorins, and metal complexes of the foregoing are all known, as is the use of the Vilsmeier reagent to introduce formyl groups into porphyrins; the reaction of the Vilsmeier reagent (dimethylformamide, for example, and phosphoryl chloride) produces imines as intermediates. So far as is known, however, the imines produced by the Vilsmeier reagent have not previously been separated from the reaction mixture; instead, the reaction has been allowed to proceed until the formyl group was formed.

BRIEF DESCRIPTION OF THE PRESENT INVENTION

The present invention is a family of imines, e.g., benzochlorinimines having the structure set forth below and identified by legend, and a family of imine metal complexes, e.g., benzochlorinimine metal complexes having the structure set forth below and identified by legend, and a method for treating tumors which involves the administration of one of the imines, e.g., a benzochlorinimine having the structure set forth below, or one of the imine metal complexes, e.g., a benzochlorinimine metal complex having the structure set forth below, to a human or animal patient with a tumor, and, after a suitable period of time, irradiation of the tumor with light of a suitable wavelength and of sufficient intensity to promote the imine or imine metal complex to the singlet state.

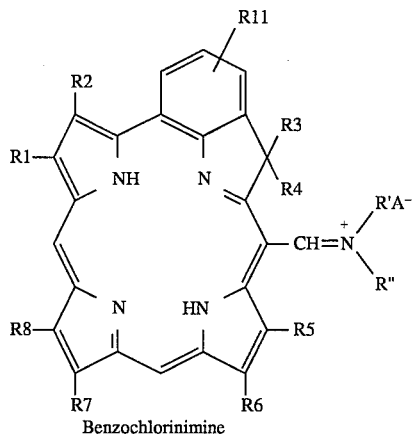
Benzochlorinimine

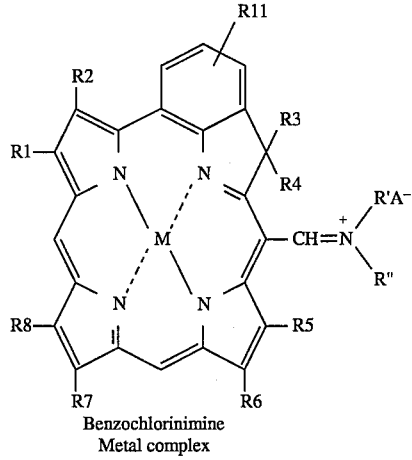
Benzochlorinimine Metal complex

In the benzochlorinimines and benzochlorinimine metal complexes having the foregoing formulas:

M and A have the meanings indicated above, R' and R" can be the same or different and each is hydrogen, an alkyl group having from 1 to 4 carbon atoms, or the two, together, can consist of two CH$_2$ groups each of which is bonded to the nitrogen atom, and the two of which are a part of an aliphatic hydrocarbon chain having from 4 to 6 carbon atoms, and each of R1 through R8 and R11 is H or CHO, an alkyl group other than t-butyl having from 1 to 4 carbon atoms, an alkylene group having from 2 to 4 carbon atoms, a group having the formula R$_3$N(R$_4$)$_2$ where R$_3$ is a bivalent aliphatic hydrocarbon radical having from 1 to 4 carbon atoms, wherein any carbon to carbon bond is either a single or a double bond, and not more than one is a double bond; R$_4$ is hydrogen or an alkyl radical having from 1 to 2 carbon atoms and the two R$_4$ groups can be the same or different, a group having the formula R$_3$N(R$_5$)$_3$ A where R$_3$ is a bivalent aliphatic hydrocarbon radical having from 1 to 4 carbon atoms, wherein any carbon to carbon bond is either a single or a double bond, and not more than one is a double bond; A is a physiologically acceptable anion and R$_5$ is an alkyl group having from 1 to 2 carbon atoms and the three R$_5$ groups can be the same or different, a group having the formula R$_3$OH where R$_3$ is a bivalent aliphatic hydrocarbon radical having from 1 to 4 carbon atoms, wherein any carbon to carbon bond is either a single or a double bond, and not more than one is a double bond, or CO$_2$R', CH$_2$CO$_2$R' or CH$_2$CH$_2$CO$_2$R', where R' is H, or an alkyl group other than t-butyl having from one to four carbon atoms, with the proviso that R11 can be SO$_3$H or a salt thereof.

Other imines and imine metal complexes of the families of the instant invention have the formulas set forth below, and identified by legend.

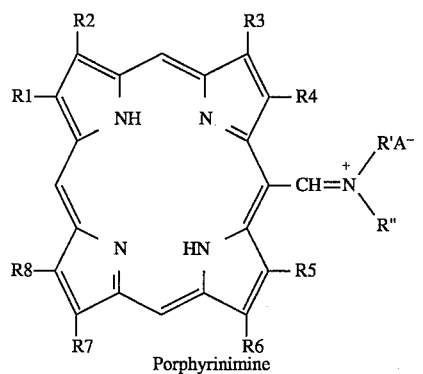
Porphyrinimine
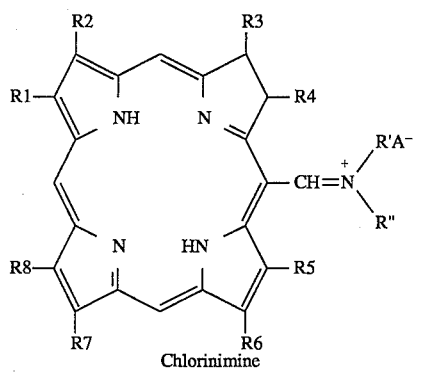
Chlorinimine
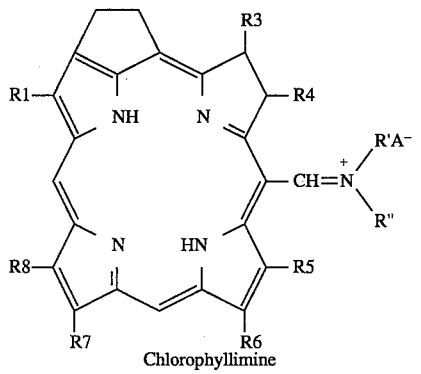
Chlorophyllimine
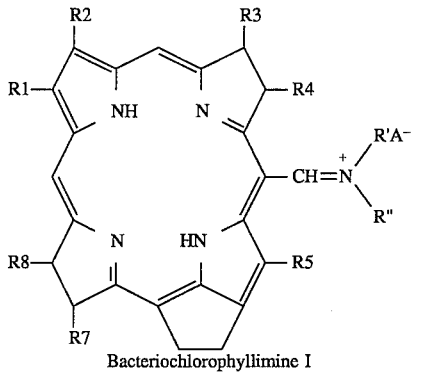
Bacteriochlorophyllimine I
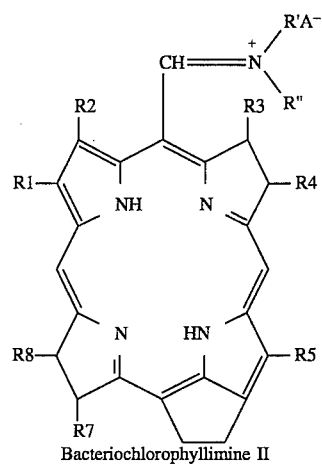
Bacteriochlorophyllimine II
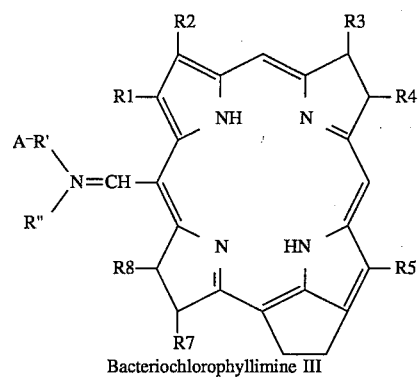
Bacteriochlorophyllimine III
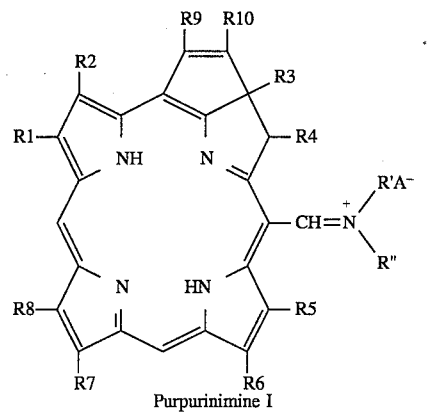
Purpurinimine I

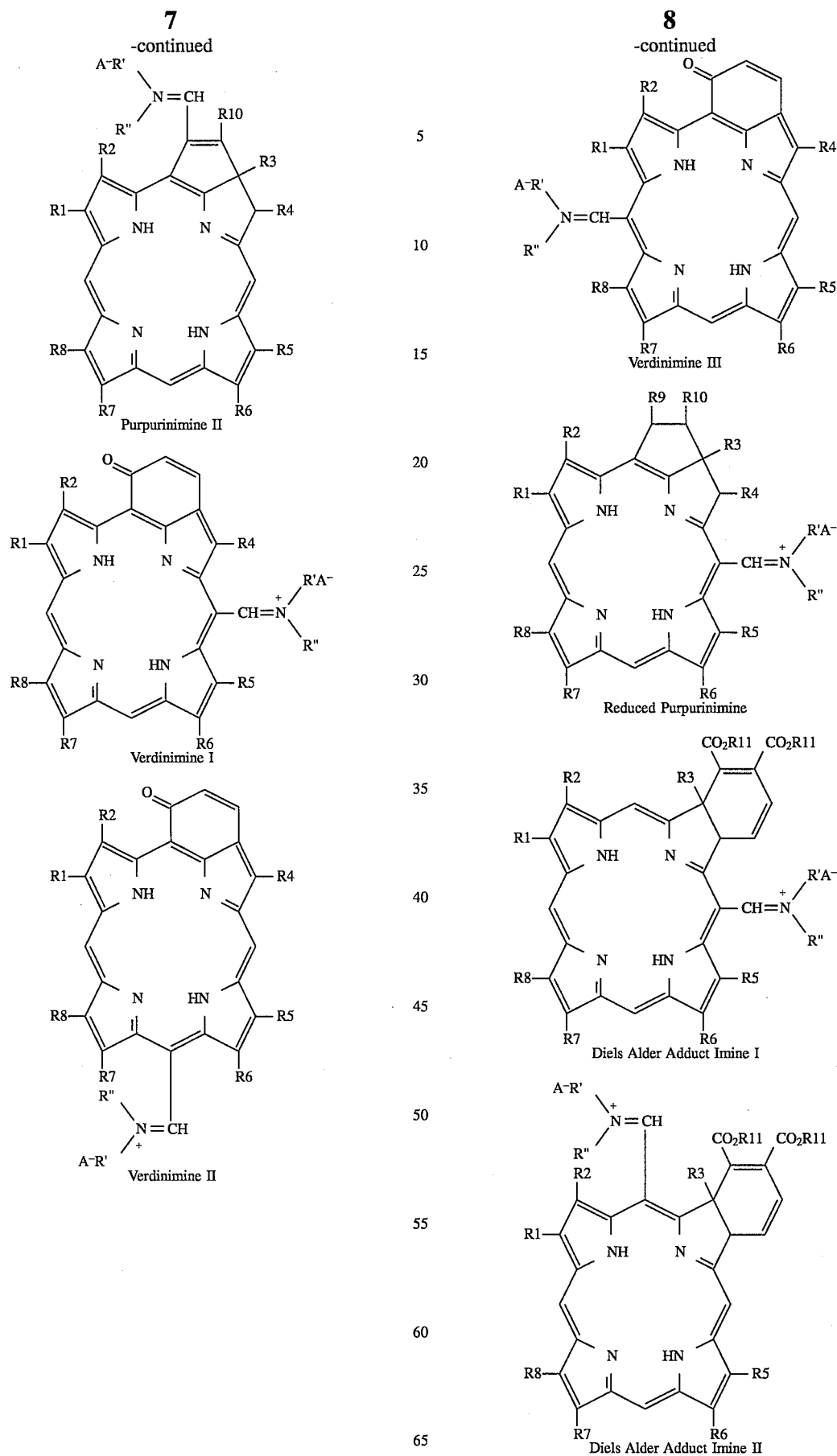

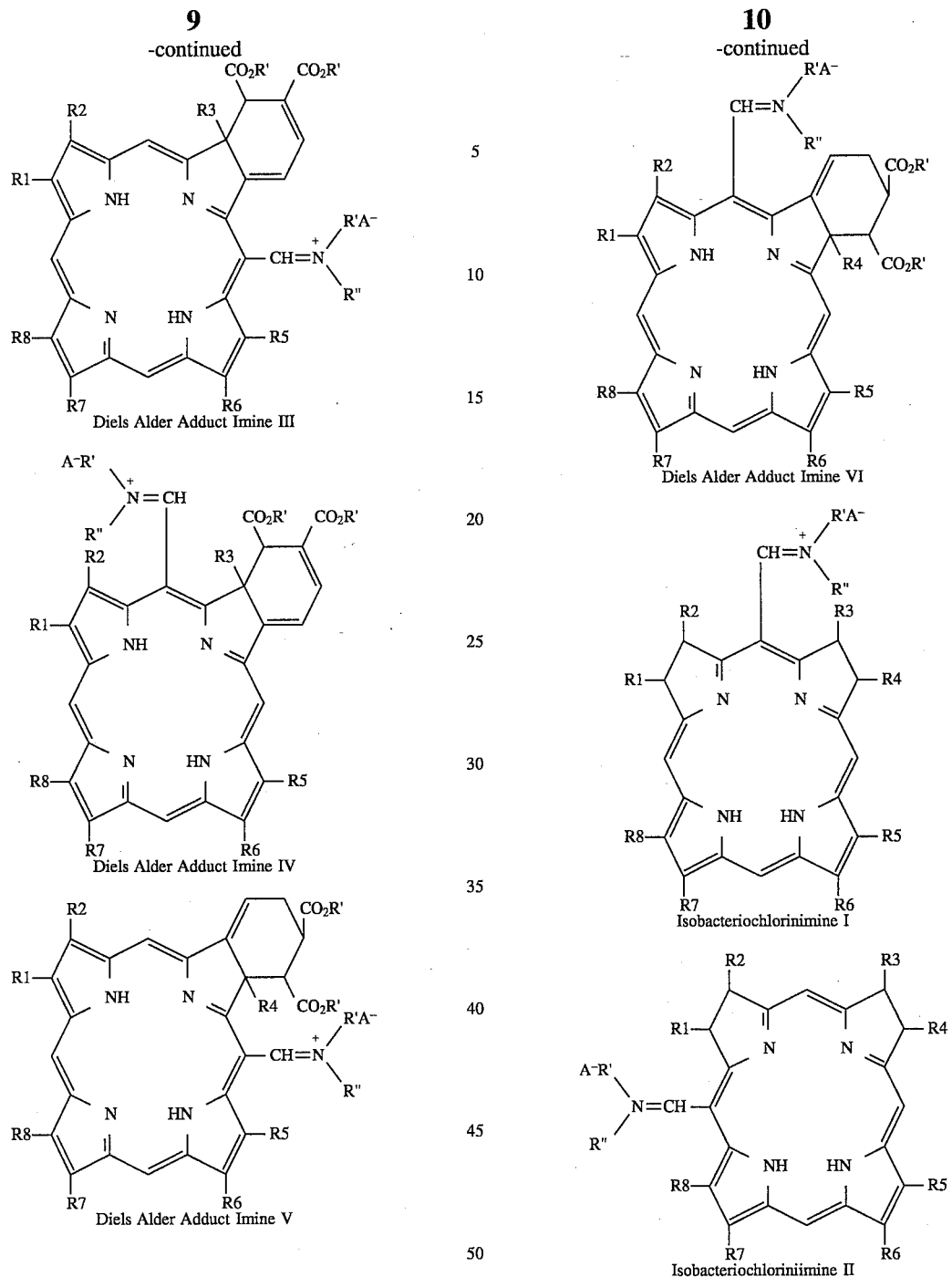

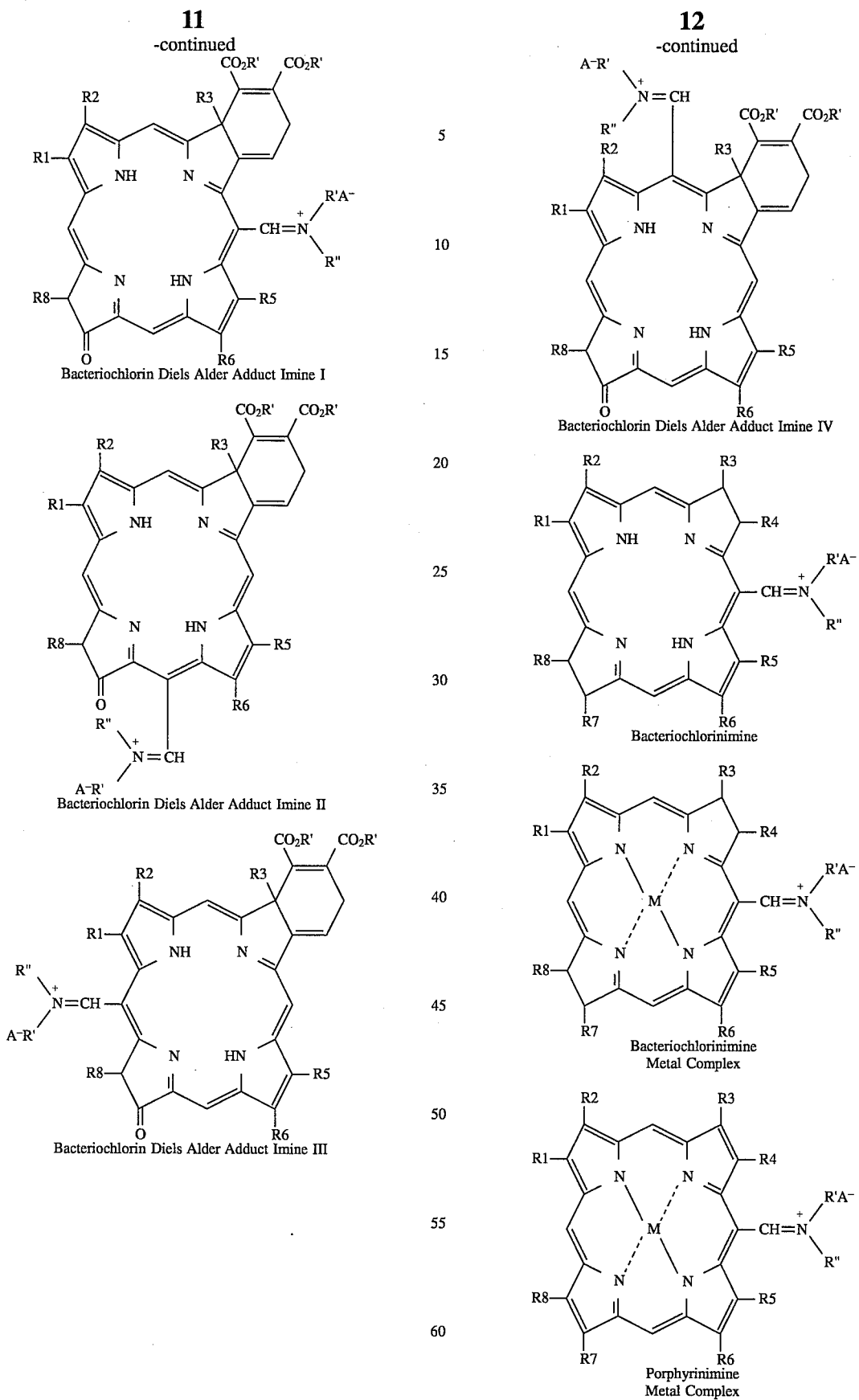

13
-continued
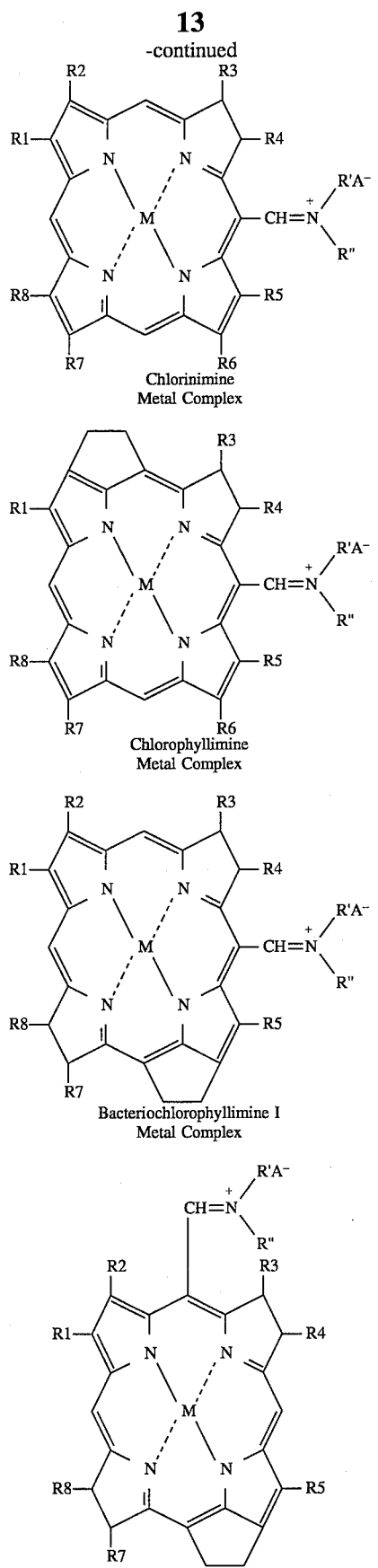
Chlorinimine
Metal Complex
Chlorophyllimine
Metal Complex
Bacteriochlorophyllimine I
Metal Complex
14
-continued
Bacteriochlorophyllimine II
Metal Complex
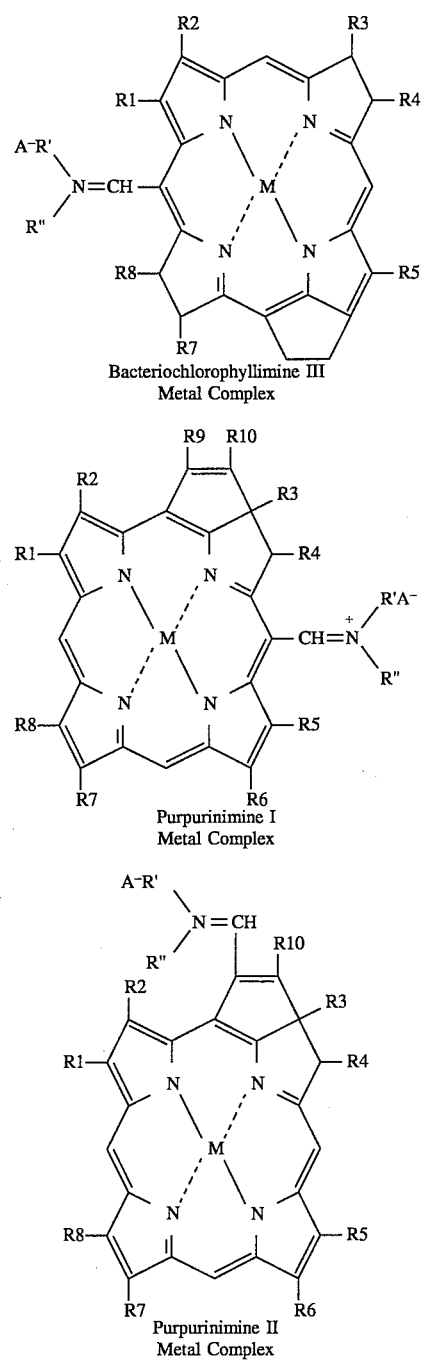
Bacteriochlorophyllimine III
Metal Complex
Purpurinimine I
Metal Complex
Purpurinimine II
Metal Complex 15
-continued
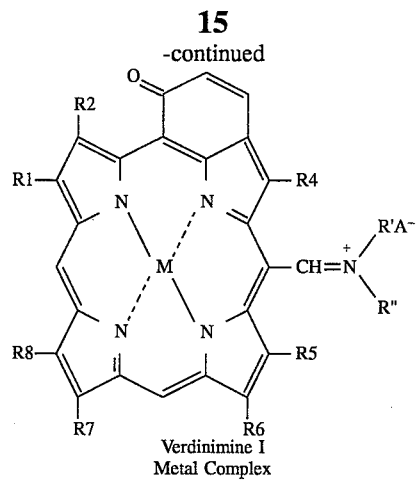
Verdinimine I
Metal Complex
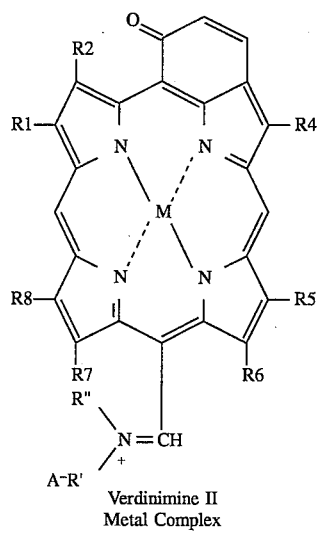
Verdinimine II
Metal Complex
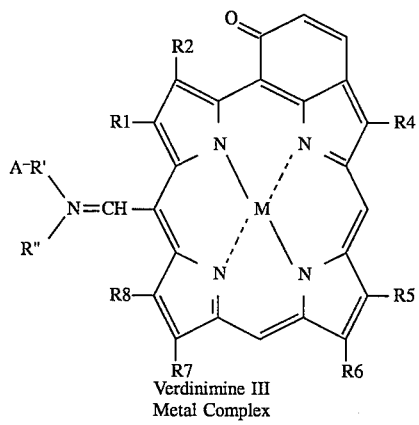
Verdinimine III
Metal Complex
16
-continued
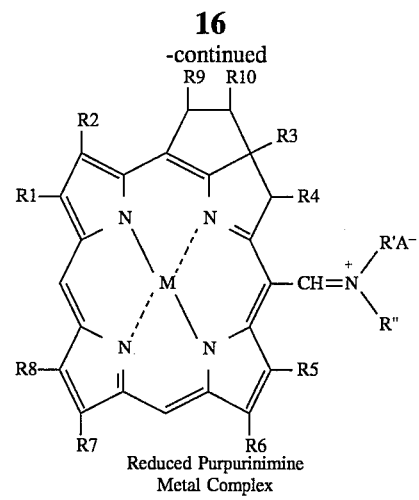
Reduced Purpurinimine
Metal Complex
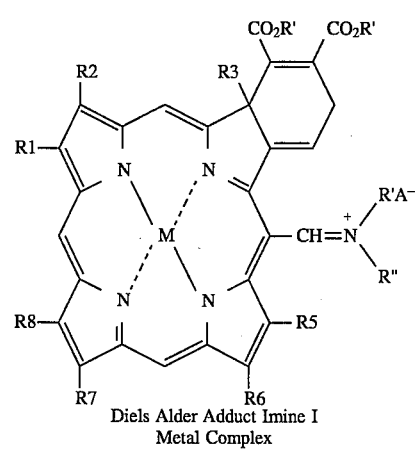
Diels Alder Adduct Imine I
Metal Complex
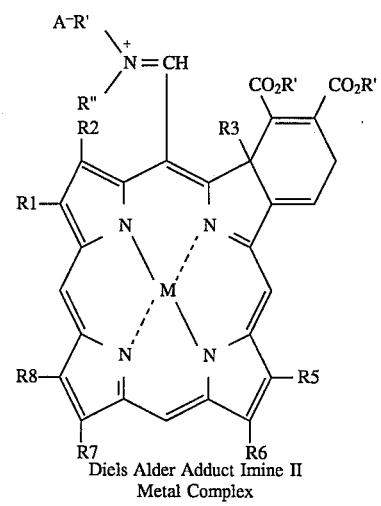
Diels Alder Adduct Imine II
Metal Complex

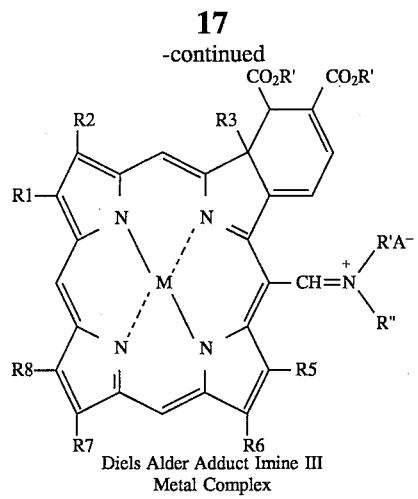
Diels Alder Adduct Imine III
Metal Complex
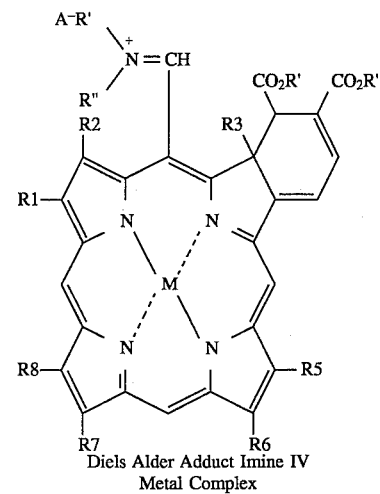
Diels Alder Adduct Imine IV
Metal Complex
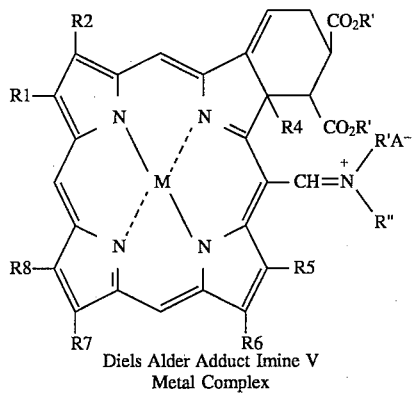
Diels Alder Adduct Imine V
Metal Complex
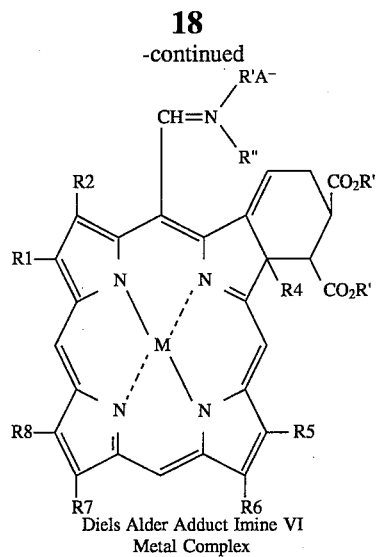
Diels Alder Adduct Imine VI
Metal Complex
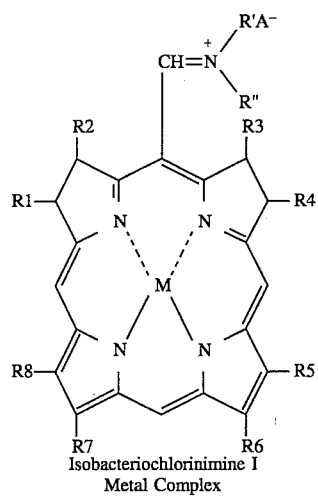
Isobacteriochlorinimine I
Metal Complex
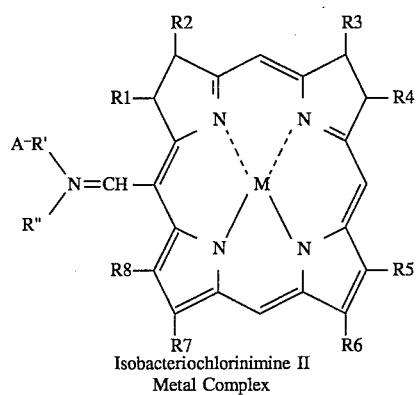
Isobacteriochlorinimine II
Metal Complex

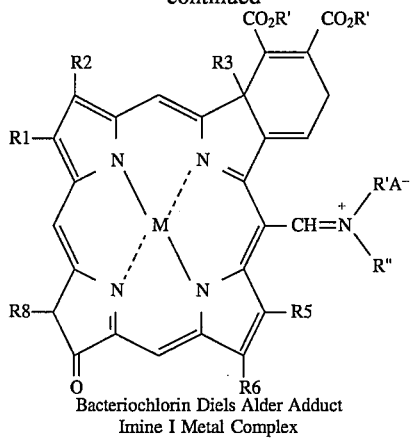

Bacteriochlorin Diels Alder Adduct
Imine I Metal Complex

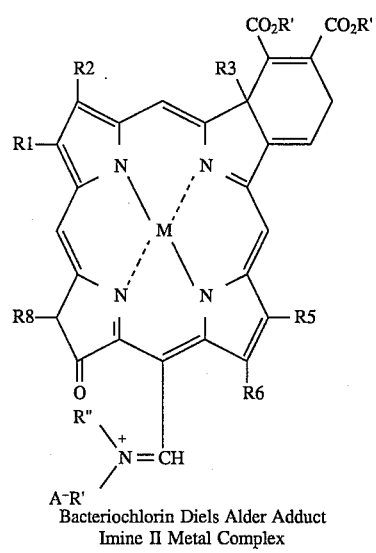

Bacteriochlorin Diels Alder Adduct
Imine II Metal Complex

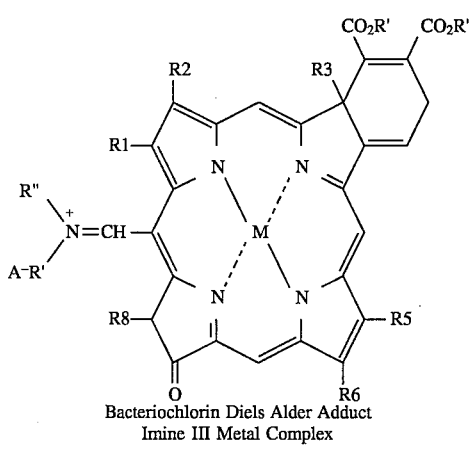

Bacteriochlorin Diels Alder Adduct
Imine III Metal Complex

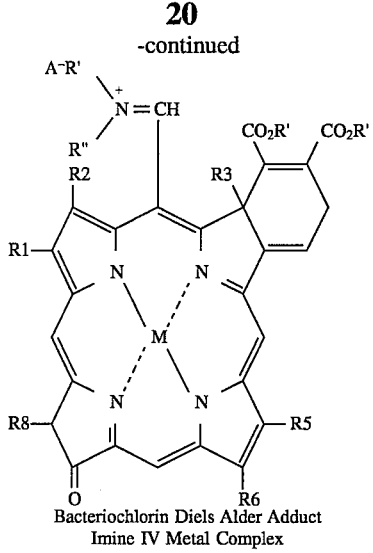

Bacteriochlorin Diels Alder Adduct
Imine IV Metal Complex

In the foregoing formulas, M comprises a metal cation that is complexed with two of the nitrogens of the benzochlorin and is Ag, Al, Ce, Co, Cr, Cu, Dy, Er, Eu, Fe, Ga, Gd, Hf, Ho, In, La, Lu, Mn, Mo, Nd, Ni, Pb, Pd, Pr, Pt, Rh, Sb, Sc, Sm, Sn, Tb, $^{99m}$Tc, Th, Ti, Tl, Tm, U, V, Y, Yb, Zn or Zr, A is a physiologically acceptable anion, e.g., chloride, R' and R" can be the same or different and each is hydrogen, an alkyl group having from 1 to 4 carbon atoms, or the two, together, can consist of two $CH_2$ groups each of which is bonded to the nitrogen atom, and the two of which are a part of an aliphatic hydrocarbon chain having from 4 to 6 carbon atoms, and each of R1 through R11 is H or CHO, an alkyl group other than 1-butyl having from 1 to 4 carbon atoms, an alkylene group having from 2 to 4 carbon atoms, a group having the formula $R_3N(R_4)_2$ where $R_3$ is a bivalent aliphatic hydrocarbon radical having from 1 to 4 carbon atoms, wherein any carbon to carbon bond is either a single or a double bond, and not more than one is a double bond; $R_4$ is hydrogen or an alkyl radical having from 1 to 2 carbon atoms and the two $R_4$ groups can be the same or different, a group having the formula $R_3N(R_5)_3$ A where $R_3$ is a bivalent aliphatic hydrocarbon radical having from 1 to 4 carbon atoms, wherein any carbon to carbon bond is either a single or a double bond, and not more than one is a double bond; A is a physiologically acceptable anion and $R_5$ is an alkyl group having from 1 to 2 carbon atoms and the three $R_5$ groups can be the same or different, a group having the formula $R_3OH$ where $R_3$ is a bivalent aliphatic hydrocarbon radical having from 1 to 4 carbon atoms, wherein any carbon to carbon bond is either a single or a double bond, and not more than one is a double bond, or $CO_2R'$, $CH_2CO_2R'$ or $CH_2CH_2CO_2R'$ where R' is H, or an alkyl group other than t-butyl having from one to four carbon atoms, with the proviso that R11 can be $SO_3H$ or a salt thereof.

In the foregoing Chlorinimines and metal complexes, either R3 or R4 can be a $CH_2$ group or O which, in either case, is bonded to the carbon of the pyrrole ring by a double bond. Likewise, in the foregoing families of compounds which are designated Isobacteriochlorinimine I and Isobacteriochlorinimine II either R1 or R2 can be a $CH_2$ group or O which, in either case, is bonded to the carbon of the pyrrole ring by a double bond and, when either R1 or R2 is a $CH_2$ group or O, either R3 or R4 is also a $CH_2$ group or O which is bonded to the carbon of the pyrrole ring by a double bond. Finally, in the foregoing families of compounds which are designated bacteriochlorinimine either R3 or R4 can be a $CH_2$ group or O which, in either case, is bonded to the carbon of the pyrrole ring by a double bond and, when either R3 or R4 is a $CH_2$ group or O, either R7 or R8 is also a $CH_2$ group or O which is bonded to the carbon of the pyrrole ring by a double bond.

DESCRIPTION OF THE PREFERRED EMBODIMENTS

The following examples constitute the best modes presently contemplated by the inventors, but are presented solely to illustrate and disclose the invention, and are not intended to be limiting.

As used herein, and in the appended claims, the terms "percent" and "parts" refer to percent and parts by weight, unless otherwise indicated; g means gram or grams; mg means milligram or milligrams; ng means nanogram or nanograms; pg means picogram or picograms; cm means centimeter or centimeters; mm means millimeter or millimeters; L means liter or liters; mL means milliliter or milliliters; μL means microliter or microliters; $^v/_v$ means percent by volume; $^m/_o$ means mole percent, and equals 100 times the number of moles of the constituent designated in a composition divided by the total number of moles in the composition; $^v/_v$ means percent by volume; $^w/_v$ means weight per unit of volume, and is in terms of g/L; M means molar and equals the number of gram moles of a solute in one liter of a solution; μM means micromolar and equals the number of microgram moles in one liter of a solution; mM means millimolar and equals the number of milligram moles of a solute in one liter of a solution; N means normal, and equals the number of gram equivalents of a solute in one liter of solution; μN means micronormal and equals the number of microgram equivalents of a solute in one liter of solution; and mW means milliwatt or milliwatts. All temperatures are in °C., unless otherwise indicated.

Example 1 describes the production of "Cu Benzochlorinimine I" (Formula II, supra, where M is Cu and A is $Cl^-$). In Example 1, Cu Benzochlorinimine I is produced from a solution of 30 dichloroethane of 1 mL Vilsmeier reagent and 80 mg "Cu Octaethyl Benzochlorin" (Vicente et al., supra):

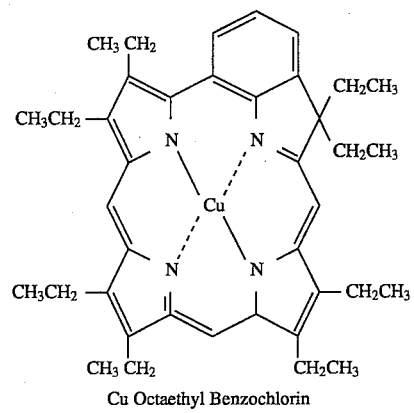

Cu Octaethyl Benzochlorin

EXAMPLE 1

The Vilsmeier reagent was produced by mixing 0.5 mL phosphoryl chloride with 0.5 mL dimethyl formamide, and was then added to a solution of the Cu Octaethyl Benzochlorin in the dichloroethane, which solution had been heated to a temperature in the range of 60° to 65°. The reaction mixture was stirred for 15 minutes at a temperature within the temperature indicated range, and was then washed with deionized water. After removal of the solvent under reduced pressure, the crude product which remained was purified by recrystallization from dichloromethane/hexane. The yield was 80 mg Cu Benzochlorinimine I (87 percent of theory). The Cu Benzochlorinimine I was identified by high resolution mass spectrometry; in dichloromethane solvent it has absorbance peaks in the visible spectrum at wavelengths of 386, 448, 570, 690 and 752 nm (51000, 30000, 7000, 12000, 35000).

The procedure of Example 1 has been repeated, except that equivalent amounts of other formamides were substituted for the dimethylformamide to produce other copper octaethyl benzochlorinimines. The formamides used had the formulas given in the following table, and produced benzochlorinimine metal complexes which had the structure previously identified by legend where R1 through R8 were ethyl, R11 was hydrogen, $A^-$ was chloride, M was copper, and the imine group had the structure given in the table:

| Number assigned to Cu Benzochlorinimine | Formula of formamide used | Formula for imine group of benzochlorinimime metal complex |
|---|---|---|
| II | $\underset{\text{HC}-\text{N}(-\text{CH}_2\text{CH}_3)_2}{\overset{\text{O}}{\|}}$ | $\underset{-\text{CH}-\text{N}(-\text{CH}_2\text{CH}_3)_2}{\overset{\text{O}}{\|}}$ |
| III | $\underset{\text{HC}-\text{N}(-\text{CH}[\text{CH}_3]_2)_2}{\overset{\text{O}}{\|}}$ | $\underset{-\text{CH}=\text{N}(-\text{CH}_2\text{CH}_2\text{CH}_2\text{CH}_3)_2}{\overset{\text{O}}{\|}}$ |

-continued

| Number assigned to Cu Benzochlorinimine | Formula of formamide used | Formula for imine group of benzochlorinimime metal complex |
|---|---|---|
| IV | $\text{HC}-\text{N}(-\text{CH}_2\text{CH}_2\text{CH}_2\text{CH}_3)_2$ with $=\text{O}$ | $-\text{CH}=\text{N}(-\text{CH}_2\text{CH}_2\text{CH}_2\text{CH}_3)_2$ with $=\text{O}$ |
| V | $\text{HC}-\text{N}$ (pyrrolidine ring) with $=\text{O}$ | $-\text{CH}=\text{N}$ (pyrrolidine ring) with $=\text{O}$ |

In vitro and in vivo testing of Cu Benzochlorinimine I was also carried out by established procedures. The cells used for the in vitro testing were AY-27FANFT transitional cell bladder cancer cells attached to 28 cm² culture dishes. Cu Benzochlorinimine I was added to the culture dishes at four concentrations: 0.1, 0.25, 0.5 and 1 μg per mL, and "Cremophor E" (defined below) was added as a control at 1 μg per mL. Four hours after the Cu Benzochlorin I and "Cremophor E" additions, the cells were washed, irradiated, in one series of tests with a pulsed beam (750 nm) from an Alexandrite laser and, in another series of tests, with a continuous beam (590 nm) from a xenon arc lamp. The irradiated cells were then incubated for 4 to 7 days until colony formation occurred. Surviving colonies were then counted, and mean values for surviving colonies were determined. The results, when the Alexandrite laser was used, in terms of the mean numbers of surviving colonies as a function of the fluence of radiation in Joules per cm², are summarized in the following table.

| Imine Concentration | Fluence | surviving colonies, mean |
|---|---|---|
| 1.0 | 0 | 550 |
| 0.5 | 0 | 772 |
| 0.25 | 0 | 850 |
| 0.1 | 0 | 898 |
| Control | 0 | 919 |
| 1.0 | 1.05 | 110 |
| 0.5 | 1.05 | 597 |
| 0.25 | 1.05 | 843 |
| 0.1 | 1.05 | 816 |
| Control | 1.05 | 832 |
| 1.0 | 2.1 | 18 |
| 0.5 | 2.1 | 207 |
| 0.25 | 2.1 | 756 |
| 0.1 | 2.1 | 701 |
| Control | 2.1 | 823 |
| 0.5 | 6.3 | 7 |
| 0.25 | 6.3 | 51 |
| 0.1 | 6.3 | 485 |
| Control | 6.3 | 846 |
| 0.25 | 10.5 | 2 |
| 0.1 | 10.5 | 83 |
| Control | 10.5 | 850 |

To conduct the foregoing tests, the Cu Benzochlorinimine I was dissolved in a commercially available non-ionic solubilizer and emulsifier obtained by reacting ethylene oxide with castor oil in a ratio of 35 moles of ethylene oxide per mole of castor oil, diluting the resulting solution with 1,2-propanediol, and producing an emulsion with the resulting solution and 0.9 percent aqueous sodium chloride solution. The specific non-ionic solubilizer used is available from BASF under the designation CREMOPHOR EL; it is composed of fatty acid esters of polyglycols, glycerol polyglycols, polyethylene glycols and ethoxylated glycerol. The test solutions were prepared from 50 mg Cu Benzochlorinimine I, about 1 mL warm solubilizer (enough to dissolve the test compound), and enough 1,2-propanediol to make a solution of the Cu Benzochlorinimine I in a mixed diol/solubilizer solvent containing 32.9 percent solubilizer; finally, enough 0.9 percent aqueous sodium chloride was added to make 10 mL test solution so that the final concentration of the Cu Benzochlorinimine I in the test solution was 5 mg per mL. Each test solution was made, with mechanical shaking and stirring, by dissolving the Cu Benzochlorinimine I in the solubilizer, diluting the resulting solution with the indicated amount of 1,2-propanediol, and adding the sodium chloride solution to the diluted solution. A control solution was also prepared for use with each test solution. The control was identical with the test solution except that it contained no Cu Benzochlorinimine I.

The results of the in vitro testing, when the Xenon arc lamp was used, in terms of the mean numbers of surviving colonies as a function of the fluence of radiation in Joules per cm², are summarized in the following table.

| Imine Concentration | Fluence | surviving colonies, mean |
|---|---|---|
| 1.0 | 0 | 115 |
| 0.5 | 0 | 841 |
| 0.25 | 0 | 942 |
| 0.1 | 0 | 905 |
| Control | 0 | 928 |
| 0.5 | 1.05 | 193 |
| 0.25 | 1.05 | 689 |
| 0.1 | 1.05 | 731 |
| Control | 1.05 | 836 |
| 0.5 | 2.1 | 28 |
| 0.25 | 1.1 | 317 |
| 0.1 | 2.1 | 703 |
| Control | 2.1 | 795 |
| 0.25 | 6.3 | 5 |
| 0.1 | 6.3 | 51 |
| Control | 6.3 | 907 |
| 0.1 | 10.5 | 2 |
| Control | 10.5 | 841 |

The in vivo testing was conducted on male Fisher 344 rats weighing 135 to 150 g in whom the transplantable FANFT (N-[4-(5-nitro-2-furyl)-2-thiazolyl]formamide tumor system had been implanted. (Use of this system is reported by Selman, S. H., et al., Cancer Research, pp. 1924–1927, May, 1984.) Two tumors were implanted into the subcutaneous tissue of the flank of each test animal; when the testing was carried out, each tumor was about 1 cm in diameter.

The Cu Benzochlorinimine I was dissolved in the previously identified non-ionic solubilizer that is commercially available under the designation CREMOPHOR EL, and test solutions which contained 2 mg per mL Cu Benzochlorinimine I were prepared as previously described.

The testing involved injecting each rat with a solution of the Cu Benzochlorinimine I, dosage 3.5 mg per kg of body weight or 7 mg per kg of body weight or with the same volume of the appropriate control, irradiating one of the two tumors with laser light, in some cases, observing the animals over a period of time and, in others, sacrificing the animals, and examining the tumors. The injections were made via the dorsal tail vein. The irradiation of one of the tumors occurred twenty four hours after each rat was injected while the other of the two tumors was shielded.

Tumor temperature and body core temperature were monitored, using thermistors, one placed percutaneously beneath the tumor and one placed intrarectally. Tumor temperature was kept within 2° of body core temperature by directing a jet of cool air over the tumor.

Both the Alexandrite laser and the Xenon arc lamp were used to irradiate the tumors. The light intensity on the tumor was monitored; each tumor received 200 mW per $cm^2$ (360 Joules per $cm^2$).

Twenty four hours after the irradiation, some of the rats that had been injected with the test solution and one of the rats that had been injected with the control were sacrificed by an intracardiac injection of saturated aqueous potassium chloride solution. Others of the rats that had been injected with the test solution and with the control solution were observed over a period of time. During the testing, the rats were under barbituate anesthesia (65 mg per kg body weight).

The tumors from the sacrificed rats were excised, placed in 10 percent phosphate-buffered formalin and cut into three sections perpendicular to their long axis. The tumors were then embedded in paraffin and cut into sections five microns in width. The sections were stained with hematoxylin and eosin.

Histologic examination of the stained sections (twenty four hours after a tumor was irradiated by either light source) revealed extensive necrosis of cancer cells in tumors of rats that had been injected with Cu Benzochlorinimine, and no necrosis of tumor cells in rats that had been injected with Cremophor. The examination revealed no necrosis of cells of tumors that were not irradiated. Fourteen days after irradiation, the irradiated tumors of three of the six rats that were not sacrificed and had been injected with 7 mg Cu Benzochlorinimine per kg of body weight showed no sign of tumor regrowth.

SKH1 hairless mice (five animals) were injected with Cu Benzochlorinimine (7 mg per kg of body weight), and the five animals were subjected to light treatment one day after the injection. One of the animals showed slight skin burn, while the other animals showed no skin damage. This indication is important, because extensive and prolonged skin damage is a common side effect of other sensitizers.

The production of Cu Benzochlorinimine I by reaction between Cu Octaethyl Benzochlorin and a Vilsmeier reagent produced from phosphoryl chloride and dimethyl formamide is described in Example 1. The structure of Cu Octaethyl Benzochlorin is given above; its structure is also that of FIG. 1, above, where R1 through R8 are ethyl, R10 through R12 and R14 are hydrogen, and M is Cu; the reaction introduced a substituent having the formula —CH=$N^+(CH_3)_2$. This was an R10 substituent in the FIG. 1 formula for Cu Octaethyl Benzochlorin. As has been stated above, other R10 substituents have been introduced, using the Example 1 procedure to react Cu Octaethyl Benzochlorin with Vilsmeier reagents from phosphoryl chloride and formamides other than dimethyl formamide, e.g., diethyl formamide, diisopropyl formamide, di n-butyl formamide, cyclic formamides, and the like. In general, by using different formamides, benzochlorins can be produced which have the Formula II structure except that one of the $CH_3$ groups of the R10 substituent is replaced by an alkyl group having from 2 to 4 carbon atoms or where both of the $CH_3$ groups are so replaced; the two alkyl groups can be the same or different. Imines where R' is hydrogen, R" is hydrogen, or both R' and R" are hydrogen can also be prepared by conducting the reaction between Cu Octaethyl Benzochlorin or the like and the Vilsmeier reagent to introduce a formyl group into the molecule (see the second paragraph of Example A, infra) and then reacting the formyl group with ammonia, a primary alkyl amine, or a secondary alkyl amine, to produce, respectively, an imine where R' and R" are both hydrogen, an imine where one of R' and R" is hydrogen and the other is an alkyl group, and an imine where both R' and R" are alkyl groups. In any case, the alkyl group has from one to four carbons. As disclosed above, imines including cyclic structures can also be produced, e.g., where R' and R" are both $CH_2$, each of which is bonded to the nitrogen atom, and the two of which are a part of an aliphatic hydrocarbon chain having from 4 to 6 carbon atoms.

Similarly, the procedure of Example 1 can be used to introduce —CH=$N^+(CH_3)_2$ and other imine substituents into copper complexes of benzochlorins other than Cu Benzochlorin I, and, generally, into benzochlorin metal complexes having the structure of FIG. 1, supra where R1 through R8 and M have the meanings set forth above, R10 through R12 are hydrogen, and R14 can have the same meaning as R1 through R8, and can also be $SO_3H$ or a salt thereof. For example, the Cu or the Ni complex of octaethylbenzochlorin, compounds which have the structure of FIG. 1, supra, where R1 through R8 are ethyl, R10, R11, R12 and R14 are hydrogen, and M is copper or nickel, can be produced from octaethylporphyrin by the procedure of Example A, below, and can be reacted by the procedure of Example 1 to produce a benzochlorinimine according to the invention having the structure set forth above where R1 through R8 are ethyl, R11 is hydrogen, A is $Cl^-$, and M is Cu or Ni. The identities of R' and R" depend upon the identity of the formamide used. Six intermediates were produced in the procedure of Example A, [I] nickel octaethylporphyrin [II], nickel meso-formyloctaethylporphyrin, [III] Nickel meso-(β-ethoxy-carbonylvinyl)-octaethylporphyrin [IV], meso-(β-ethoxy carbonylvinyl)-octaethylporphyrin, and [V]meso-(β-hydroxyvinyl)-octaethylporphyrin, and [VI] octaethylbenzochlorin, in addition to [VII] Nickel or Copper octaethylbenzochlorin, from the octaethylporphyrin, which has the structure of FIG. 3, below, where, R1 through R8 are ethyl, and R is hydrogen. FIG. 3 is a general formula for porphyrins. The nickel octaethylporphyrin, the nickel meso-formyloctaethylporphyrin, the Nickel meso-(β-ethoxy-carbonylvinyl)-octaethylporphyrin, and the meso-(β-hydroxymethylvinyl)- octaethylporphyrin, all had the structure of FIG. 4, below, where R1 through R8 were ethyl. In the nickel octaethylporphyrin R was H; in the meso-formyloctaethylporphyrin R was CHO; in the nickel meso-(β-ethoxy-carbonylvinyl)-octaethylporphrin R was CH=$CHCO_2CH_2CH_3$; in the meso-(β-hydroxy-methylvinyl)-octaethylporphyrin R was CH=$CHCH_2OH$. FIG. 4 is a general structure for nickel complexes of porphyrins.

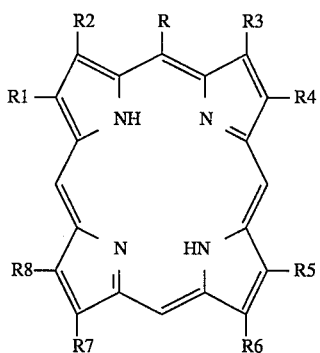

FIG. 3

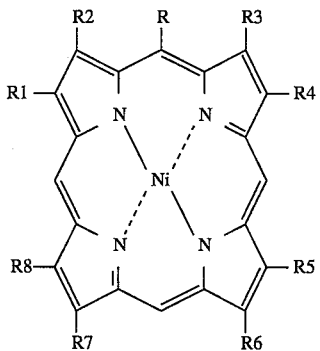

FIG. 4

The nickel octaethylporphyrin is first produced from 100 mg nickel acetate and a solution of 20 mg octaethylporphyrin in a mixed solvent composed of 15 mL dichloromethane and 5 mL methanol.

Example A

Production of Nickel octaethylporphyrin

The nickel acetate is added to the octaethylporphyrin solution; the mixture which results is refluxed for about 24 hours until the electronic spectrum of the reaction mixture indicates that chelation is complete. The reaction mixture is then concentrated to 7 mL and allowed to cool to room temperature of about 22°. Product which precipitates is recovered by filtration, dissolved in a mixed solvent composed of 5 mL dichloromethane and 2 mL methanol, and recrystallized, yielding Ni octaethylporphyrin.

Production of nickel meso-formyloctaethylporphyrin

Nickel meso-formyloctaethylporphyrin is produced (Grigg, R. et al., *J. Chem. Soc. Perkin Trans 1*, 1972, pages 1789–1799) from a solution of 200 mg nickel meso-octaethylporphyrin in 150 mL 1,2-dichloroethane and 4.8 mL of a solution of phosphoryl chloride in dimethylformamide prepared by making a dropwise addition of 13.7 mL freshly distilled phosphoryl chloride to 10 mL dry dimethylformamide that has been cooled on an ice bath, and keeping the solution at room temperature of about 22° for 30 minutes. The 4.8 mL portion of the phosphoryl chloride solution is warmed to 50° on a water bath and the nickel meso-octaethylporphyrin solution is added dropwise thereto; the resulting reaction mixture is maintained at a temperature of 50°–55° and stirred for 15 minutes and is then warmed for an additional 30 minutes. A 150 mL portion of a saturated aqueous solution of sodium acetate is then added to the reaction mixture, after which stirring and heating are continued for an additional two hours. The organic and the aqueous layers are separated; the aqueous layer is extracted twice with 100 mL portions of diethyl ether; and the ether extracts are added to the organic layer. The organic solvents are then removed under reduced pressure, and the residue is dissolved in chloroform and chromatographed on an alumina column (3×30 cm). The product is crystallized from a mixed chloroformethanol solvent as long red felted needles.

The nickel meso-($\beta$-ethoxycarbonylvinyl) octaethylporphyrin was produced from a solution in 50 mL Xylene of 506 mg nickel meso-formyloctaethylporphyrin and 1.024 g (carbethoxymethylene)-triphenyl phosphorane.

Production of nickel meso-($\beta$-ethoxycarbonylvinyl) octaethylporphyrin

The xylene solution of nickel meso-formyloctaethylporphyrin and (carbethoxymethylene)-triphenyl phosphorane was heated under reflux for 18 hours. The solution was cooled; the xylene was removed in vacuo; and the solid which remained was dissolved in the minimum amount of dichloromethane and chromatographed on silica. A minor fraction of nickel meso-formyloctaethylporphyrin and a major red fraction were recovered. The solvent was removed from the red fraction; the solid which remained was recrystallized from a solvent composed of equal parts by volume of dichloromethane and methanol, yielding 455 mg small brown needles. The product was identified by nuclear magnetic resonance as nickel meso-($\beta$ethoxycarbonylvinyl) octaethylporphyrin.

Production of meso-[$\beta$-(ethoxycarbonyl)vinyl] octaethylporphyrin

A solution of 621 mg of nickel meso-($\beta$-ethoxycarbonylvinyl) octaethylporphyrin in 10 mL concentrated sulfuric acid is allowed to stand at room temperature of about 22° for 2 hours. Additions of 100 mL dichloromethane and enough saturated sodium bicarbonate to neutralize the reaction mixture are then made. The organic layer is then collected, washed and dried, and the solvent is removed. The crude product is purified by crystallization from dichloromethant-methanol.

Production of meso-[3-(hydroxy)propenyl] octaethylporphyrin

A solution of 200 mg meso-[$\beta$-(ethoxycarbonyl)vinyl] octaethylporphyrin in 100 mL dry tetrahydrofuran is cooled under nitrogen to –78°, using an acetone/dry ice bath. An excess of diisobutyl aluminum hydride in dry tetrahydrofuran (20 mL of 1M solution) is then added, followed by one hour of stirring at reduced temperature. Additions are then made of 100 mL water, 100 mL of a 10 percent aqueous solution of sodium hydroxide, and 200 mL water, and the resulting mixture is stirred for 30 minutes at room temperature of about 22°. The organic layer is then collected, washed and dried, and the solvent is removed under vacuum. The crude product is purified by crystallization from dichloromethane-methanol.

Production of octacthylbenzochlorin

A solution of 150 mg meso-[3-(hydroxy)propenyl] octacthylporphyrin in 3 mL concentrated sulfuric acid is kept at room temperature for 5 minutes, after which time a 20 mL portion of dichloromethane is added to the solution. Saturated aqueous sodium bicarbonate is then added until the reaction mixture is neutral. The organic layer is then collected, washed and dried, and the solvent is removed. The crude product was purified by crystallization from dichloromethane-methanol which contained 9%, methanol.

Production of Ni octaethylbenzochlorin

A solution is prepared by dissolving 20 mg octaethyl benzochlorin in a mixed solvent composed of 15 mL dichloromethane and 5 mL methanol and a 100 mg portion of nickel acetate is added to the solution; the mixture which results is refluxed for about 2 hours until the electronic spectrum of the reaction mixture indicates that chelation is complete. The reaction mixture is then concentrated to 7 mL and allowed to cool to room temperature of about 22°. Product which precipitates is recovered by filtration, dissolved in a mixed solvent composed of 5 mL dichloromethane and 2 mL methanol, and recrystallized, yielding the Ni complex of octaethylbenzochlorin.

Production of Cu octaethylbenzochlorin

A solution was prepared by dissolving 20 mg octaethyl benzochlorin (Morgan et al., "Observations on the Synthesis and in vivo Photodynamic Activity of some Benzochlorins", *Photochemistry and Photobiology* Vol. 55, No. 1, pages 133–136, 1992) in a mixed solvent composed of 15 mL dichloromethane and 5 mL methanol and a 100 mg portion of copper acetate was added to the solution; the mixture which resulted was refluxed for about 2 hours until the electronic spectrum of the reaction mixture indicated that chelation was complete. The reaction mixture was then concentrated to 7 mL and allowed to cool to room temperature of about 22°. Product which precipitated was recovered by filtration, dissolved in a mixed solvent composed of 5 mL dichloromethane and 2 mL methanol, and recrystallized, yielding the Cu complex of octaethylbenzochlorin (yield, 90 percent of theory).

The procedure of Example 1 can be used to produce benzochlorinimine according to the invention from Ni octaethylbenzochlorin and from other benzochlorins which can be produced by the method of Example A from the corresponding porphyrins (note that the identities of R1 through R8 in the Ni benzochlorins of the invention are the same as in the porphyrin starting material for Example A; this is generally true). Porphyrins having an appropriate structure to produce benzochlorinimine metal complexes according to the instant invention (formula setforth above, and identified by legend where R11 is hydrogen) are either known or can be produced by known reactions from the requisite dipyrrolic intermediates, e.g., dipyrromethanes and dipyrromethenes, which, in turn are either known or can be synthesized from the requisite pyrroles. The requisite pyrroles, if not available, can be synthesized from the requisite pyrroles. The requisite pyrroles, if not available, can be synthesized by the classical Knorr Reaction and variations, and by other known reactions, and can be manipulated and transformed (see, for for example, David Dolphin, *The Porphyrins*, Volume I, Structure and Synthesis, Part A, Academic Press, New York, San Francisco and London, 1978, pages 101–163). The pyrroles have the following structure:

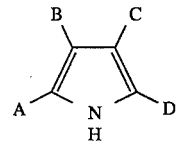

where A can be H, $CH_3$, an ester, a nitrile, a cyanovinyl or an amide group, D can be H, an ester, a nitrile, a cyanovinyl or an amide group and B and C are substituents which appear in the ultimate porphyrin, frequently lower alkyl groups, particularly methyl and ethyl.

Dipyrrolic intermediates, e.g., dipyrromethanes and dipyrromethenes, can be synthesized from pyrroles, and can be converted to porphyrins by known reactions; some porphyrins can be synthesized directly from pyrroles (see, for example, David Dolphin, supra, pages 85–100 and 163–234). Dipyrromethanes and dipyrromethenes have the following structures.

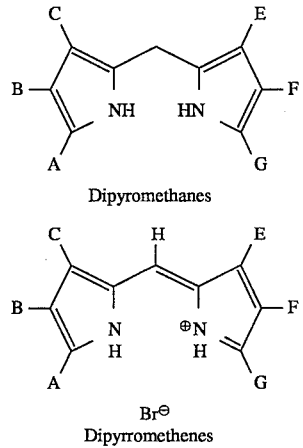

By way of example, "Octamethylpor phyrin" can be synthesized by heating 3,4-dimethylpyrrole (foregoing structure, where A is HOOC, B and C are $CH_3$ and D is $CH_2OH$) at 160°–170° and "Octaethylporphyrin" can be synthesized by heating 3,4-diethylpyrrole, where A is HOOC, B and C are $CH_2CH_3$ and D is $CH_2OH$. Porphyrins can also be produced from dipyrromethanes by way of an aldehyde coupling reaction, a formic acid or orthoformate ester condensation, by the "dialdehyde synthesis" or by the Vilsmeier pyrroketone synthesis, and from dipyrromethenes by the Fischer synthesis, or by reaction with dipyrromethanes. The porphyrins that are produced have the following structure where R is hydrogen and R1 through R4 and R5 through R8 have the same meanings as B, C, E and F in the dipyrromethane and dipyrromethene starting materials when the porphyrins are synthesized from these precursors:

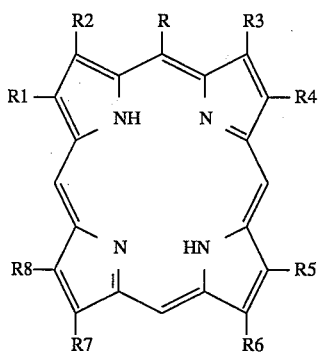

In octamethylporphyrin and octaethylporphyrin, R is hydrogen and R1 through R8 are methyl in the former and ethyl in the latter.

Ni Octaethylporphyrin, Ni Octamethylporphyrin and Ni complexes of other known porphyrins and of porphyrins which can be synthesized by the procedures summarized above produce, when used in the procedure of Example A, Ni complexes of benzochlorins having the structure of FIG. 1, supra, where M is Ni and R10, R11, R12 and R14 are hydrogen. These benzochlorins, when used in the procedure of Example 1, produce Cu or Ni benzochlorinimines according to the invention having the structure set forth above, where R11 is hydrogen. The benzochlorins of FIG. 1 can be reacted with the Vilsmeier reagent to introduce a formyl group as R10. The formyl group, after separation of the isomers, if necessary, can be reduced to $CH_3$, or can be The method of Example C, supra, can be used to produce metal complexes of benzochlorinimines according to the invention. Specifically, an equivalent amount of a benzochlorinimines according to the invention. Specifically, an equivalent amount of a according to the invention can be substituted for the octaethyl benzochlorinimine, or copper acetate can be substituted for the nickel acetate, or both substitutions can be made. In this manner, benzochlorinimine metal complexes having the structure indicated by the foregoing formula where M is either Cu or Ni can be produced from benzochlorinimines having the structure indicated by the foregoing formula. Iron complexes can be produced by the method of Example C by substituting $FeCl_3$ for the nickel acetate, in which case M in the formula is Fe(Cl). $NiCl_2$ can also be substituted, in which case M in the formula is $Ni(OH)_2$. Other benzochlorinimine metal complexes can also be made from the corresponding benzochlorinimines by the methods disclosed in "Morgan et al. II", U.S. Pat. No. 4,877,872, Oct. 31, 1989 (see column 32, line 56 to column 34, line 7) for the preparation of purpurin and chlorin metal complexes; all that is necessary is to substitute an equivalent amount of the benzochlorinimine metal complex for the purpurin or chlorin.

Similarly, porphyrinimine nickel complexes, chlorinimine nickel complexes, bacteriochlorinime nickel complexess, chlorophyllimine nickel complexes, bacteriochlorophyllimine nickel complexes, purpurinimine nickel complexes, reduced purpurinimine nickel complexes, verdinimine nickel complexes, and Diels Alder Adduct Imine nickel complexes, and isobacteriochlorin metal complexes can be produced by the method of Example 1, by substituting for the Ni Octaethyl Benzochlorin starting material an equivalent amount of the nickel complex of an appropriate porphyrin, chlorin, bacteriochlorin, chlorophyll, bacteriochlorophyll, purpurin, reduced purpurin, verdin, Diels Alder adduct, or isobacteriochlorine to produce the desired imine. The imines can then be produced from the imine metal complexes by the method of Example B, and other imine metal complexes can then be produced by the method of Example C and the variations discussed above. The required porphyrin starting materials are all either available or can be produced by the methods discussed above. The required purpurin metal complex and reduced purpurin metal complex starting materials can all be produced by the methods disclosed in "Morgan et al. III" (U.S. Pat. No. 5,051,415, granted, where the reduced purpurins are named as "chlorins"). The required Diels Alder Adducts can all be produced by the method of "Levy et al." (U.S. Pat. No. 4,883,790, granted Nov. 28, 1989). The required verdin metal complex starting materials can all be produced by the method of Morgan et al. (supra). The required chlorin, bacteriochlorin, chlorophyll, isobacteriochlorin, or bacteriochlorophyll starting material can be produced by the methods disclosed in David Dolphin, *The Porphyrins*, Volume II, Academic Press, New York, San Francisco and London, 1978, (see pages 1–85 and 131–156). The required bacteriochlorin Diels Alder Adducts to produce Imines I, II and III thereof can be produced as described in Morgan et al., *J. Med. Chem*, 1990–1991, Volume 34, No. 7, pages 2126–2133, and the required starting materials to produce the Chlorinimines and metal complexes, the families of compounds which are designated Isobacteriochlorinimine I and Isobacteriochlorinimine II and the metal complexes thereof and the families of compounds which are designated bacteriochlorinimine and the metal complexes thereof, which include a $CH_2$ group or O which, in either case, is bonded to a carbon of the pyrrole ring by a double bond, can all be produced by procedures which are disclosed in the literature. A dimer composed of one molecule of any of the imines or imine metal complexes of the instant invention and a second molecule of the same or a different imine or imine metal complex of the instant invention or the parent porphyrin, chlorin, bacteriochlorin, chlorophyll, bacteriochlorophyll, purpurin, reduced to $CH_2OH$ or convened to an oxime group, which can then be converted to a cyano group, which, in turn, can be converted to an amide. The formyl group can also be reacted with Wittig reagents to give alkyl, alkenyl or carboxy side chains or to introduce the previously identified substituents which have an amine or an alcoholic OH function in the R9 or in the R10 position.

The procedure of Example 1, supra, produces Cu Benzochlorinimine I from Cu octaethyl benzochlorin. While octaethyl benzochlorin can be produced from meso-(β-hydroxyvinyl)-octaethyl porphyrin, it is not possible, so far as is known, to produce the uncomplexed benzochlorinimine corresponding with Cu Benzochlorinimine I from octaethyl benzochlorin. Accordingly, to produce the benzochlorinimines according to the instant invention (structures set forth above) the corresponding Ni or Cu benzochlorinimines should be produced by the method of Example 1, and the Ni or Cu should then be removed by acid treatment. Acid treatment to remove metals from porphyrins is disclosed in Vicente et al., supra, and to remove Ni from Ni Octaethyl Benzochlorin is illustrated in Example B, below.

Example B

A 40 mg portion of Ni Octaethyl Benzochlorin was stirred for 2 ½ hours in 4 mL concentrated (98 percent) sulfuric acid. The reaction mixture which resulted was poured onto ice, neutralized with sodium hydrogen carbonate, and extracted with dichloromethane. Two reaction products (20 mg of each) were recovered by chromatographing the extract on silica gel. One of the products was identified as Octaethyl Benzochlorin, while the other was identified as the sulfonate thereof. The sulfonate was found to have the structure of FIG. 2, supra, where R14 is $SO_3Na$, and is attached either to the available carbon nearer R2 or to the available carbon nearer R3, probably the former. The octaethyl benzochlorin was crystallized from dichloromethane containing 2%, methanol, while the octaethyl benzochlorin sulfonate was crystallized from dichloromethane. Lambda maximum, U V, was 657 nm for both products. The $SO_3Na$ group can be converted to $SO_3H$ by acidifying the sulfonate, and the hydrogen of the $SO_3H$ group can be converted to other cations by neutralizing with other bases.

The Ni and other metal complexes of the octaethyl benzochlorin and of the octaethyl benzochlorin sulfonate can be produced from octaethyl benzochlorin and from octaethyl benzochlorin sulfonate, a suitable procedure for producing the Ni complex being described below as Example C.

Example C

Production of Ni octaethyl benzochlorin sulfonate

A solution is prepared by dissolving 20 mg octaethyl benzochlorin sulfonate in a mixed solvent composed of 15 mL dichloromethane and 5 mL methanol and a 100 mg portion of nickel acetate is added to the solution; the mixture which results is refluxed for about 2 hours until the electronic spectrum of the reaction mixture indicates that chelation is complete. The reaction mixture is then concentrated to 7 mL and allowed to cool to room temperature of about 22°. Product which precipitates is recovered by filtration, dissolved in a mixed solvent composed of 5 mL dichloromethane and 2 mL methanol, and recrystallized, yielding the Ni complex of octaethylbenzochlorin sulfonate, which has the structure of FIG. 1, supra, where R1 through R8 are ethyl, R14 is $SO_3H$, R10, R11 and R12 are hydrogen and M is Ni. The procedure of Example 1 can then be used to convert the Ni complex of octaethylbenzochlorin sulfonate to a benzochlorinimine according to the invention having the structure set forth above, and designated by legend, where R1 through R8 are ethyl, R11 is $SO_3H$, the identities of R' and R" depend on the dialkyl formamide used, and A is Cl. reduced purpurin, verdin, Diels Alder adduct, benzochlorin or a metal complex of one of the foregoing can be produced by the method disclosed in Morgan et al. II(supra). Such dimers are products of reaction between a $CO_2R'$, $CH_2CO_2R'$ or $CH_2CH_2CO_2R'$ group of one of the imines or imine metal complexes and an amino nitrogen or an alcoholic OH group of the other of the imines or imine metal complexes.

By suitable substitution of starting materials, and the synthesis of porphyrin and other starting materials as discussed above, if necessary, the procedures of Examples A and 1 can be used to produce Ni benzochlorins and other Ni imines according to the invention having the metal complex structures set forth above, where M is Ni, R' and R" can be the same or different and each is hydrogen or an alkyl group having from 1 to 4 carbon atoms, and each of R1 through R11 is:

H or CHO, an alkyl group other than t-butyl having from 1 to 4 carbon atoms, an alkylene group having from 2 to 4 carbon atoms, a group having the formula $R_3N(R_4)_2$ where $R_3$ is a bivalent aliphatic hydrocarbon radical having from 1 to 4 carbon atoms, wherein any carbon to carbon bond is either a single or a double bond, and not more than one is a double bond; $R_4$ is hydrogen or an alkyl radical having from 1 to 2 carbons atoms and the two $R_4$ groups can be the same or different, a group having the formula $R_3N(R_5)_3$ A where $R_3$ is a bivalent aliphatic hydrocarbon radical having from 1 to 4 carbon atoms, wherein any carbon to carbon bond is either a single or a double bond, and not more than one is a double bond; A is a physiologically acceptable anion and $R_5$ is an alkyl group having from 1 to 2 carbon atoms and the three $R_5$ groups can be the same or different, a group having the formula $R_3OH$ where $R_3$ is a bivalent aliphatic radical having from 1 to 4 carbon atoms, wherein any carbon bond is either a single or a double bond, and not more than one is a double bond, or $CO_2R'$, $CH_2CO_2R'$ or $CH_2CH_2CO_2R'$ where R' is H, or alkyl group other than t-butyl having from one to four carbon atoms.

Benzochlorinimines according to the invention which have the structure of of the foregoing formula can be produced as discussed above by removing the Cu or Ni from the corresponding Cu or Ni benzochlorinimines, and those benzochlorinimines can be metallated as discussed above to produce benzochlorinimine metal complexes where M comprises a metal cation that is complexed with two of the nitrogens of the benzochlorinimine and is any of those metals disclosed above. Similarly, other imines according to the invention can be produced by removing Ni from the corresponding Ni imines, and the imines can be metallized as discussed above to produce imine metal complexes where M comprises a metal cation that is complexed with two of the nitrogens of the imine and is any of those metals disclosed above.

An anion exchange resin can be used to introduce any desired anion ($A^-$ in the foregoing formulas) into an imine or imine metal complex according to the invention. The anion exchange resin is merely regenerated with a salt or acid which has the desired anion, and the imine or imine metal salt is poured through a column packed with the anion exchange resin.

The production of Ni Benzochlorinimine I solutions in the specific non-ionic solubilizer that is available under the designation CREMOPHOR EL, and the production of emulsions of such solutions with 1,2-propanediol and saline solution is described above, as is the use of such solutions to detect and treat Pk tumors. It will be appreciated that benzochlorinimines and other imines according to the invention and their metal complexes can be dissolved in other non-ionic solubilizers and that the solutions can be used to produce emulsions that can be administrated intravenously. For example, other reaction products of ethylene oxide and castor oil can be so used, as can reaction products of ethylene, propylene and other similar oxides with other fatty acids and the reaction products of propylene and other similar oxides with castor oil. Similarly, glycols other than 1,2- propanediol can be used in producing the emulsions for intravenous administration, or the glycol can be omitted, particularly if the solubilizer is prepared to have a lower viscosity and greater compatibility with water, by comparison with the solubilizer that is available under the designation CREMOPHOR EL. It is necessary only that the solution or emulsion be one which is physiologically acceptable and of a suitable concentration, or dilutable to a suitable concentration, for intravenous administration or for local administration, should that be desirable. An indefinitely large number of such solutions and emulsions will be apparent to those skilled in the relevant art from the foregoing specific disclosure. Similarly, the aqueous phase need not be 0.9 percent or any other concentration of sodium chloride. Such saline is presently favored for intravenous administration, but other aqueous phases can also be used, so long as the entire composition is physiologically acceptable for intravenous administration and, in fact, other aqueous phases may subsequently be favored. Indeed, other aqueous phases or organic phases may also be favored for local administration.

Dosages ranging from 3.5 to 7 mg per kg of body weight were used in the in vivo procedures described above. It has been determined only that the biological consequences described above were caused by the dosages administered, not that any dosage reported is either a minimum or a maximum. It will be appreciated, therefore, that it is necessary only to use an effective amount of a benzochlorin or metal complex according to the invention in the detection and treatment of tumors, preferably as small a dosage as possible, and that the exact dosage can be determined by routine experimentation. While systemic administration has been described above, specifically intravenous, it will also be appreciated that local administration will be suitable, at least in some instances.

Illumination of tumors containing a benzochlorinimine or another imine or a metal complex is accordance with the instant invention can be a surface illumination with a conventional source for pulsed light of a suitable wavelength, frequency and intensity, as described above, or can be a surface illumination with a laser. The illumination can also be into the body of a tumor, for example through optical fibers inserted thereinto.

The benzochlorinimines, other imines, metal complexes, and dimers of the present invention can be used as discussed above for the treatment of tumors, and they can also be used for the dissolution of plaques in blood vessels, and for the treatment of topical conditions such as psoriasis, fungal infections, acne, athletes foot, warts, papilloma and for the sterilization of blood for transfusions, as will now be explained. While the intravenus injection of the benzochlorins and the like has been described, they can also be injected subcutaneously, intramuscularly or intraperitoncally. Dosages can vary widely, but the in vivo test data reported above indicate that the intravenous administration of up to 7 mg per kg of body weight is safe. The benzochlorinimines and the like can be formulated in lotions, suspensions or pastes for localized treatment, e.g., of superficial tumors or skin disorders.

Various changes and modification can be made from the specific details of the invention as described above without departing from the spirit and scope thereof as defined in the appended claims.

We claim:

1. As a cancer tumor treating method by means of photodynamic therapy with composition of matter, a purified imine of a porphyrin, a chlorin, a bacteriochlorin, a chlorophyll, a bacteriochlorophyll, a purpurin, a reduced purpurin, a verdin, a Diels Alder adduct, an isobacteriochlorin, a benzochlorin or a metal complex of one of the foregoing imines having one of the structures set forth below, and identified by legend:

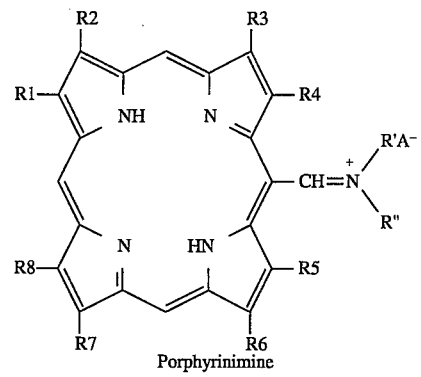
Porphyrinimine

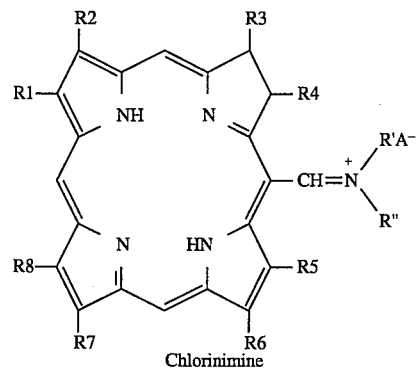
Chlorinimine

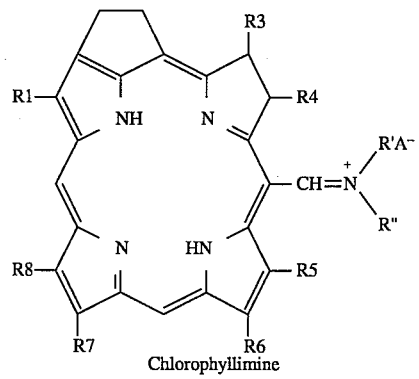
Chlorophyllimine

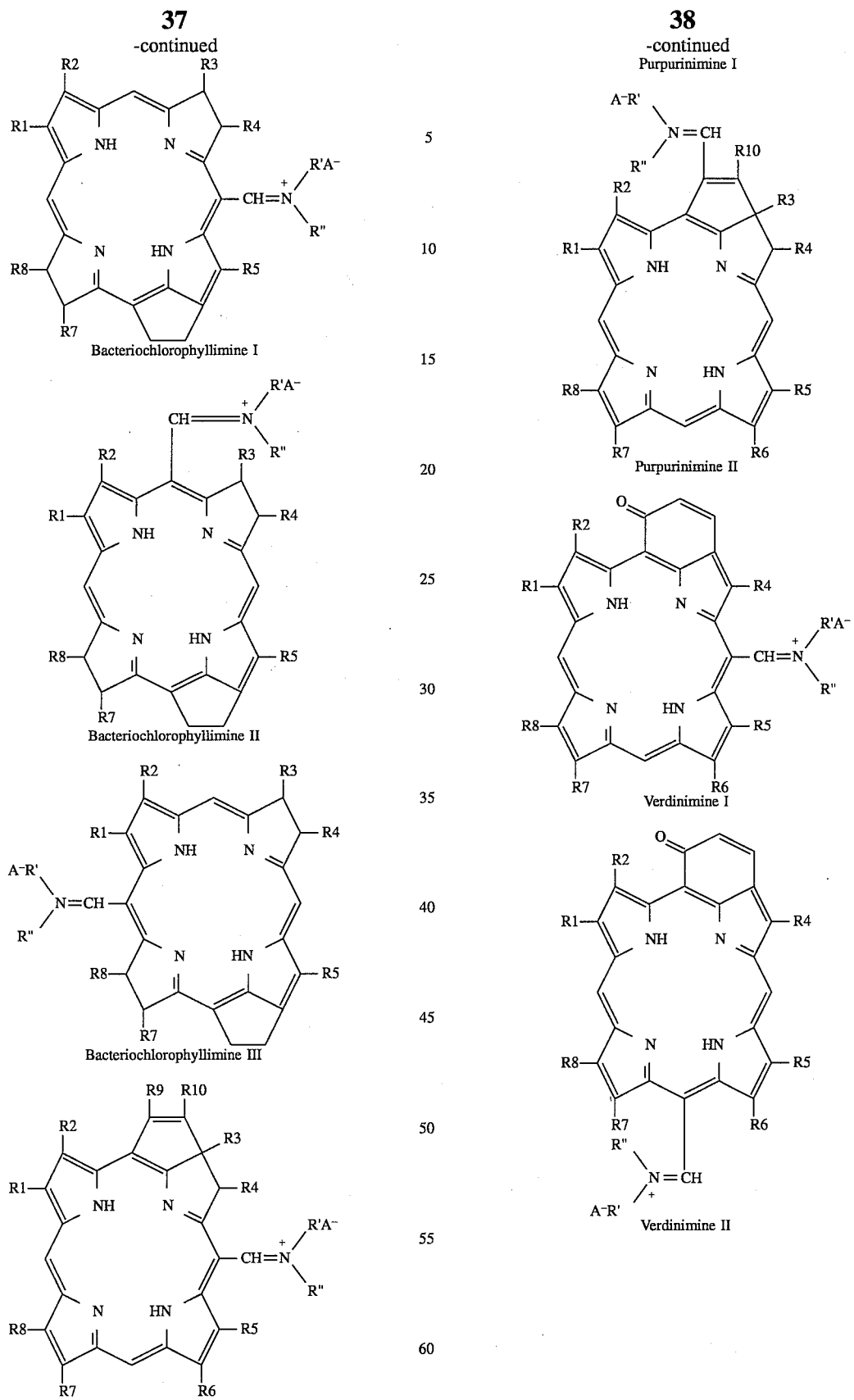

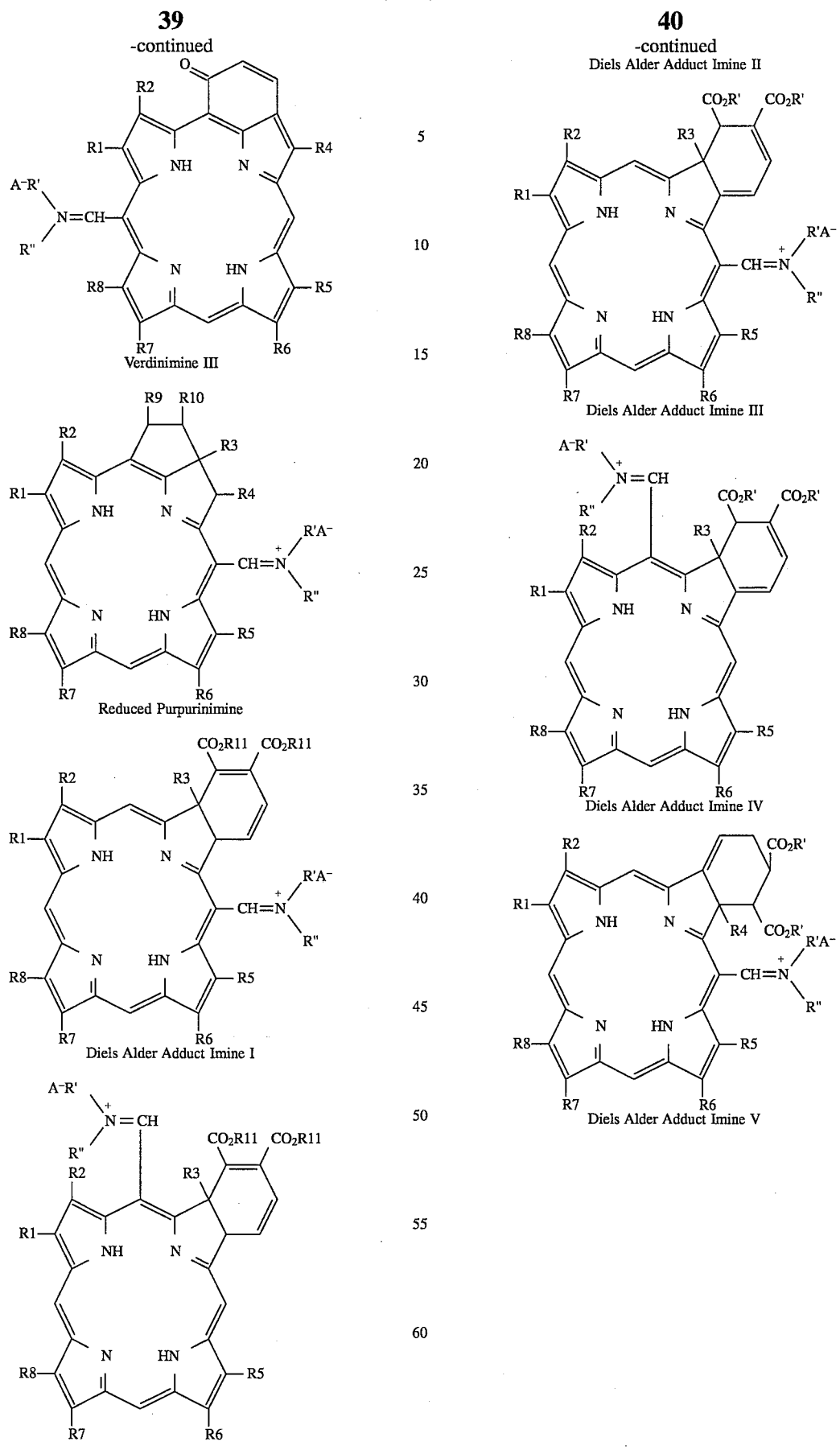

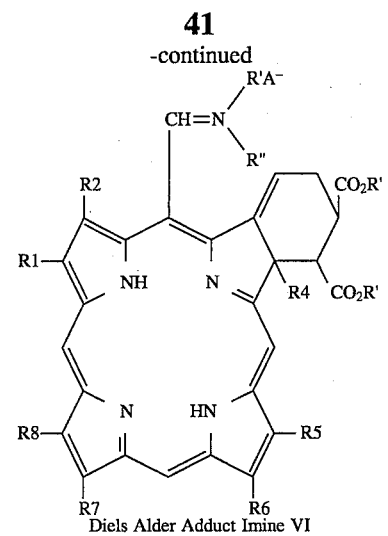
Diels Alder Adduct Imine VI
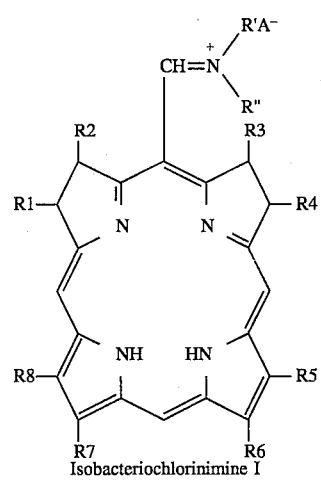
Isobacteriochlorinimine I
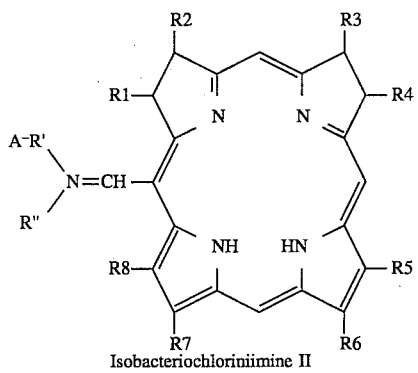
Isobacteriochloriniimine II
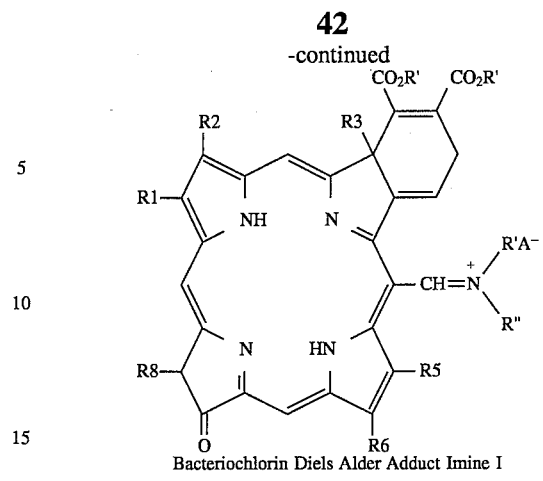
Bacteriochlorin Diels Alder Adduct Imine I
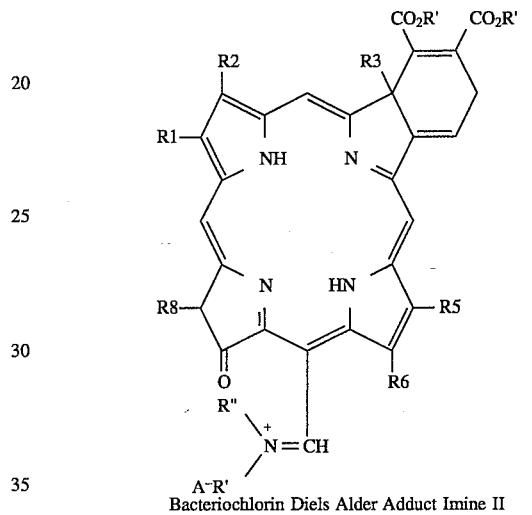
Bacteriochlorin Diels Alder Adduct Imine II
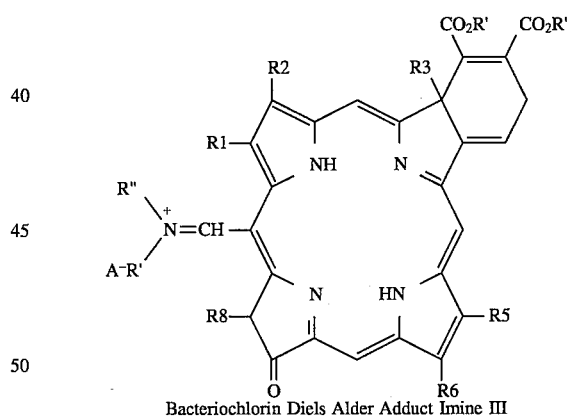
Bacteriochlorin Diels Alder Adduct Imine III

43
-continued
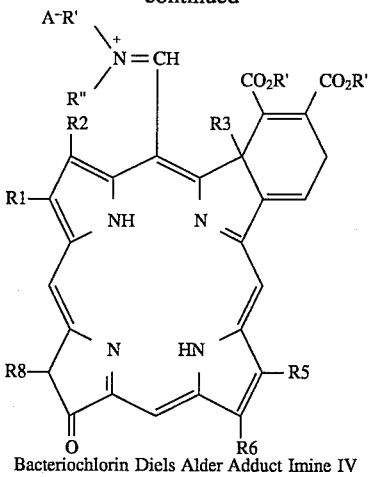
Bacteriochlorin Diels Alder Adduct Imine IV
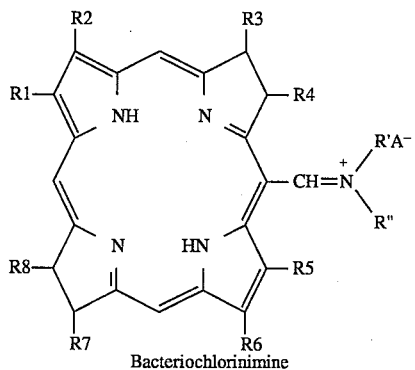
Bacteriochlorinimine
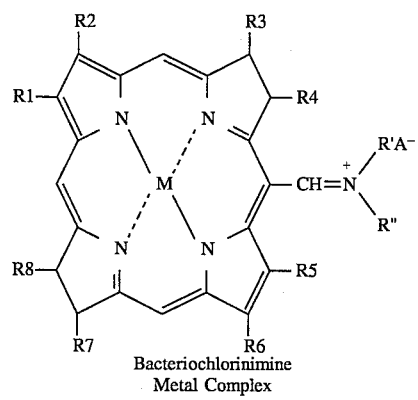
Bacteriochlorinimine
Metal Complex
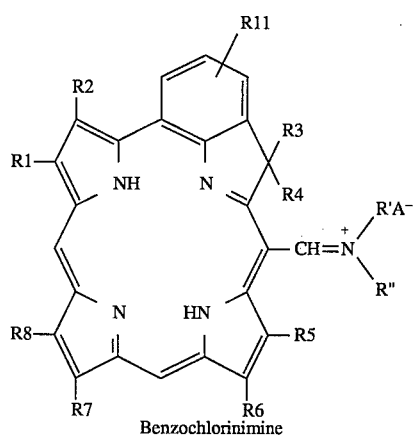
Benzochlorinimine
44
-continued
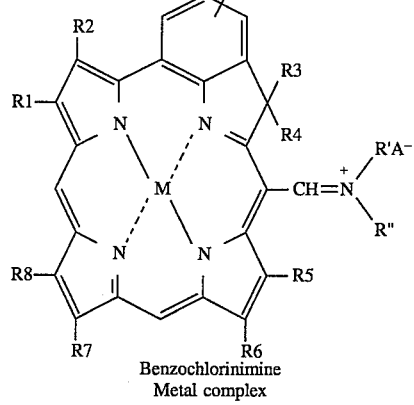
Benzochlorinimine
Metal complex
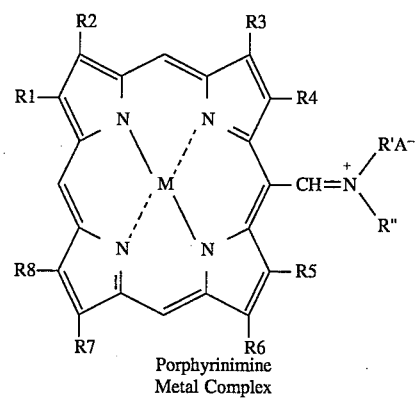
Porphyrinimine
Metal Complex
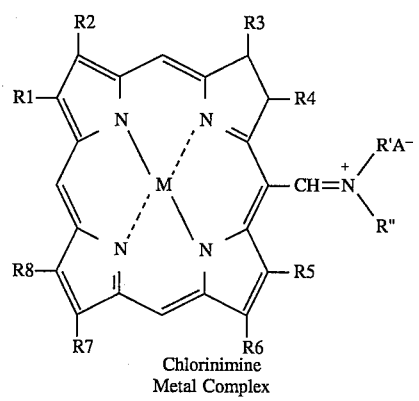
Chlorinimine
Metal Complex
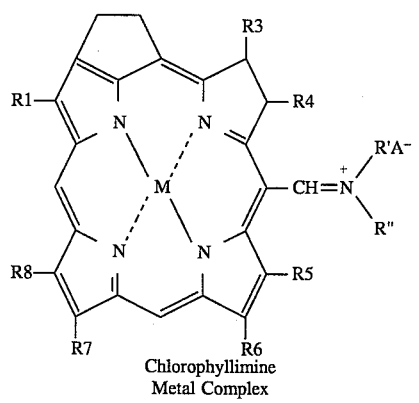
Chlorophyllimine
Metal Complex

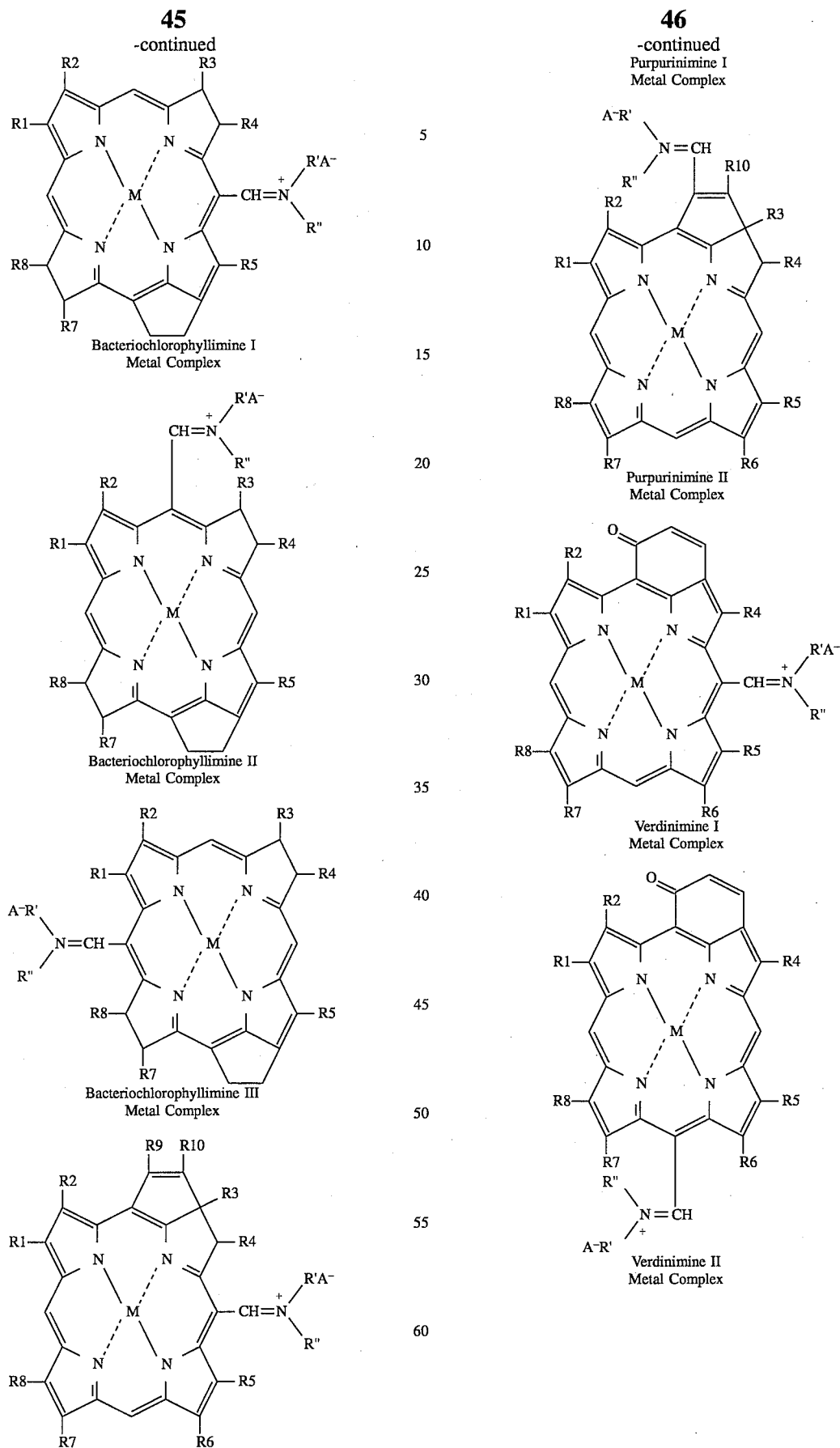

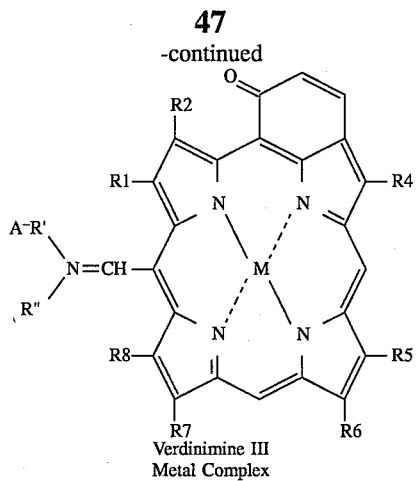
Verdinimine III
Metal Complex
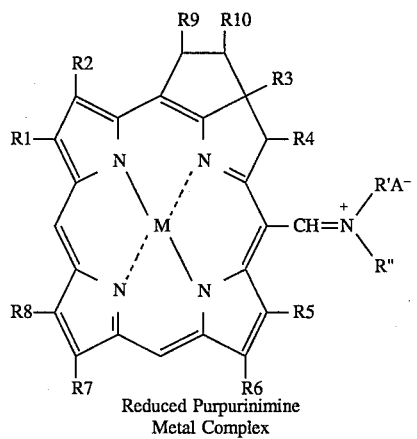
Reduced Purpurinimine
Metal Complex
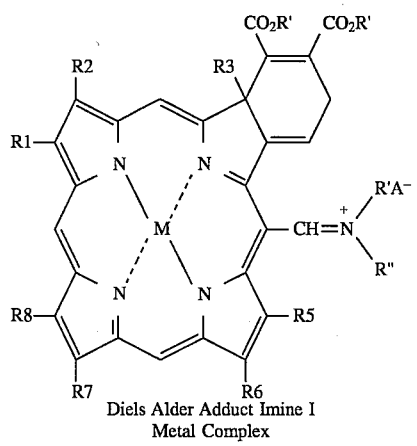
Diels Alder Adduct Imine I
Metal Complex
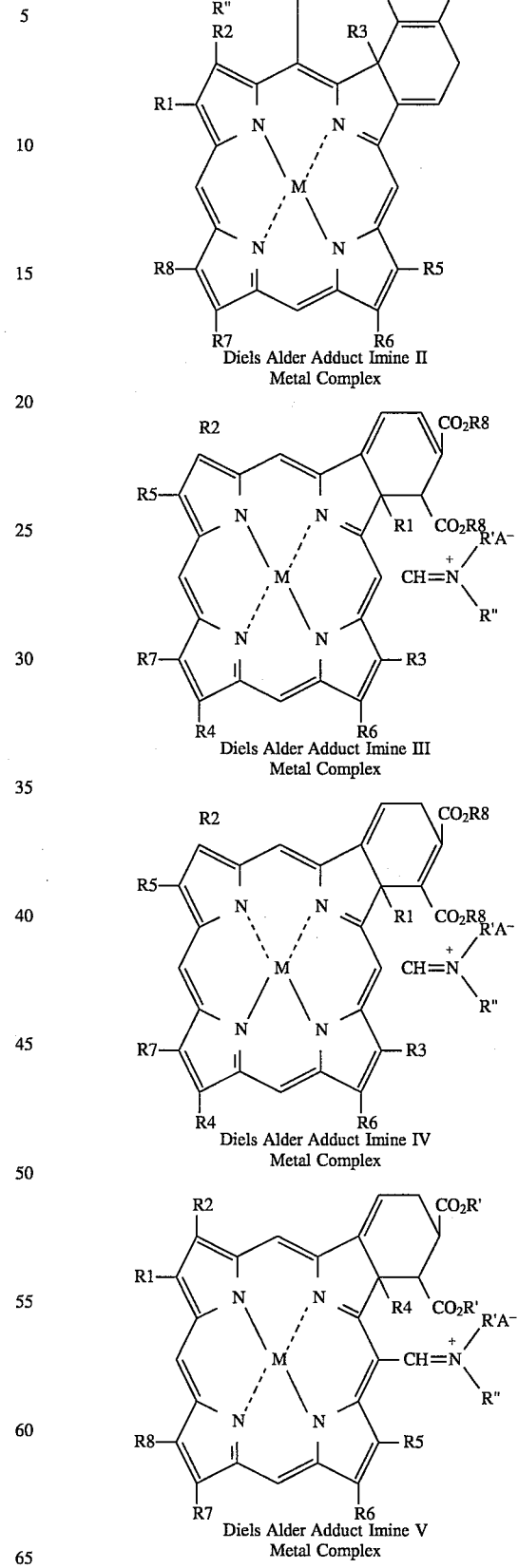

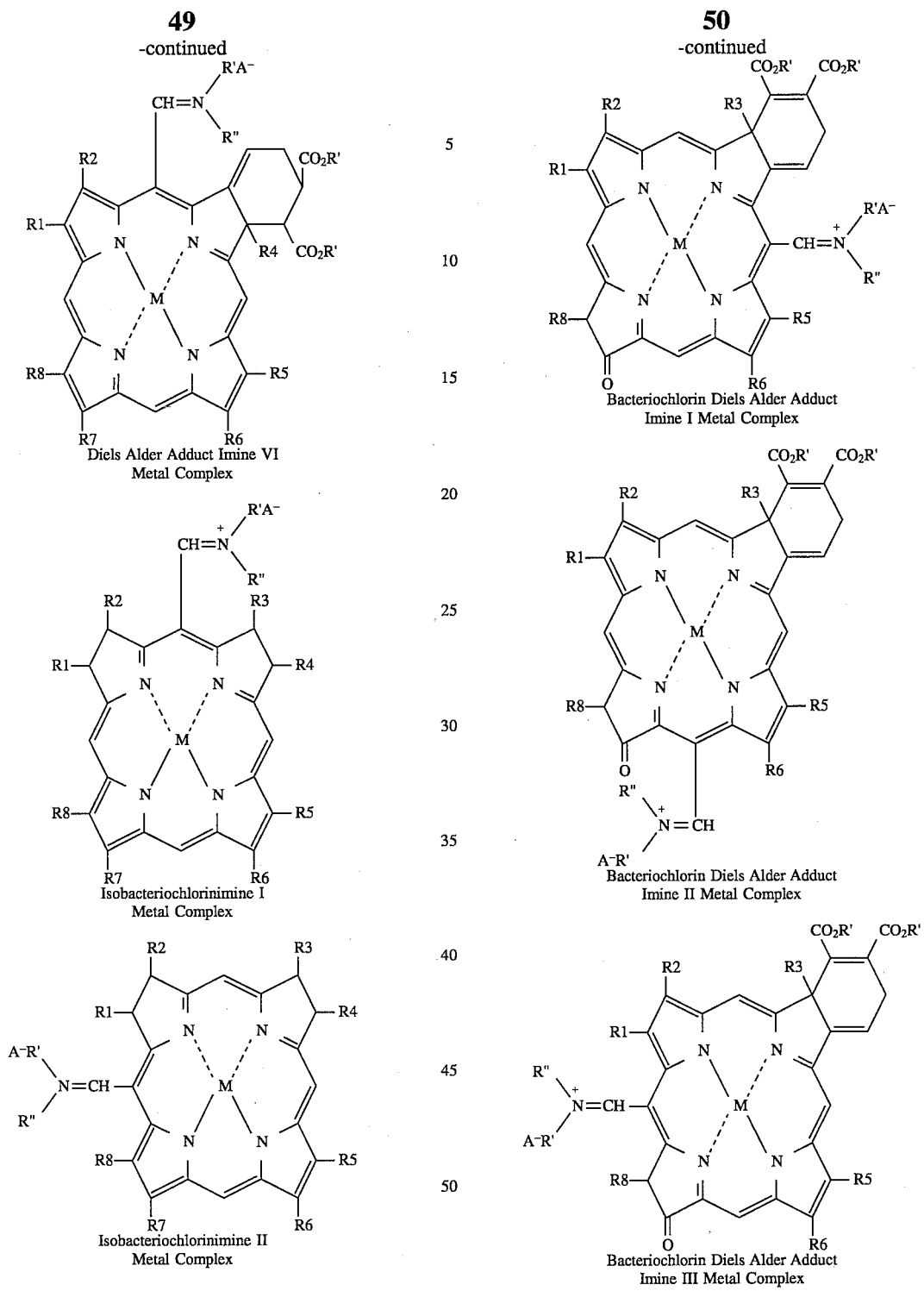

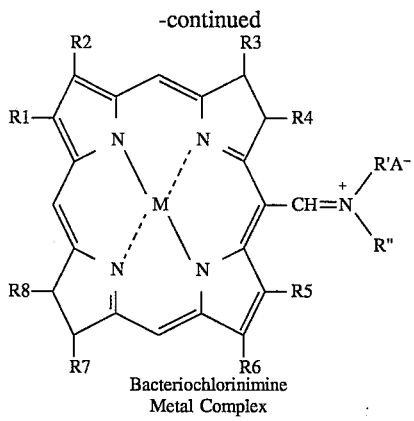

Bacteriochlorinimine
Metal Complex wherein

M comprises a metal cation that is complexed with two of the nitrogens of the benzochlorin and is Ag, Al, Ce, Co, Cr, Cu, Dy, Er, Eu, Fe, Ga, Gd, Hf, Ho, In, La, Lu, Mn, Mo, Nd, Pb, Pd, Pr, Pt, Rh, Sb, Sc, Sm, Sn, Tb, $^{99m}$Tc, Th, Ti, Tl, Tm, U, V, Y, Yb, Zn or Zr, A is a physiologically acceptable anion, R' and R" can be the same or different, and each is hydrogen or an alkyl group having from one to four carbon atoms, and each of R1 through R11 is H or CHO, an alkyl group other than t-butyl having from 1 to 4 atoms, an alkylene group having from 2 to 4 carbon atoms, a group having the formula $R_3N(R_4)_3$ A where $R_3$ is a bivalent aliphatic hydrocarbon radical having from 1 to 4 carbon atoms, wherein any carbon to carbon bond is either a single or a double bond, and not more than one is a double bond; $R_4$ is hydrogen or an alkyl radical having 1 to 2 carbon atoms and the two $R_4$ groups can be the same or different, a group having the formula $R_3N(R_5)_3$ A where $R_3$ is a bivalent hydrocarbon radical having from 1 to 4 carbon atoms, wherein any carbon to carbon bond is either a single or a double bond, and not more than one is a double bond; A is a physiologically acceptable anion and $R_5$ is an alkyl group having from 1 to 2 carbon atoms and the three $R_5$ groups can be the same or different, a group having the formula $R_3OH$ where $R_3$ is a bivalent aliphatic hydrocarbon radical having from 1 to 4 carbon atoms, wherein any carbon to carbon bond is either a single or a double bond, and not more than one is a double bond, or $CO_2R'$, $CH_2CO_2R'$ or $CH_2CH_2CO_2R'$ where R' is H, or an alkyl group other than t-butyl having from one to four carbon atoms, with the provisos that R11 can be $SO_3H$ or a salt thereof, that, in the foregoing chlorinimines and metal complexes, either R3 or R4 can be a $CH_2$ group or O which, in either case, is bonded to the carbon of the pyrrole ring by a double bond, that, in the foregoing families of compounds which are designated Isobacteriochlorinimines I and Isobacteriochlorinimines II and their metal complexes, either R1 or R2 can be a CH2 group or O which, in either case, is bonded to the carbon of the pyrrole ring by a double bond and, when either R1 or R2 is a $CH_2$ group or O, either R3 or R4 is also a $CH_2$ group or O which is bonded to the carbon of the pyrrole ring by and double bond, and that in the foregoing families of compounds which are designated bacteriochlorinimines and metal complexes, either R3 or R4 can be a $CH_2$ group or O which, in either case, is bonded to the carbon of the pyrrole ring by a double bond and, when either R3 or R4 is a $CH_2$ group or O, either R7 or R8 is also a $CH_2$ group or O which is bonded to the carbon of the pyrrole ring by and double bond.

2. A method for treating a human or animal patient which comprises administering an effective amount of a benzochlorin having the structure of Formula III or of a metal complex of a benzochlorin having the structure of Formula IV, below:

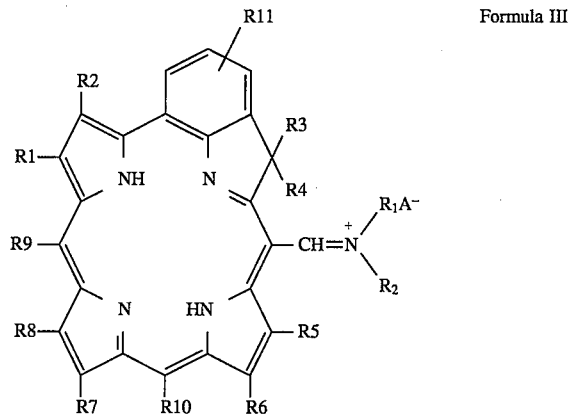

Formula III

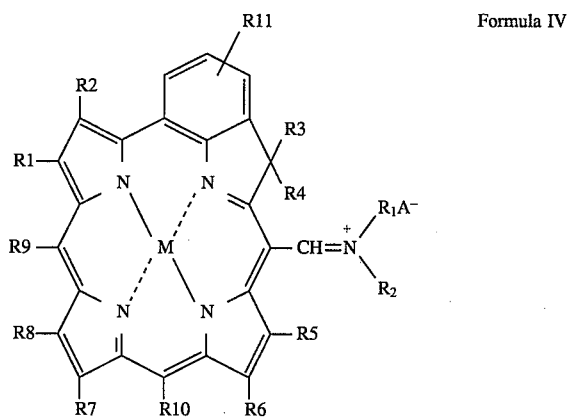

Formula IV wherein

M comprises a metal cation that is complexed with two of the nitrogens of the benzochlorin and is Cu, Fe or Ni, $R_1$ and $R_2$ can be the same or different and each is an alkyl group other than t-butyl having from 1 to 4 carbon atoms, and each of R1 through R11 is H or CHO, an alkyl group other than 1-butyl having from 1 to 4 carbon atoms, an alkylene group having from 2 to 4 carbon atoms, a group having the formula $R_3N(R_4)_2$ where $R_3$ is a bivalent aliphatic hydrocarbon radical having from 1 to 4 carbon atoms, wherein any carbon to carbon bond is either a single or a double bond, and not more than one is a double bond; $R_4$ is hydrogen or an alkyl radical having from 1 to 2 carbon atoms and the two $R_4$ groups can be the same or different, a group having the formula $R_3N(R_5)_3$ A where $R_3$ is a bivalent aliphatic hydrocarbon radical having from 1 to 4 carbon atoms, wherein any carbon to carbon bond is either a single or a double bond, and not more than one is a double bond; A is a physiologically acceptable anion and $R_5$ is an alkyl group having from 1 to 2 carbon atoms and the three $R_5$ groups can be the same or different, a group having the formula $R_3OH$ where $R_3$ is a bivalent aliphatic hydrocarbon radical having from 1 to 4 carbon atoms, wherein any carbon to carbon bond is either a single or a double bond, and not more than one is a double bond, or $CO_2R'$, $CH_2CO_2R'$ or $CH_2CH_2CO_2R'$ where $R'$ is H, or an alkyl group other than t-butyl having from one to four carbon atoms, with the proviso that R11 can be $SO_3H$ or a salt thereof, and irradiating the patient with pulsed excitation at a suitable wavelength and of sufficient intensity to promote residual benzochlorin or benzochlorin metal complex in the patient to the singlet state.

3. A method as claimed in claim 2 which comprises administering a benzochlorin metal complex wherein each of R9 through R11 is hydrogen, each of R1 through R8 is an alkyl group other than t-butyl having from 1 to 4 carbon atoms, and M is Ni.

4. A method of retarding growth of cancer tumors by means of photodynamic therapy using a benzochlorin metal complex as claimed in claim 1 wherein each of R9 through R11 is hydrogen, each of R1 through R8 is an alkyl group other than t-butyl having from 1 to 4 carbon atoms, and M is Cu.

5. A cancer tumor treating method using a composition consisting essentially of a solution in a solvent of a benzochlorin having the structure of Formula III or a metal complex of a benzochlorin having the structure of Formula IV, below:

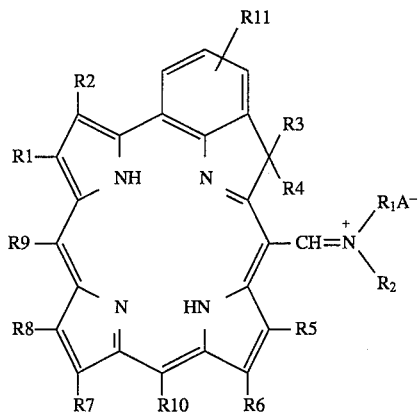

Formula III

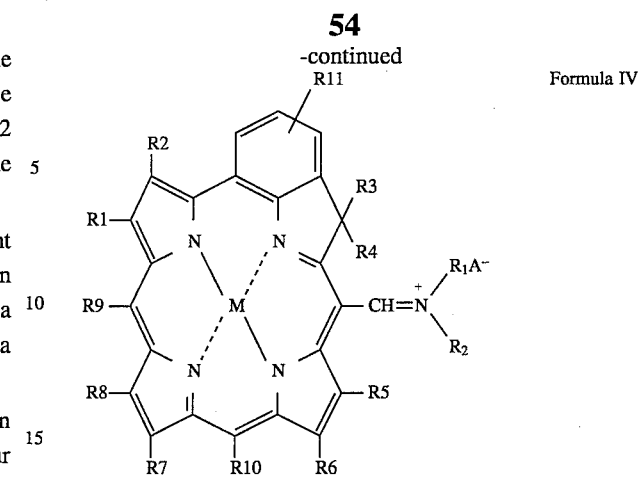

Formula IV wherein

M comprises a metal cation that is complexed with two of the nitrogens of the benzochlorin and is Cu, Fe or Sn, $R_1$ and R2 can be the same or different and each is an alkyl group other than t-butyl having from 1 to 4 carbon atoms, and each of R1 through R11 is H or CHO an alkyl group other than t-butyl having from 1 to 4 carbon atoms, an alkylene group having from 2 to 4 carbon atoms, a group having the formula $R_3N(R_4)_2$ where $R_3$ is a bivalent aliphatic hydrocarbon radical having from 1 to 4 carbon atoms, wherein any carbon to carbon bond is either a single or a double bond, and not more than one is a double bond; $R_4$ is hydrogen or an alkyl radical having from 1 to 2 carbon atoms and the two $R_4$ groups can be the same or different, a group having the formula $R_3N(R_5)_3$ A where $R_3$ is a bivalent aliphatic hydrocarbon radical having from 1 to 4 carbon atoms, wherein any carbon to carbon bond is either a single or a double bond, and not more than one is a double bond; A is a physiologically acceptable anion and $R_5$ is an alkyl group having from 1 to 2 carbon atoms and the three $R_5$ groups can be the same or different, a group having the formula $R_3OH$ where $R_3$ is a bivalent aliphatic hydrocarbon radical having from 1 to 4 carbon atoms, wherein any carbon to carbon bond is either a single or a double bond, and not more than one is a double bond, or $CO_2R'$, $CH_2CO_2R'$ or $CH_2CH_2CO_2R'$ where $R'$ is H, or an alkyl group other than t-butyl having from one to four carbon atoms, with the proviso that R11 can be $SO_3H$ or a salt thereof, and wherein the solution comprises an organic liquid equivalent to an ethylene/fatty acid reaction product solubilizer, and is one which is physiologically acceptable and of a suitable concentration or dilutable to a suitable concentration for intravenous administration.

6. A method of using a solution of a benzochlorin metal complex as claimed in claim 1 wherein each of R9 through R11 is hydrogen, each of R1 through R8 is an alkyl group other than t-butyl having from 1 to 4 carbon atoms, and M is Cu.

7. A method as defined in claim 1 in which there is an aqueous emulsion or suspension of a solution of a benzochlorin or a benzochlorin metal complex.

8. A method as defined in claim 1 in which the amount of the complex is equivalent to about 3.5 to 7 mg/kg of body weight of a patient.

9. A method as defined in claim 8 in which the amount of copper complex is about 3.5 mg/kg.

10. A method of dissolving plaques in blood vessels using photodynamic therapy with a composition of matter, a purified imine of a porphyrin, a chlorin, a bacteriochlorin, a chlorophyll, a bacteriochlorophyll, a purpurin, a reduced purpurin, a verdin, a Diels Alder adduct, an isobacteriochlorin, a benzochlorin or a metal complex of one of the foregoing imines having one of the structures set forth below, and identified by legend:

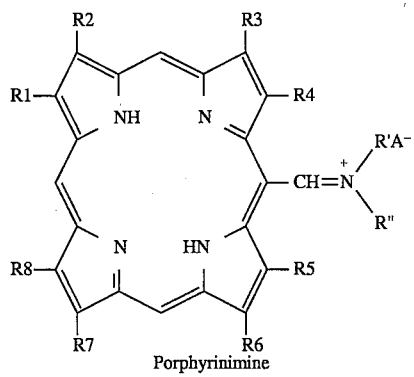
Porphyrinimine

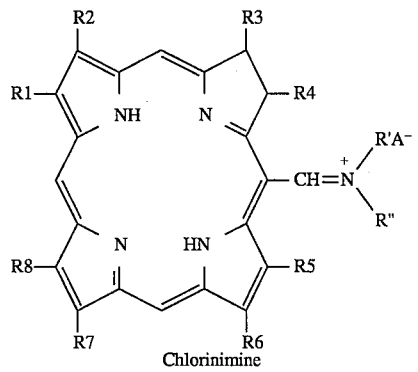
Chlorinimine

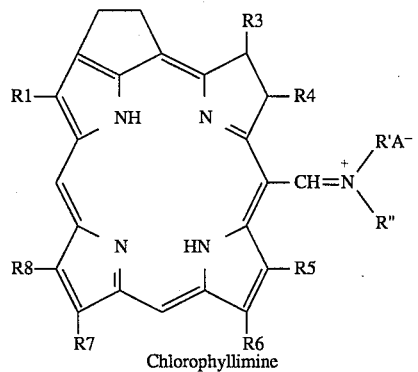
Chlorophyllimine

-continued

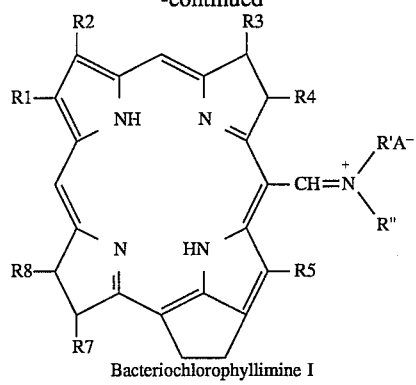
Bacteriochlorophyllimine I

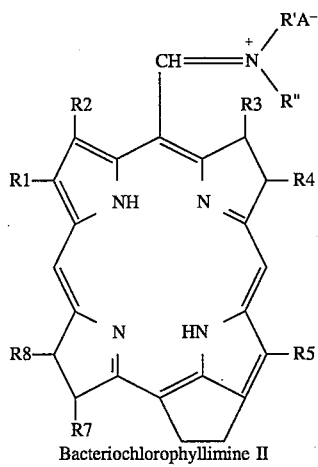
Bacteriochlorophyllimine II

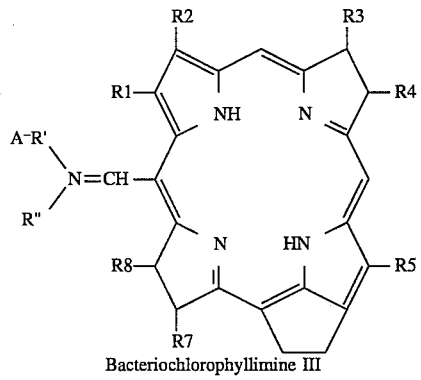
Bacteriochlorophyllimine III

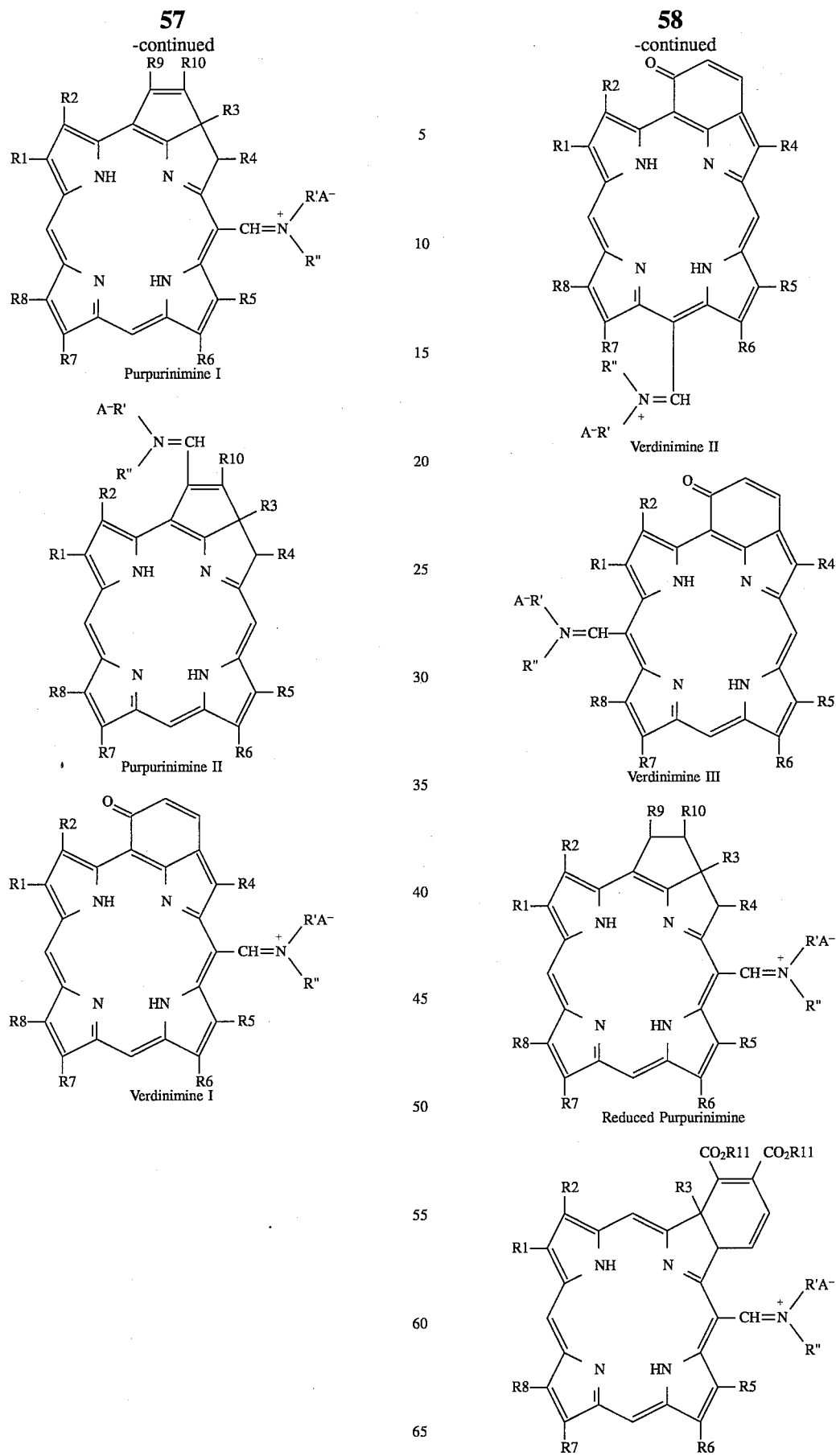

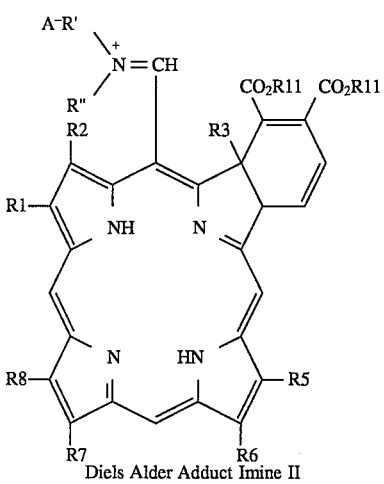
Diels Alder Adduct Imine II
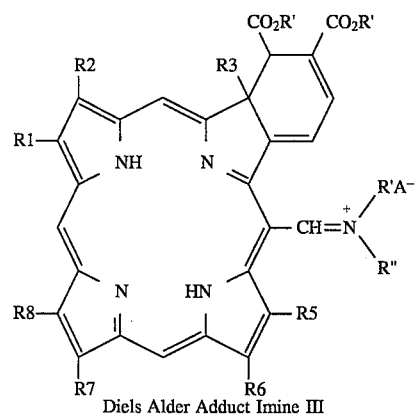
Diels Alder Adduct Imine III
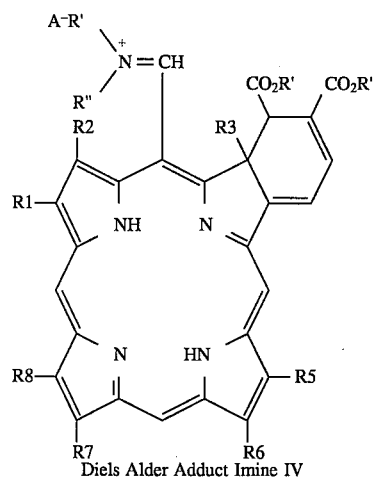
Diels Alder Adduct Imine IV
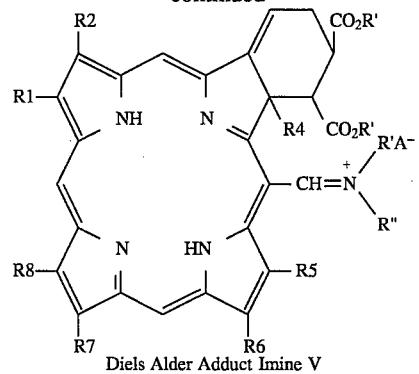
Diels Alder Adduct Imine V
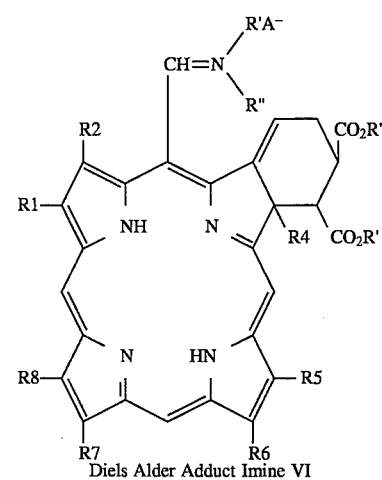
Diels Alder Adduct Imine VI
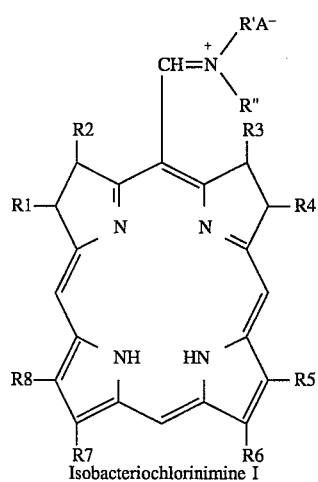
Isobacteriochlorinimine I
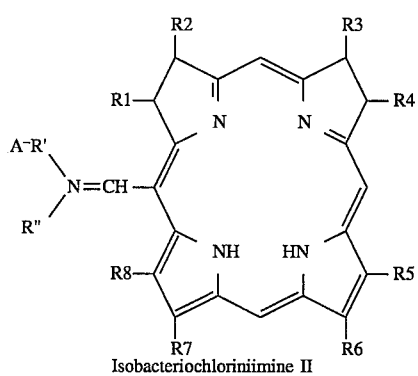
Isobacteriochloriniimine II

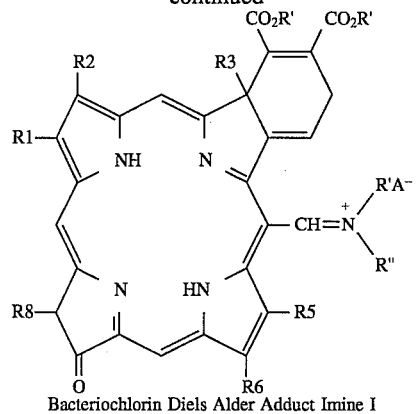
Bacteriochlorin Diels Alder Adduct Imine I
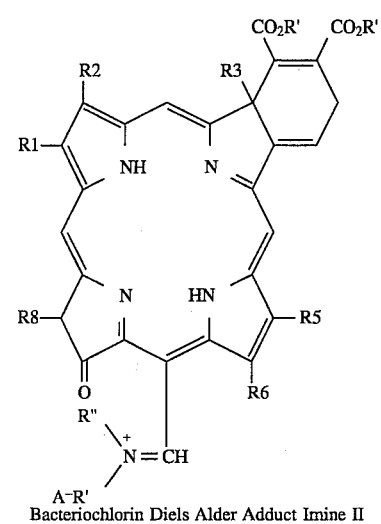
Bacteriochlorin Diels Alder Adduct Imine II
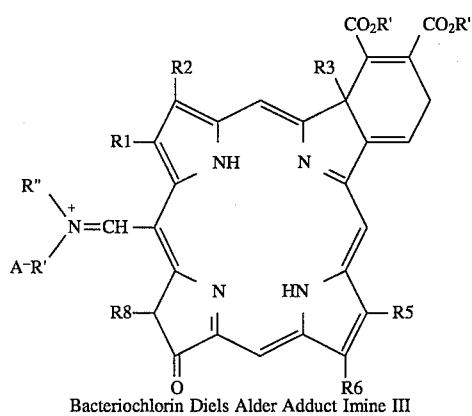
Bacteriochlorin Diels Alder Adduct Imine III
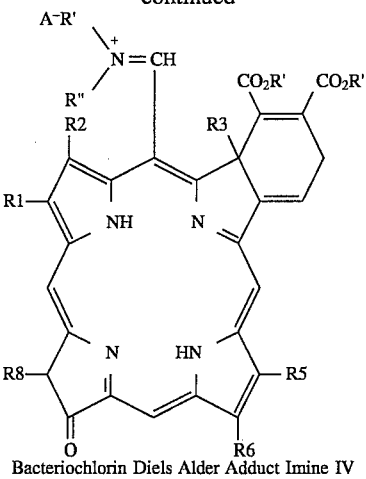
Bacteriochlorin Diels Alder Adduct Imine IV
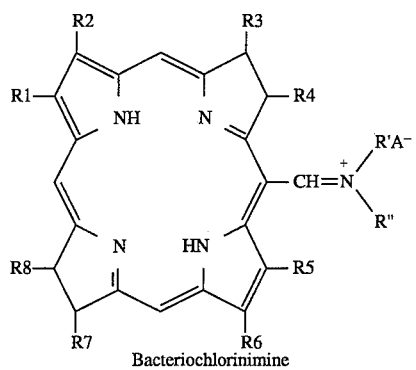
Bacteriochlorinimine
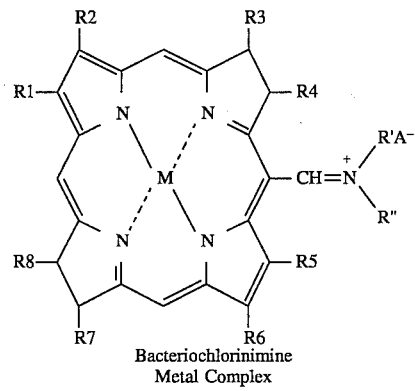
Bacteriochlorinimine Metal Complex
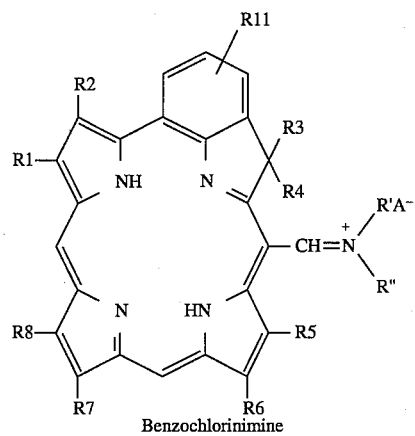
Benzochlorinimine

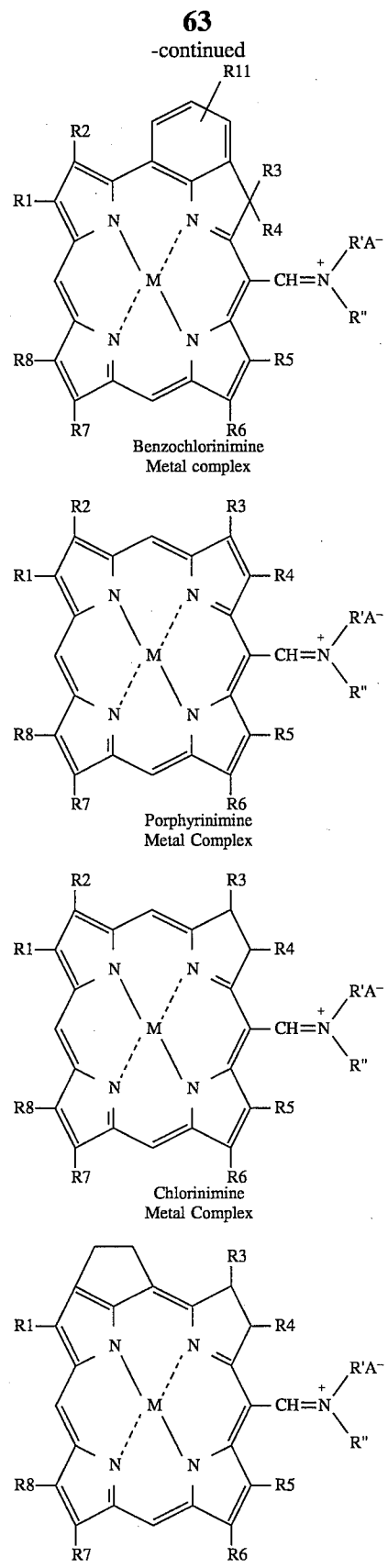
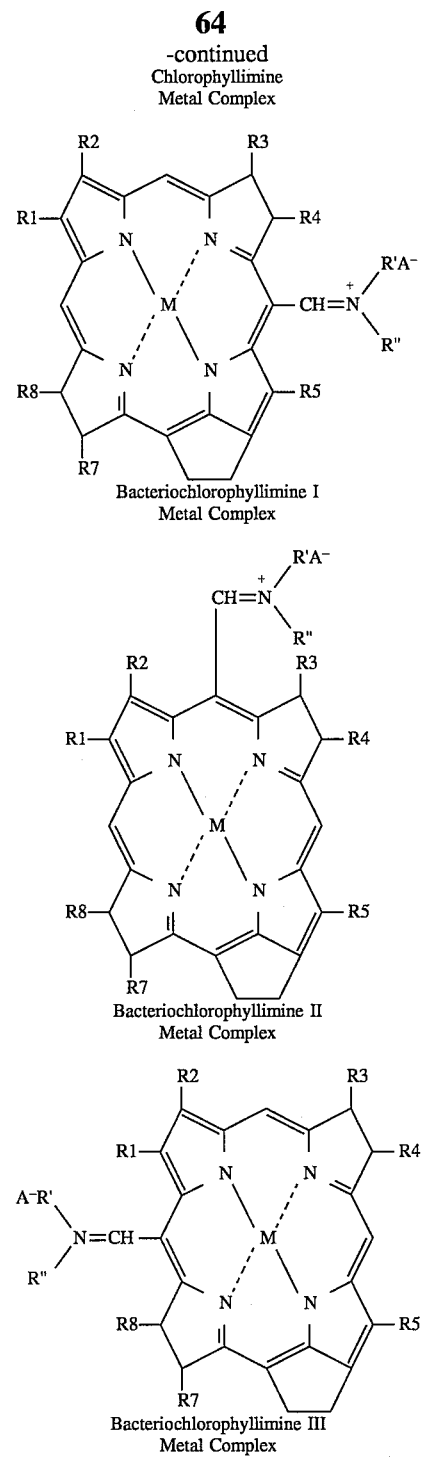

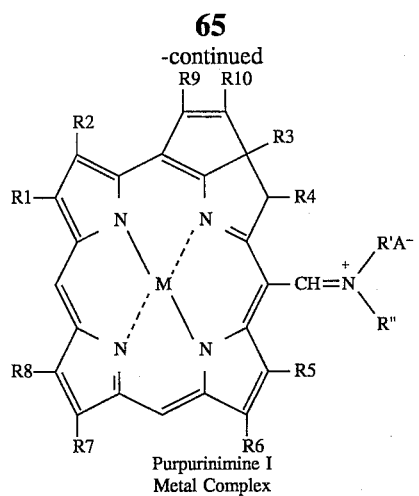
Purpurinimine I
Metal Complex
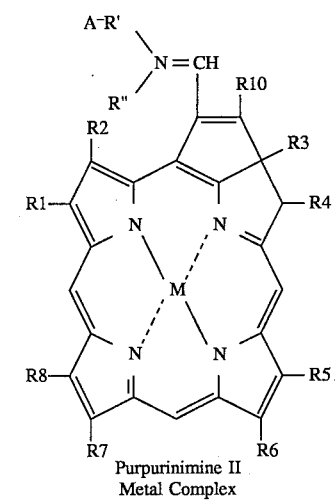
Purpurinimine II
Metal Complex
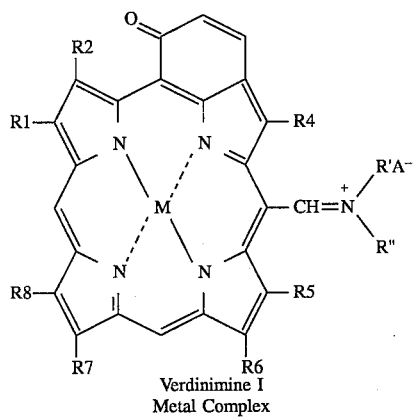
Verdinimine I
Metal Complex
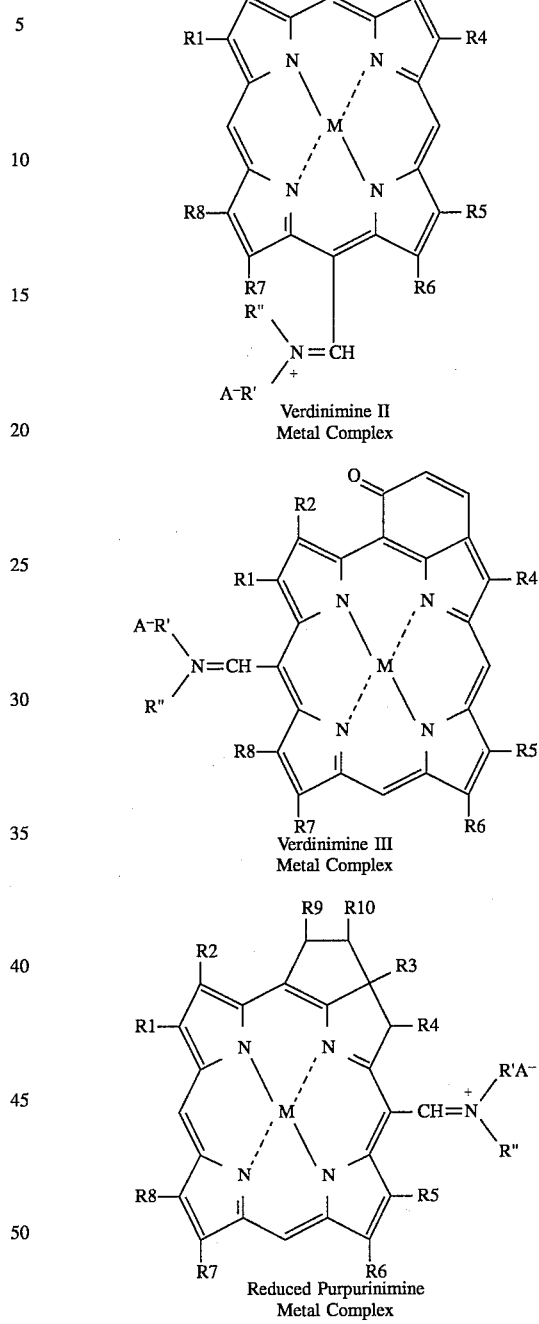

-continued
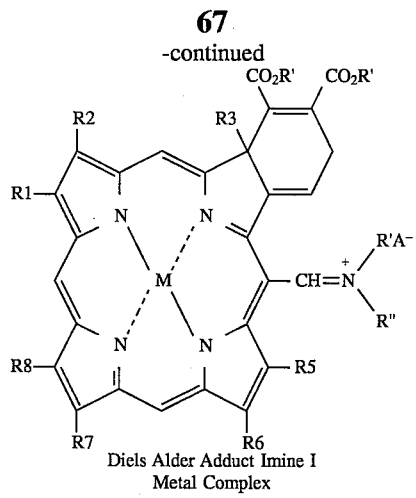
Diels Alder Adduct Imine I
Metal Complex
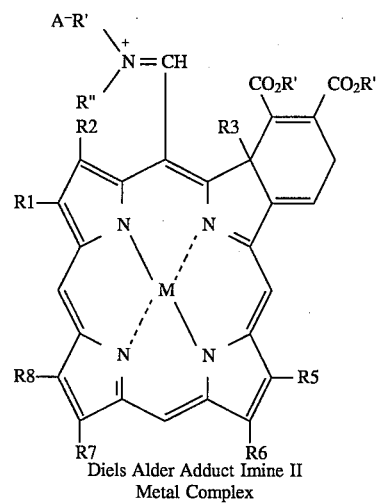
Diels Alder Adduct Imine II
Metal Complex
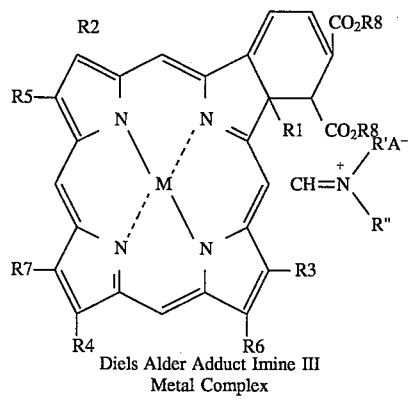
Diels Alder Adduct Imine III
Metal Complex
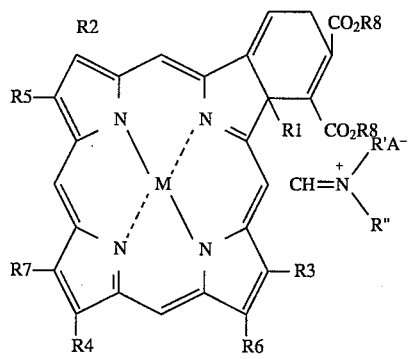
-continued
Diels Alder Adduct Imine IV
Metal Complex
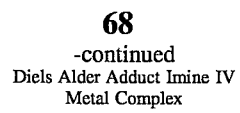
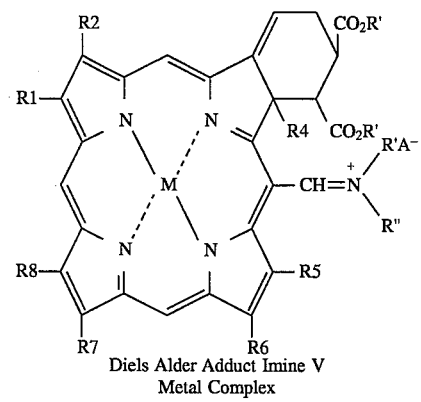
Diels Alder Adduct Imine V
Metal Complex
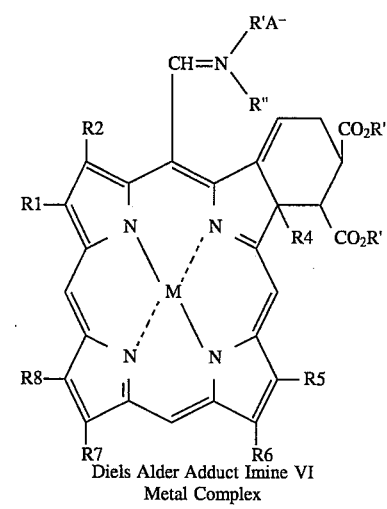
Diels Alder Adduct Imine VI
Metal Complex
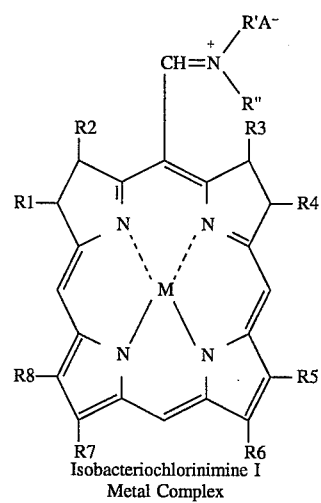
Isobacteriochlorinimine I
Metal Complex

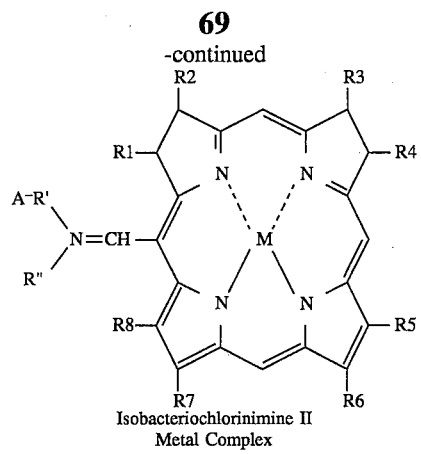

Isobacteriochlorinimine II
Metal Complex

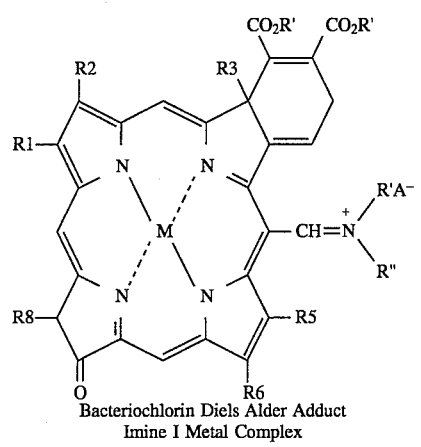

Bacteriochlorin Diels Alder Adduct
Imine I Metal Complex

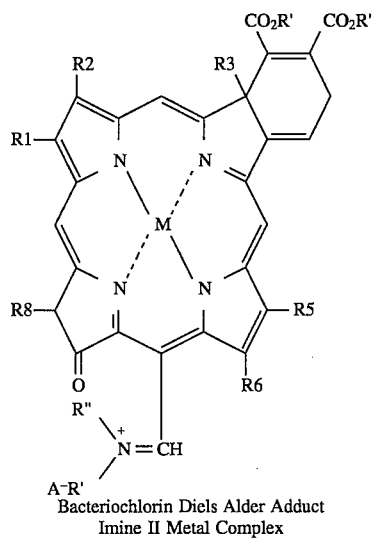

Bacteriochlorin Diels Alder Adduct
Imine II Metal Complex

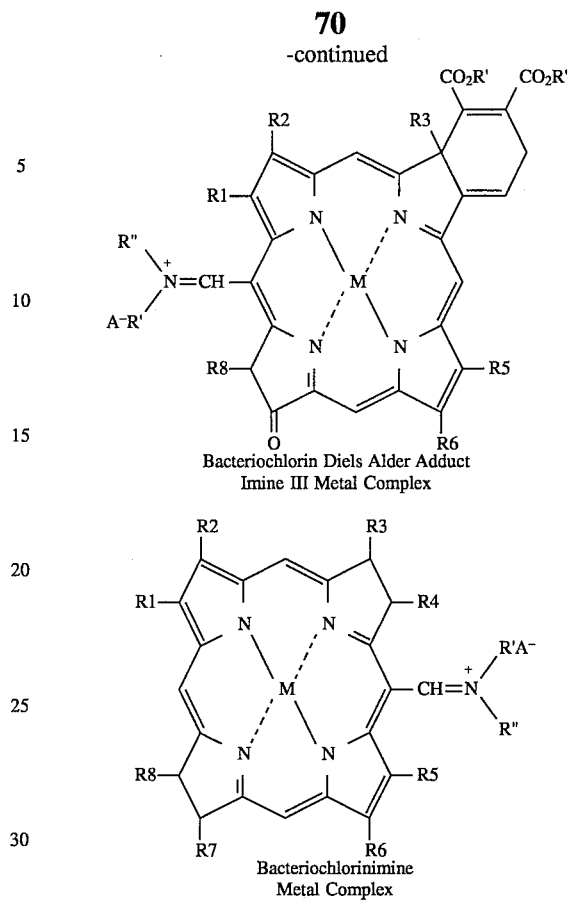

Bacteriochlorin Diels Alder Adduct
Imine III Metal Complex

Bacteriochlorinimine
Metal Complex wherein

M comprises a metal cation that is complexed with two of the nitrogens of the benzochlorin and is Ag, Al, Ce, Co, Cr, Cu, Dy, Er, Eu, Fe, Ga, Gd, Hf, Ho, In, La, Lu, Mn, Mo, Nd, Pb, Pd, Pr, Pt, Rh, Sb, Sc, Sm, Sn, Tb, $^{99m}$Tc, Th, Ti, Tl, Tm, U, V, Y, Yb, Zn or Zr, A is a physiologically acceptable anion, R' and R" can be the same or different, and each is hydrogen or an alkyl group having from one to four carbon atoms, and each of R1 through R11 is H or CHO, an alkyl group other than t-butyl having from 1 to 4 atoms, an alkylene group having from 2 to 4 carbon atoms, a group having the formula $R_3N(R_4)_3$ A where $R_3$ is a bivalent aliphatic hydrocarbon radical having from 1 to 4 carbon atoms, wherein any carbon to carbon bond is either a single or a double bond, and not more than one is a double bond; $R_4$ is hydrogen or an alkyl radical having 1 to 2 carbon atoms and the two $R_4$ groups can be the same or different, a group having the formula $R_3N(R_5)_3$ A where $R_3$ is a bivalent hydrocarbon radical having from 1 to 4 carbon atoms, wherein any carbon to carbon bond is either a single or a double bond, and not more than one is a double bond; A is a physiologically acceptable anion and $R_5$ is an alkyl group having from 1 to 2 carbon atoms and the three $R_5$ groups can be the same or different.

a group having the formula $R_3OH$ where $R_3$ is a bivalent aliphatic hydrocarbon radical having from 1 to 4 carbon atoms, wherein any carbon to carbon bond is either a single or a double bond, and not more than one is a double bond, or $CO_2R'$, $CH_2CO_2R'$ or $CH_2CH_2CO_2R'$ where R' is H, or an alkyl group other than t-butyl having from one to four carbon atoms, with the provisos that R11 can be $SO_3H$ or a salt thereof, that, in the foregoing chlorinimines and metal complexes, either R3 or R4 can be a $CH_2$ group or O which, in either case, is bonded to the carbon of the pyrrole ring by a double bond, that, in the foregoing families of compounds which are designated Isobacteriochlorinimines I and Isobacteriochlorinimines II and their metal complexes, either R1 or R2 can be a CH2 group or O which, in either case, is bonded to the carbon of the pyrrole ring by a double bond and, when either R1 or R2 is a $CH_2$ group or O, either R3 or R4 is also a $CH_2$ group or O which is bonded to the carbon of the pyrrole ring by and double bond, and that in the foregoing families of compounds which are designated bacteriochlorinimines and metal complexes, either R3 or R4 can be a $CH_2$ group or O which, in either case, is bonded to the carbon of the pyrrole ring by a double bond and, when either R3 or R4 is a $CH_2$ group or O, either R7 or R8 is also a $CH_2$ group or O which is bonded to the carbon of the pyrrole ring by and double bond.

11. A method of treating topical skin conditions using photodynamic therapy with a composition of matter, a purified imine of a porphyrin, a chlorin, a bacteriochlorin, a chlorophyll, a bacteriochlorophyll, a purpurin, a reduced purpurin, a verdin, a Diels Alder adduct, an isobacteriochlorin, a benzochlorin or a metal complex of one of the foregoing imines having one of the structures set forth below, and identified by legend:

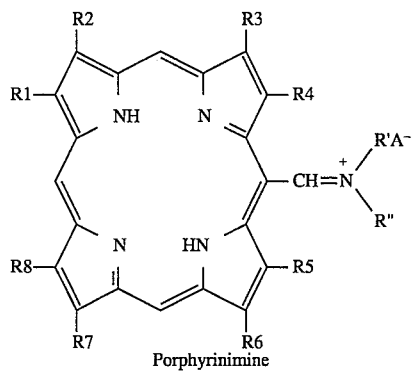
Porphyrinimine

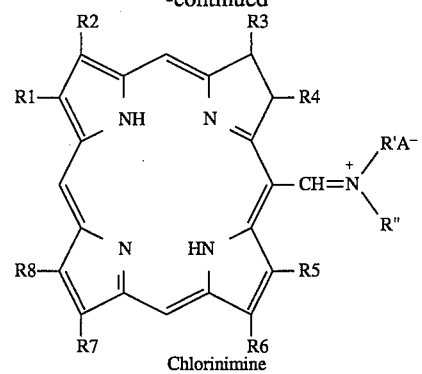
Chlorinimine

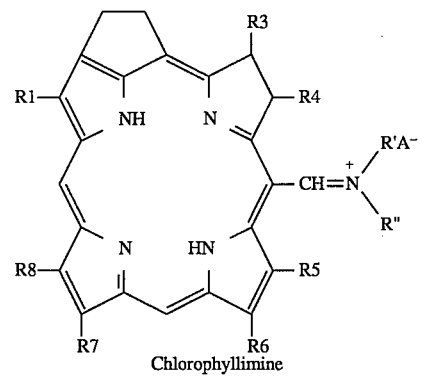
Chlorophyllimine

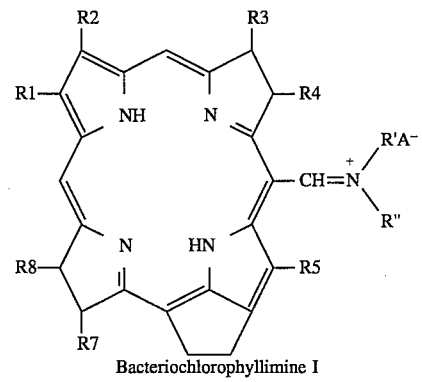
Bacteriochlorophyllimine I

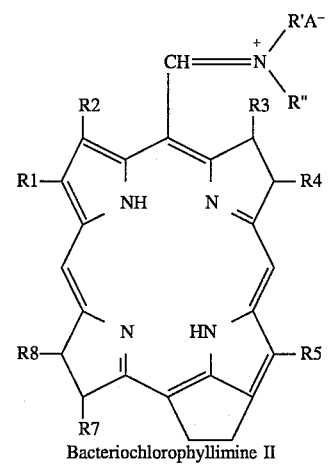
Bacteriochlorophyllimine II

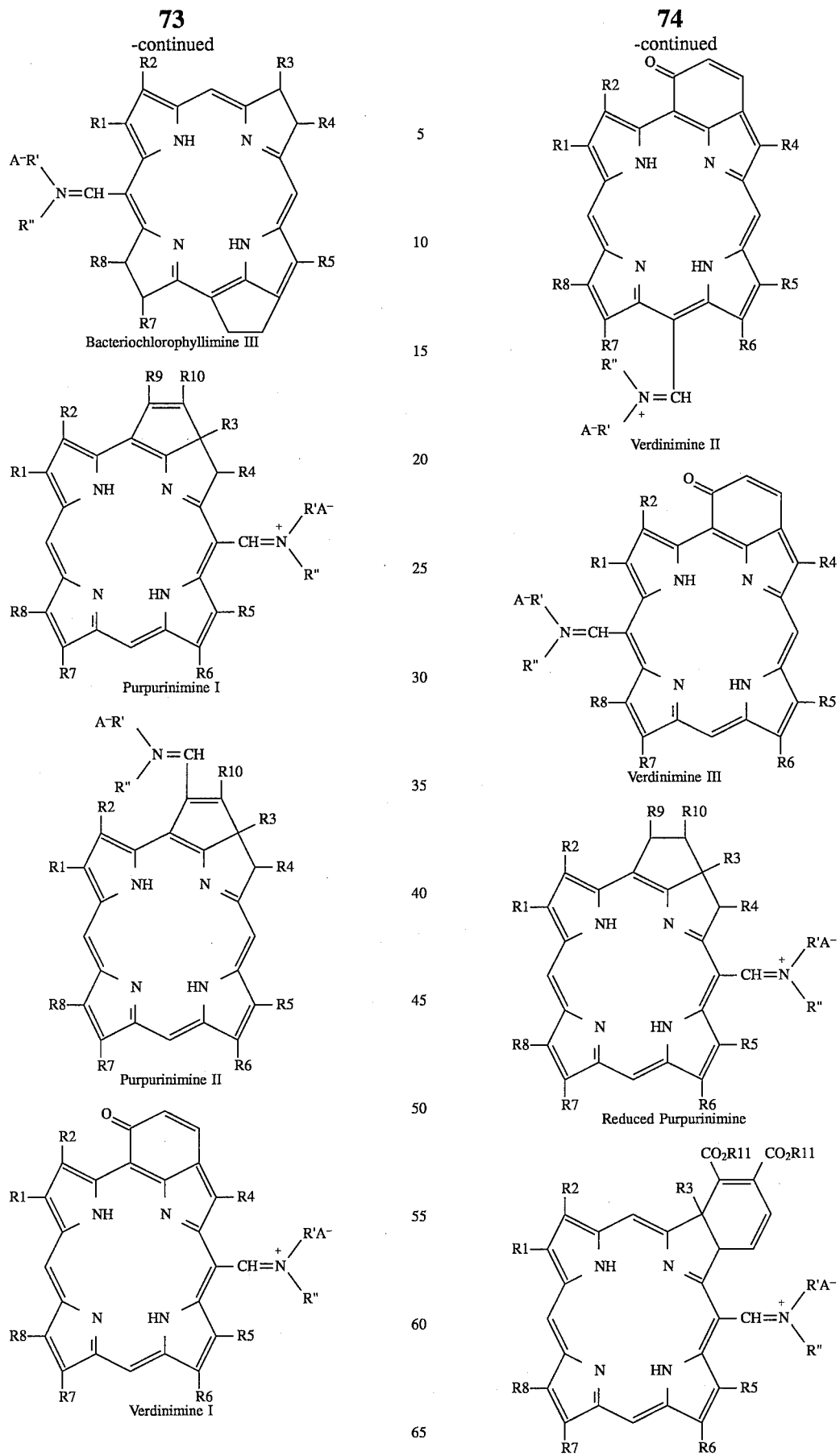

-continued
Diels Alder Adduct Imine I
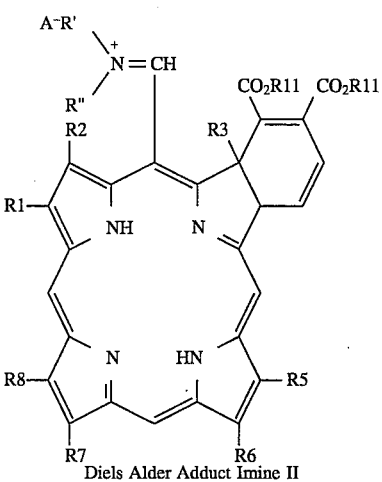
Diels Alder Adduct Imine II
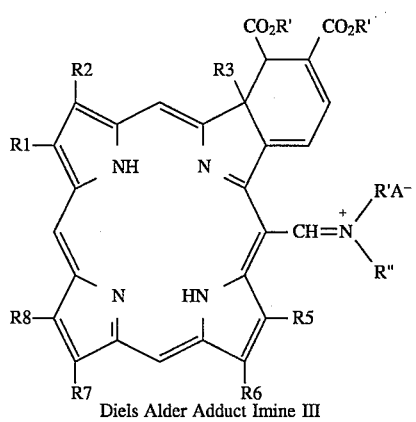
Diels Alder Adduct Imine III
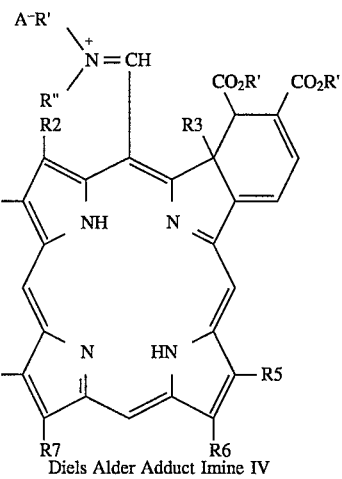
Diels Alder Adduct Imine IV
-continued
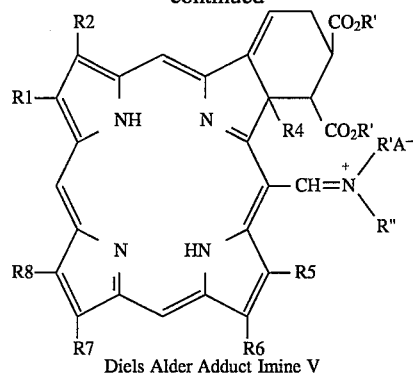
Diels Alder Adduct Imine V
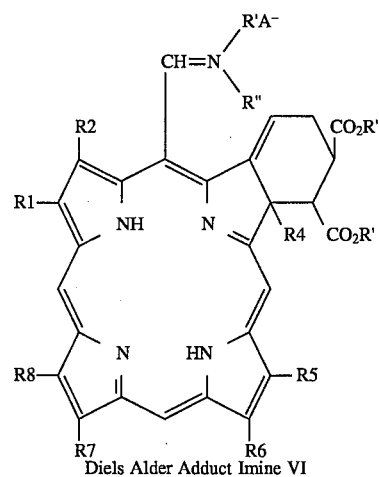
Diels Alder Adduct Imine VI
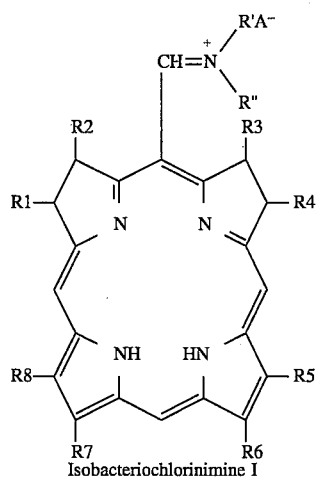
Isobacteriochlorinimine I
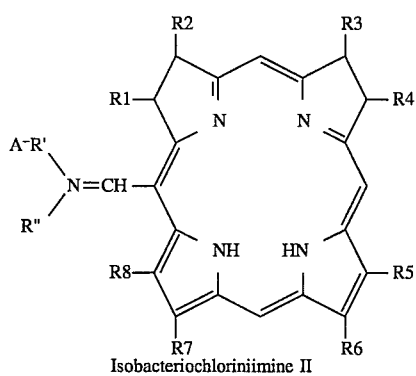
Isobacteriochloriniimine II

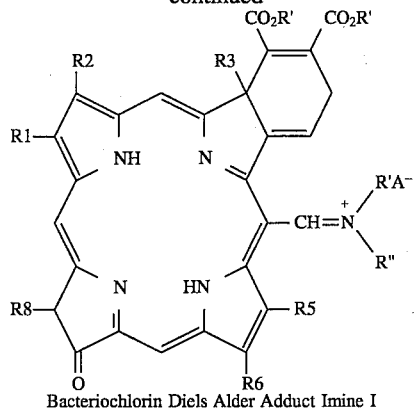
Bacteriochlorin Diels Alder Adduct Imine I
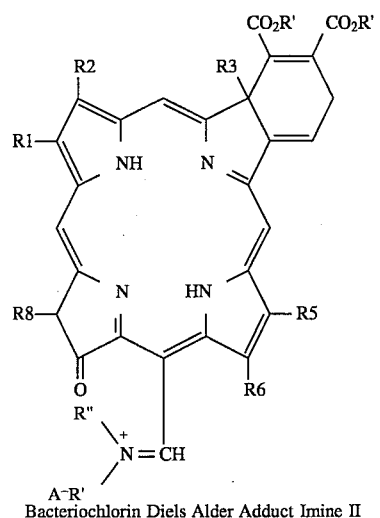
Bacteriochlorin Diels Alder Adduct Imine II
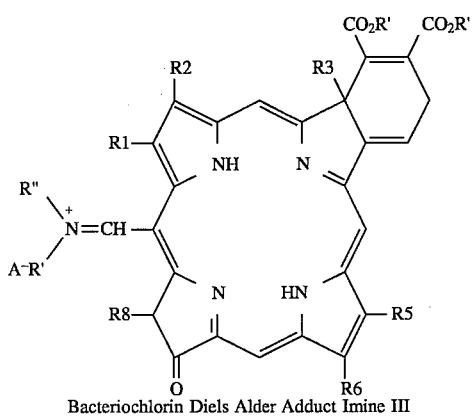
Bacteriochlorin Diels Alder Adduct Imine III
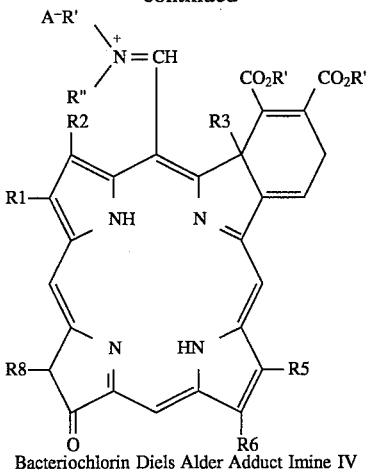
Bacteriochlorin Diels Alder Adduct Imine IV
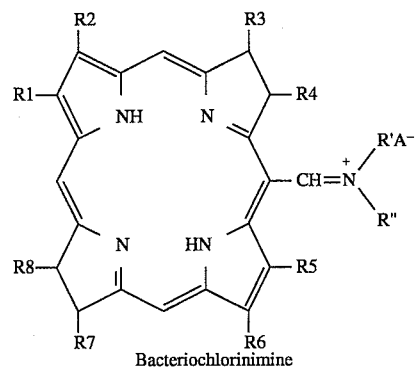
Bacteriochlorinimine
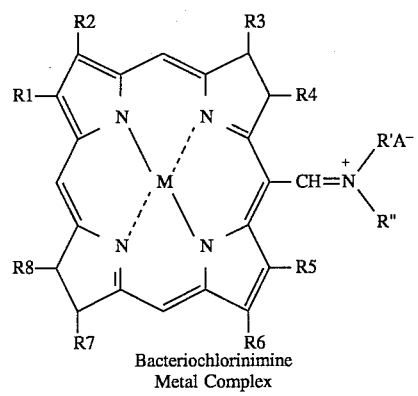
Bacteriochlorinimine Metal Complex
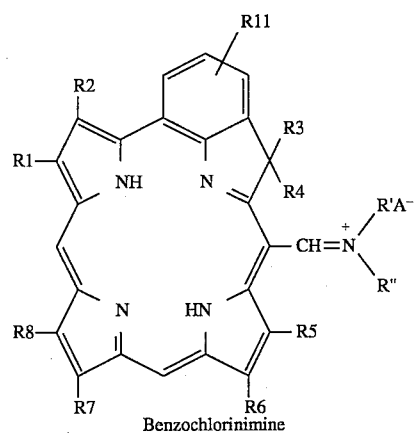
Benzochlorinimine

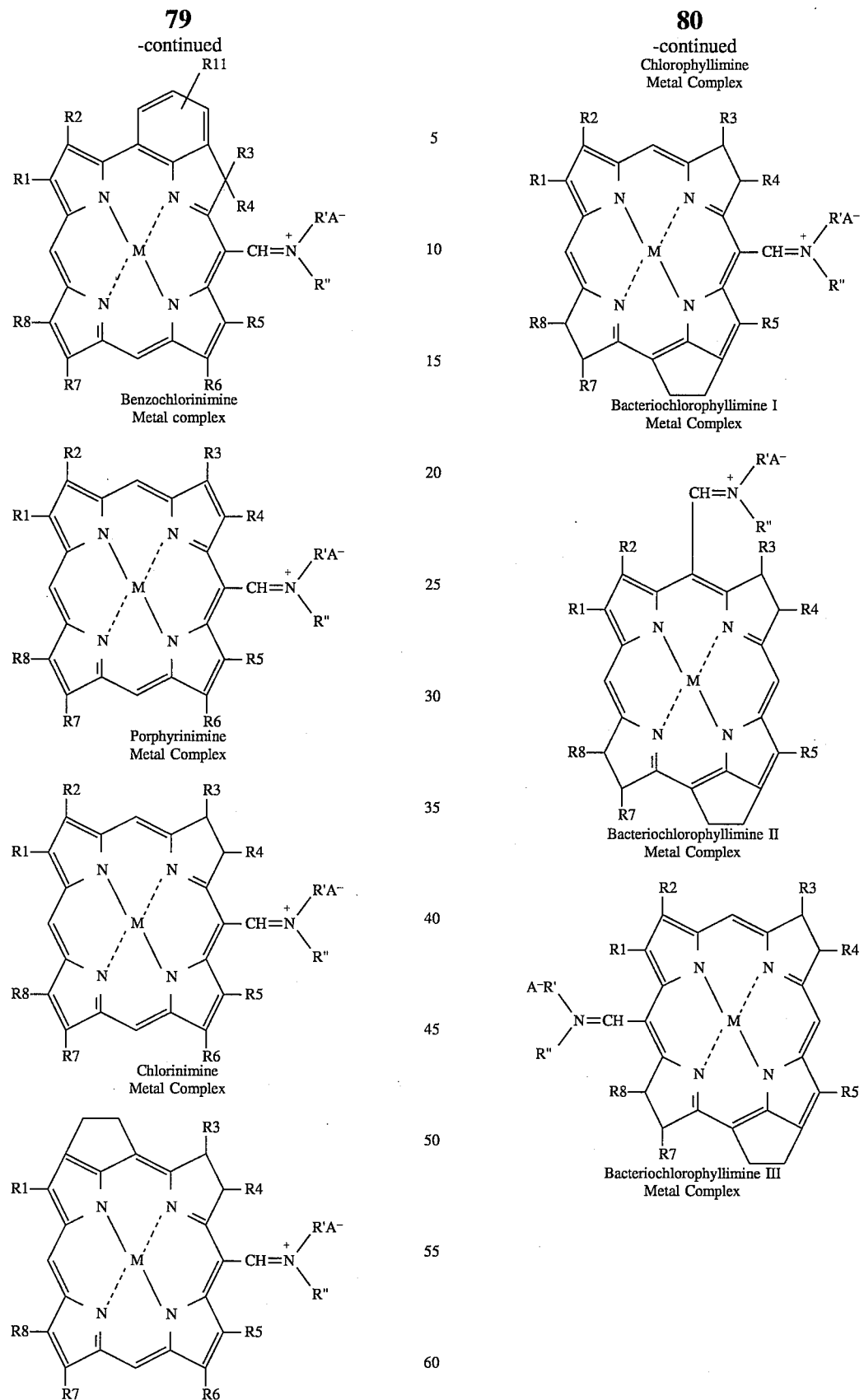

81
-continued
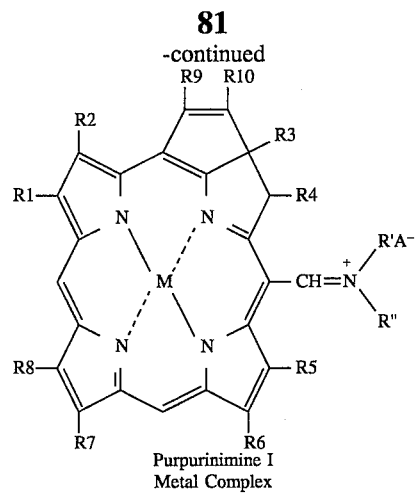
Purpurinimine I
Metal Complex
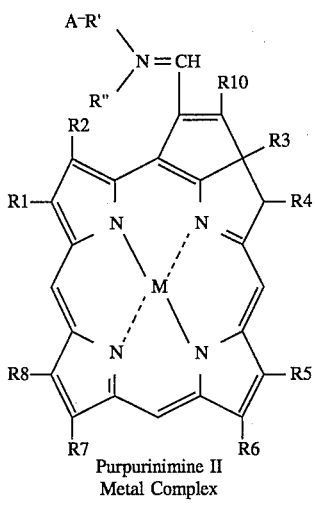
Purpurinimine II
Metal Complex
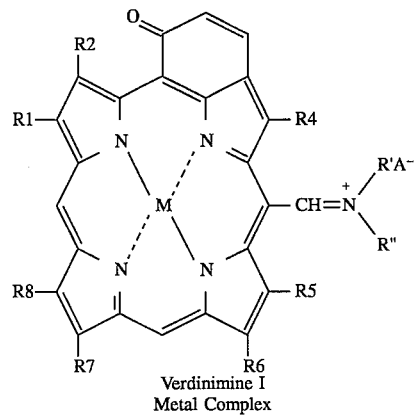
Verdinimine I
Metal Complex
82
-continued
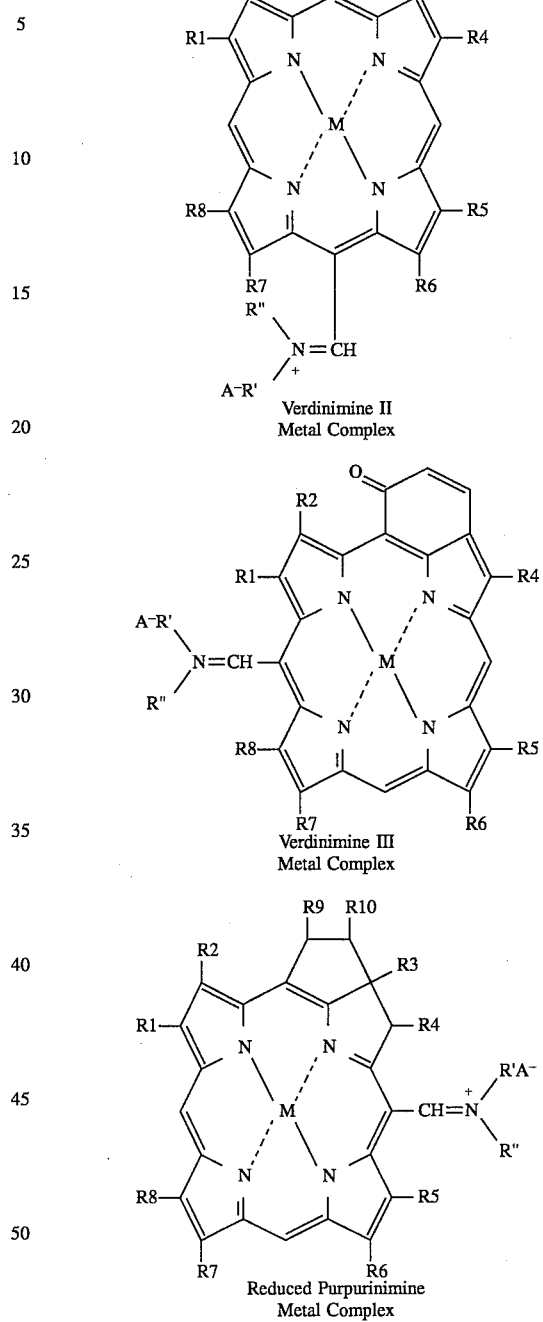
Verdinimine II
Metal Complex
Verdinimine III
Metal Complex
Reduced Purpurinimine
Metal Complex

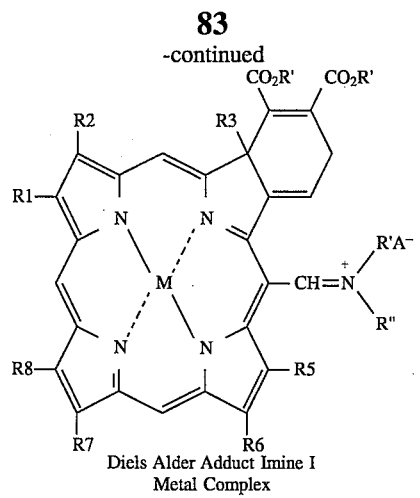
Diels Alder Adduct Imine I
Metal Complex
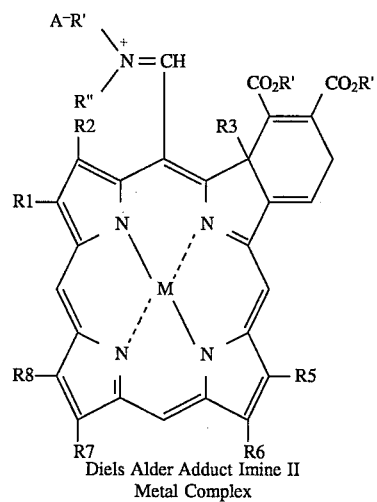
Diels Alder Adduct Imine II
Metal Complex
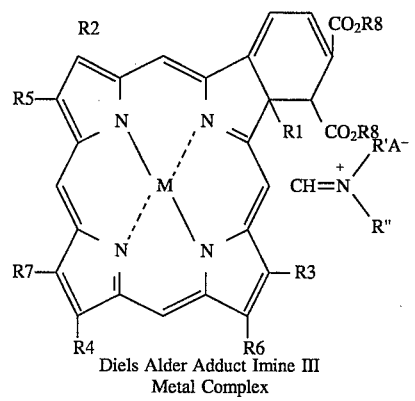
Diels Alder Adduct Imine III
Metal Complex
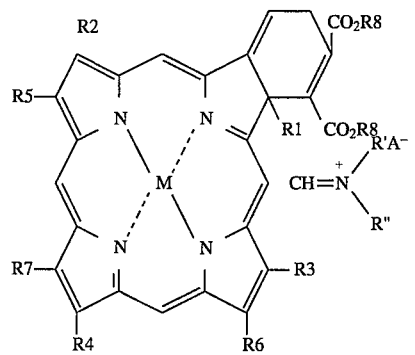
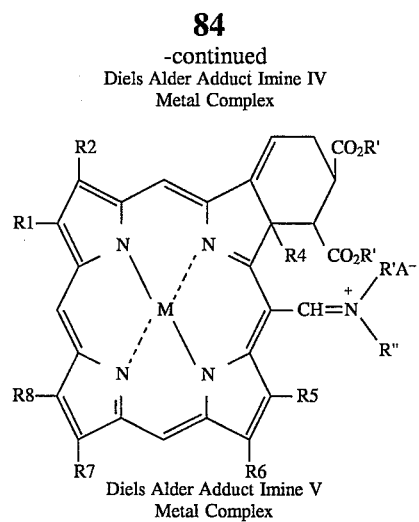
-continued
Diels Alder Adduct Imine IV
Metal Complex
Diels Alder Adduct Imine V
Metal Complex
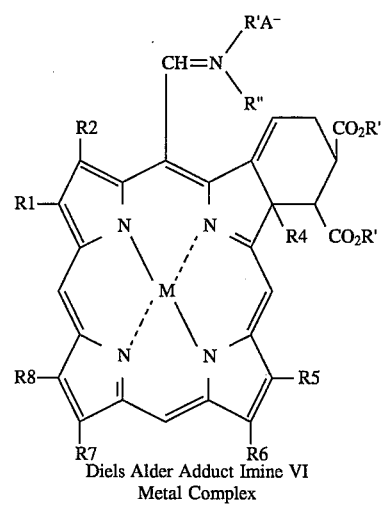
Diels Alder Adduct Imine VI
Metal Complex
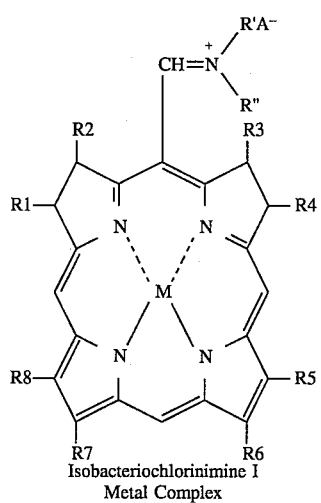
Isobacteriochlorinimine I
Metal Complex

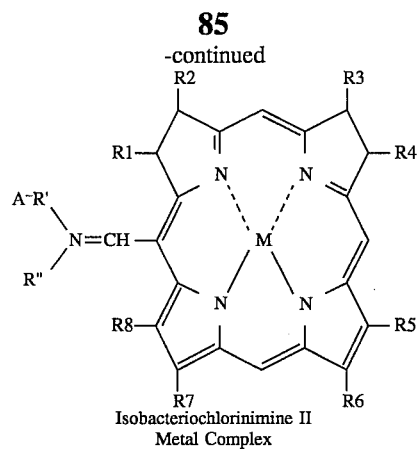

Isobacteriochlorinimine II
Metal Complex

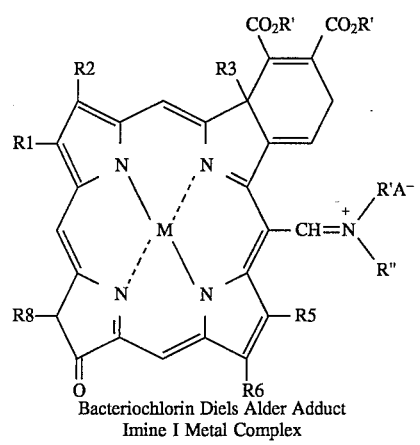

Bacteriochlorin Diels Alder Adduct
Imine I Metal Complex

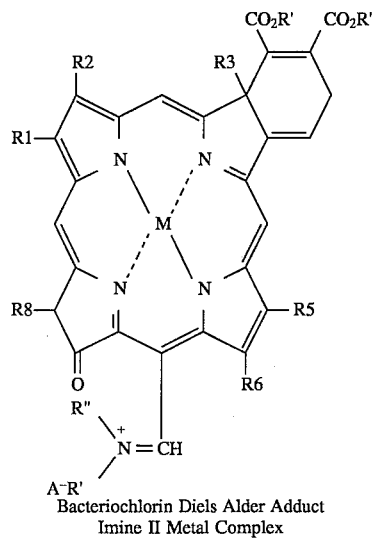

Bacteriochlorin Diels Alder Adduct
Imine II Metal Complex

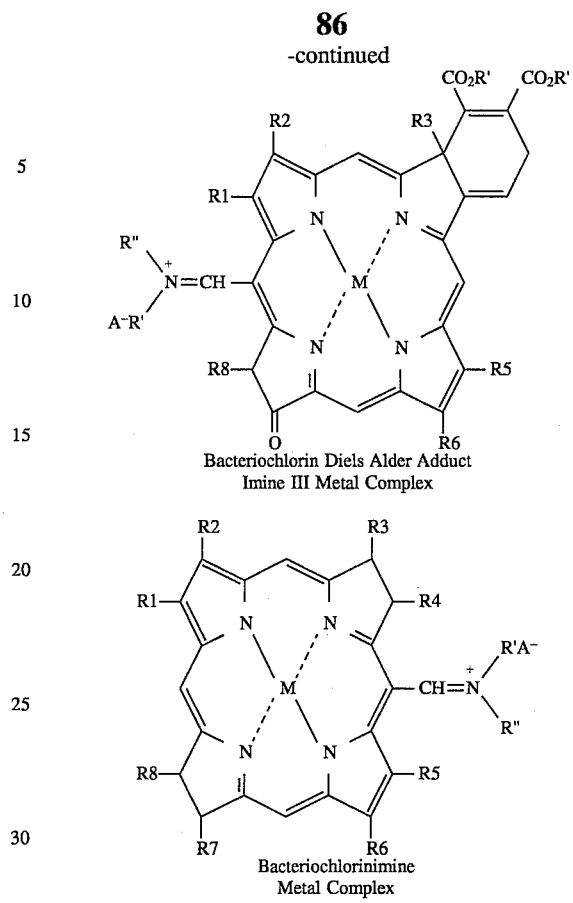

Bacteriochlorin Diels Alder Adduct
Imine III Metal Complex

Bacteriochlorinimine
Metal Complex wherein

M comprises a metal cation that is complexed with two of the nitrogens of the benzochlorin and is Ag, Al, Ce, Co, Cr, Cu, Dy, Er, Eu, Fe, Ga, Gd, Hf, Ho, In, La, Lu, Mn, Mo, Nd, Pb, Pd, Pr, Pt, Rh, Sb, Sc, Sm, Sn, Tb, $^{99m}$Tc, Th, Ti, Tl, Tm, U, V, Y, Yb, Zn or Zr, A is a physiologically acceptable anion, R' and R" can be the same or different, and each is hydrogen or an alkyl group having from one to four carbon atoms, and each of R1 through R11 is H or CHO, an alkyl group other than t-butyl having from 1 to 4 atoms, an alkylene group having from 2 to 4 carbon atoms, a group having the formula $R_3N(R_4)_3$ A where $R_3$ is a bivalent aliphatic hydrocarbon radical having from 1 to 4 carbon atoms, wherein any carbon to carbon bond is either a single or a double bond, and not more than one is a double bond; $R_4$ is hydrogen or an alkyl radical having 1 to 2 carbon atoms and the two $R_4$ groups can be the same or different, a group having the formula $R_3N(R_5)_3$ A where $R_3$ is a bivalent hydrocarbon radical having from 1 to 4 carbon atoms, wherein any carbon to carbon bond is either a single or a double bond, and not more than one is a double bond; A is a physiologically acceptable anion and $R_5$ is an alkyl group having from 1 to 2 carbon atoms and the three $R_5$ groups can be the same or different, a group having the formula $R_3OH$ where $R_3$ is a bivalent aliphatic hydrocarbon radical having from 1 to 4 carbon atoms, wherein any carbon to carbon bond is either a single or a double bond, and not more than one is a double bond, or $CO_2R'$, $CH_2CO_2R'$ or $CH_2CH_2CO_2R'$ where R' is H, or an alkyl group other than t-butyl having from one to four carbon atoms, with the provisos that R11 can be $SO_3H$ or a salt thereof, that, in the foregoing chlorinimines and metal complexes, either R3 or R4 can be a $CH_2$ group or O which, in either case, is bonded to the carbon of the pyrrole ring by a double bond, that, in the foregoing families of compounds which are designated Isobacteriochlorinimines I and Isobacteriochlorinimines II and their metal complexes, either R1 or R2 can be a CH2 group or O which, in either case, is bonded to the carbon of the pyrrole ring by a double bond and, when either R1 or R2 is a $CH_2$ group or O, either R3 or R4 is also a $CH_2$ group or O which is bonded to the carbon of the pyrrole ring by and double bond, and that in the foregoing families of compounds which are designated bacteriochlorinimines and metal complexes, either R3 or R4 can be a $CH_2$ group or O which, in either case, is bonded to the carbon of the pyrrole ring by a double bond and, when either R3 or R4 is a $CH_2$ group or O, either R7 or R8 is also a $CH_2$ group or O which is bonded to the carbon of the pyrrole ring by and double bond.

12. A method of sterilizing blood using photodynamic therapy with a composition of matter, a purified imine of a porphyrin, a chlorin, a bacteriochlorin, a chlorophyll, a bacteriochlorophyll, a purpurin, a reduced purpurin, a verdin, a Diels Alder adduct, an isobacteriochlorin, a benzochlorin or a metal complex of one of the foregoing imines having one of the structures set forth below, and identified by legend:

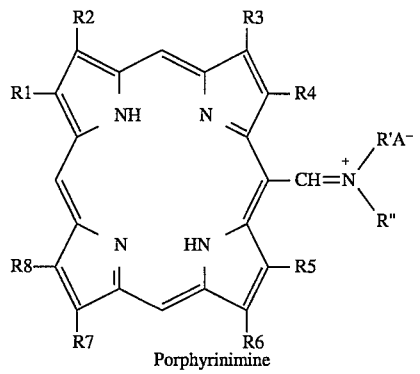
Porphyrinimine

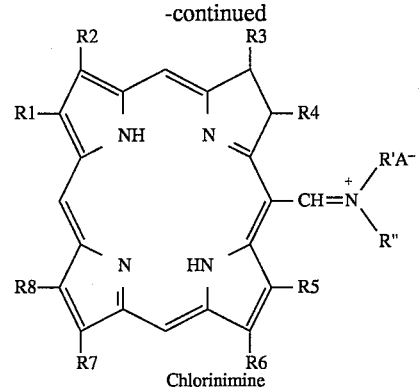
Chlorinimine

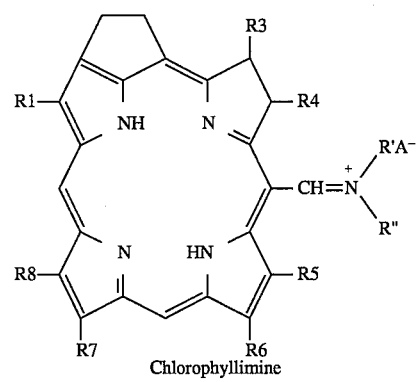
Chlorophyllimine

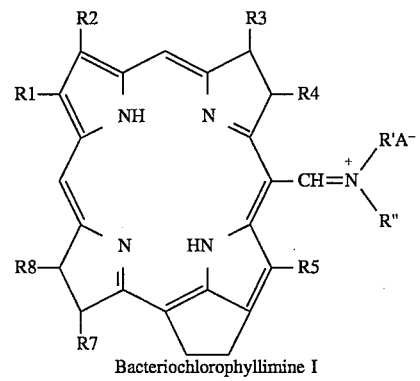
Bacteriochlorophyllimine I

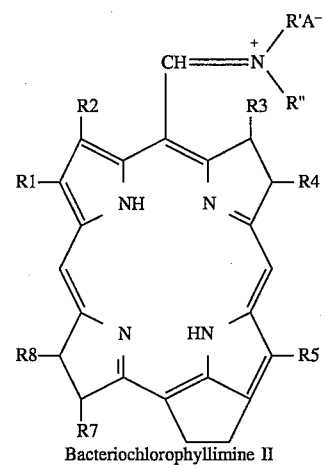
Bacteriochlorophyllimine II

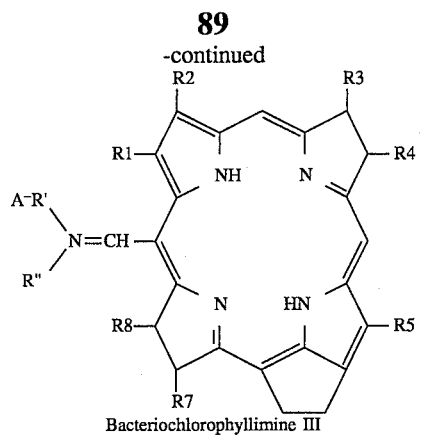
Bacteriochlorophyllimine III
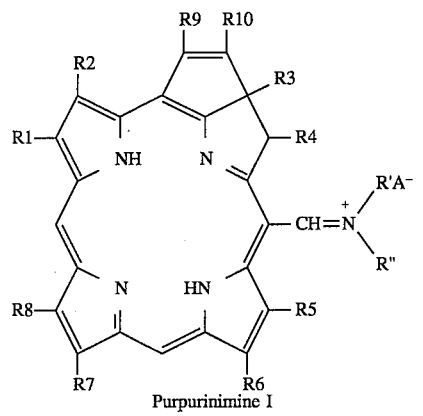
Purpurinimine I
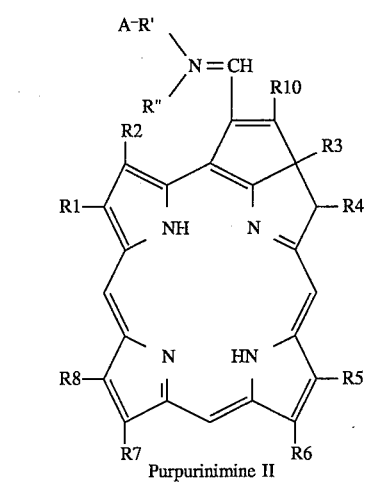
Purpurinimine II
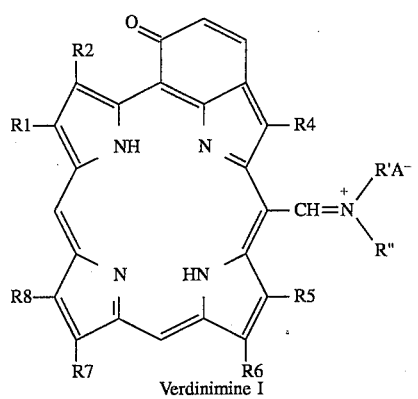
Verdinimine I
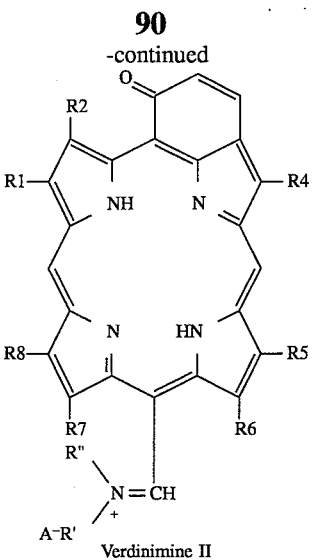
Verdinimine II
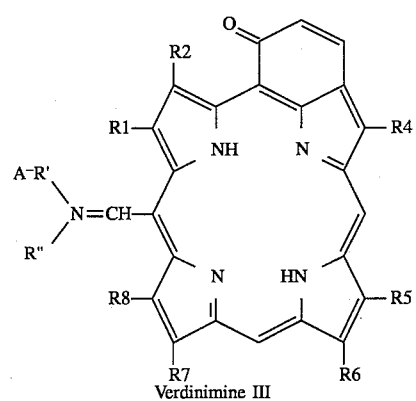
Verdinimine III
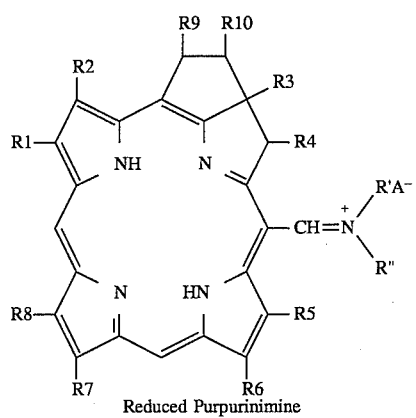
Reduced Purpurinimine
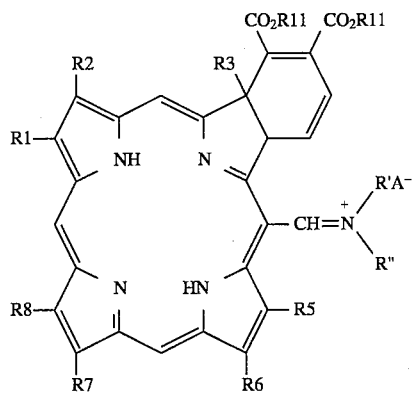

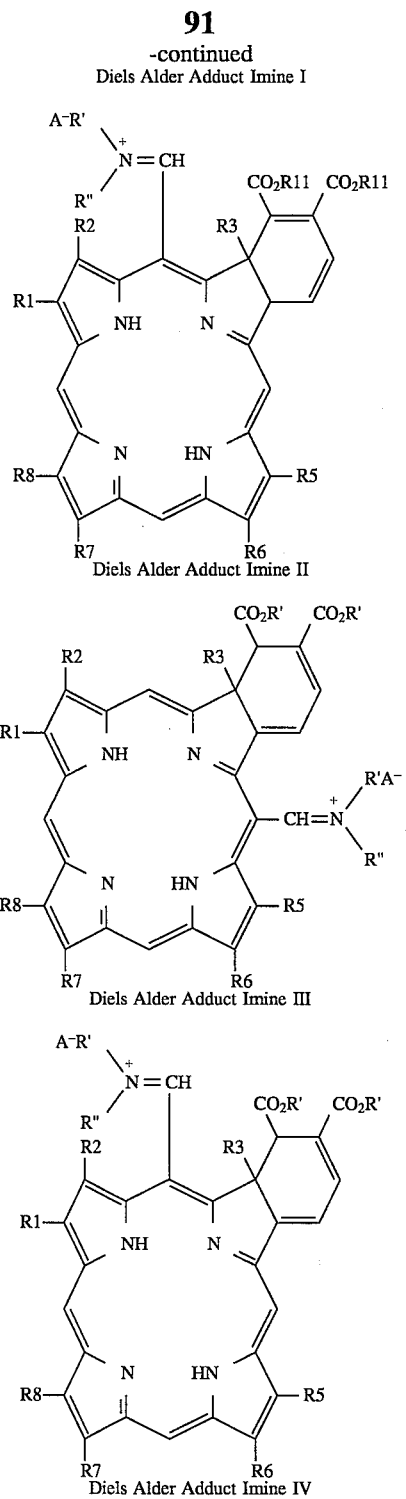
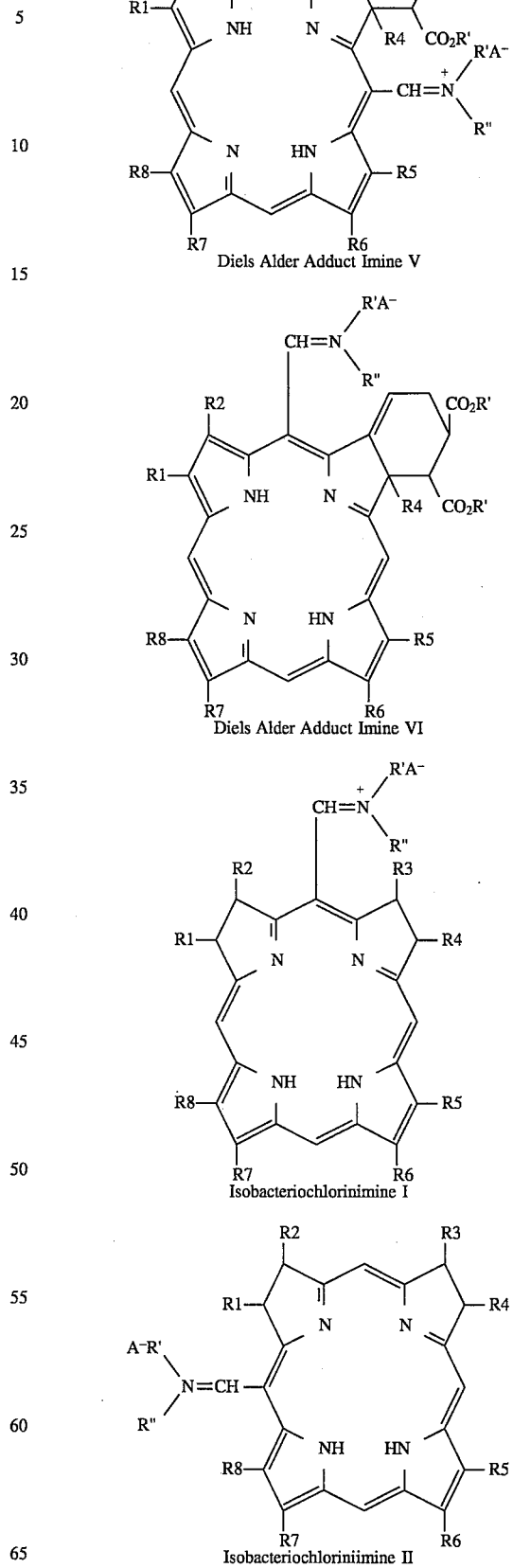

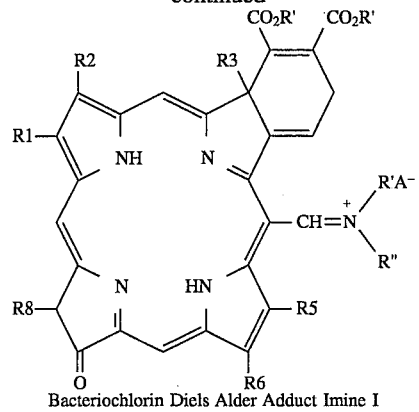
Bacteriochlorin Diels Alder Adduct Imine I
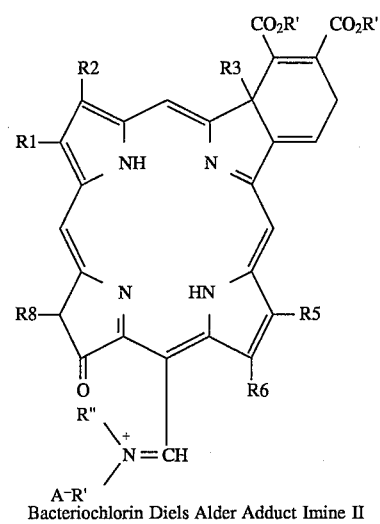
Bacteriochlorin Diels Alder Adduct Imine II
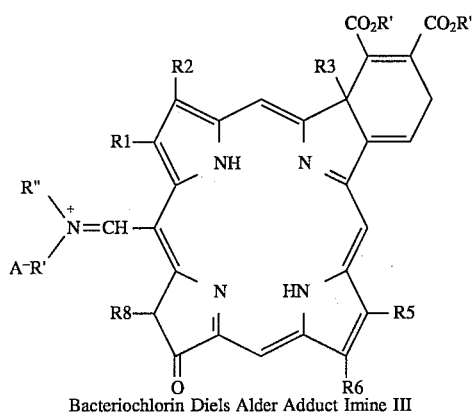
Bacteriochlorin Diels Alder Adduct Imine III
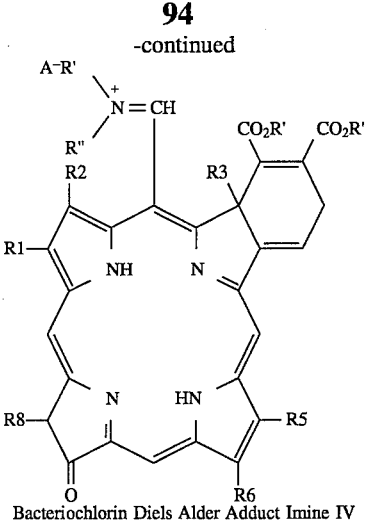
Bacteriochlorin Diels Alder Adduct Imine IV
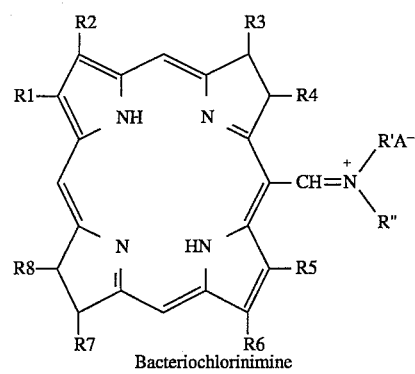
Bacteriochlorinimine
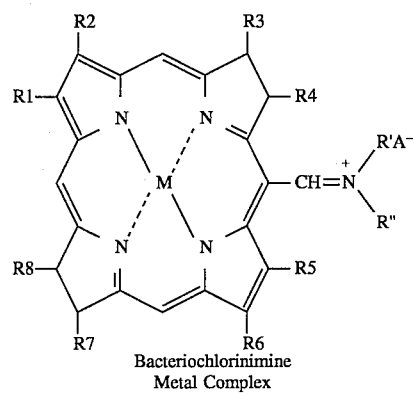
Bacteriochlorinimine Metal Complex
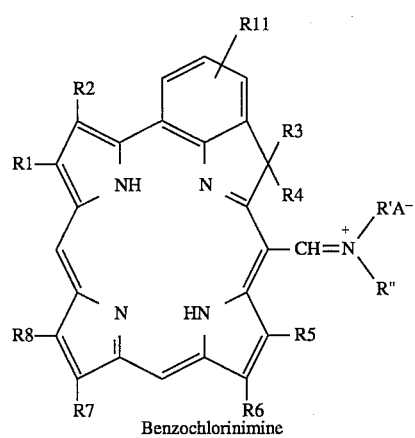
Benzochlorinimine

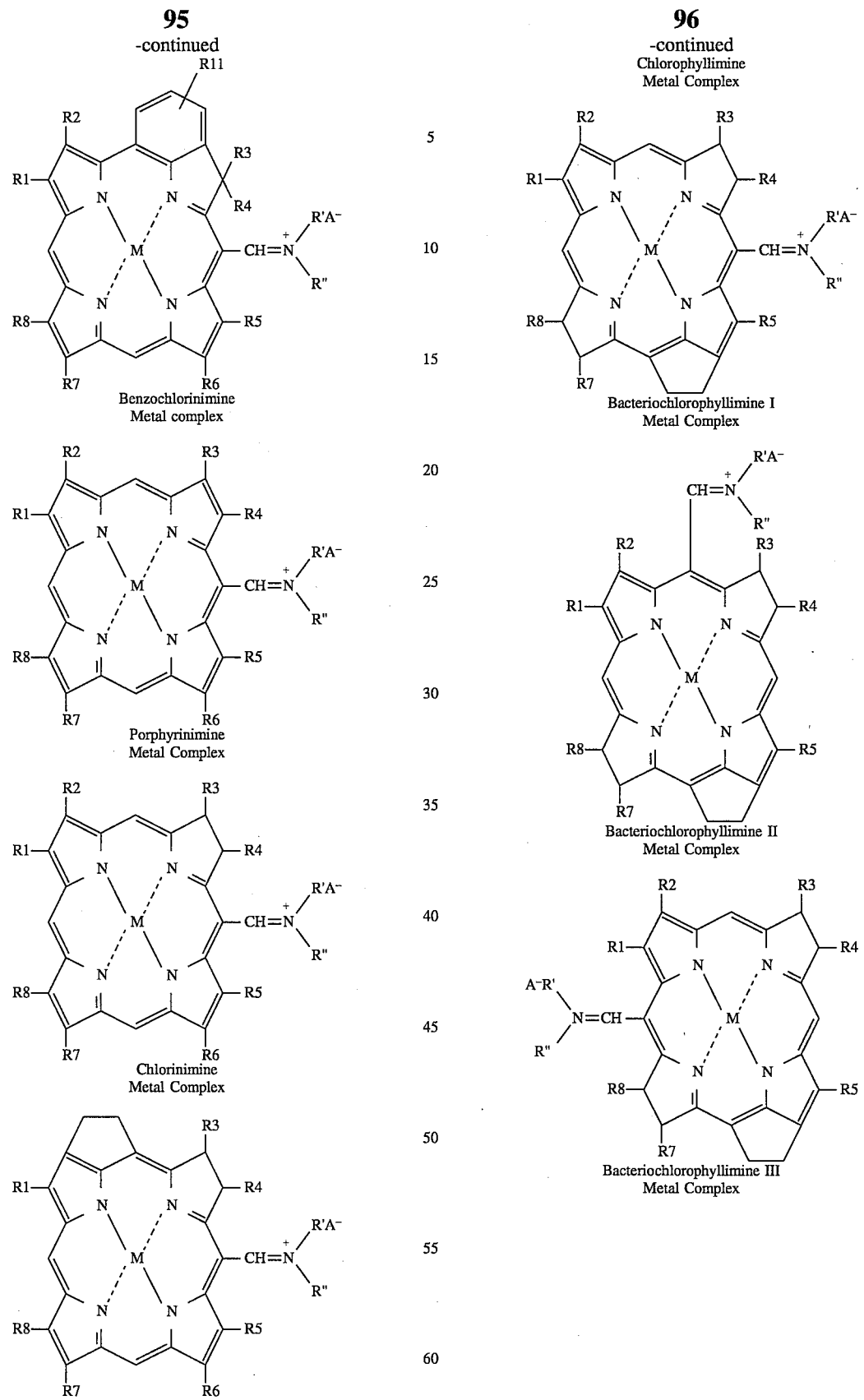

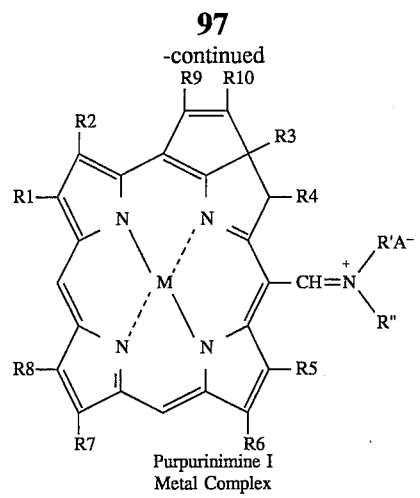
Purpurinimine I
Metal Complex
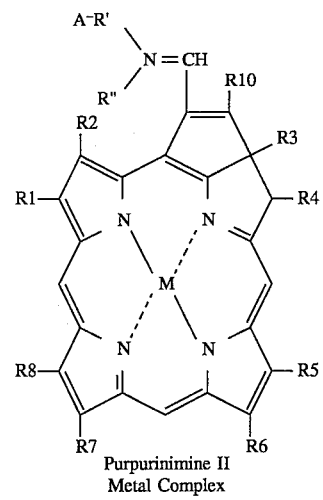
Purpurinimine II
Metal Complex
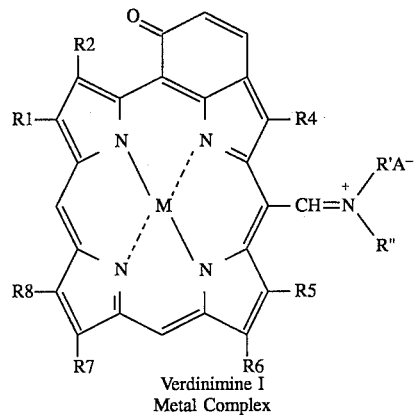
Verdinimine I
Metal Complex
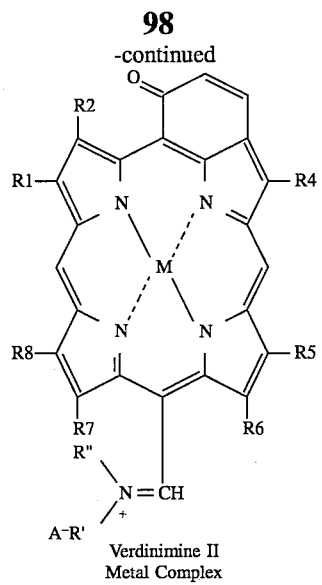
Verdinimine II
Metal Complex
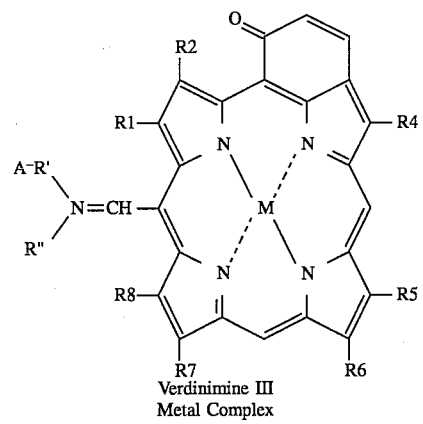
Verdinimine III
Metal Complex
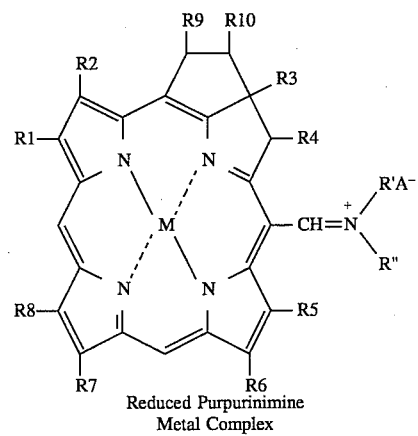
Reduced Purpurinimine
Metal Complex

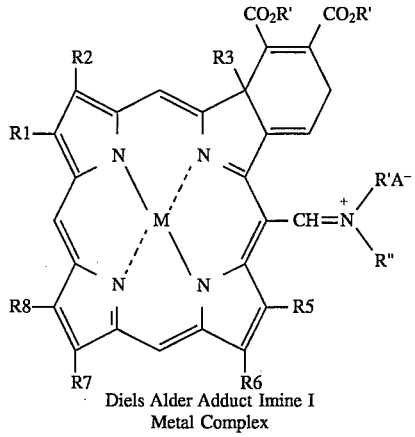
Diels Alder Adduct Imine I
Metal Complex
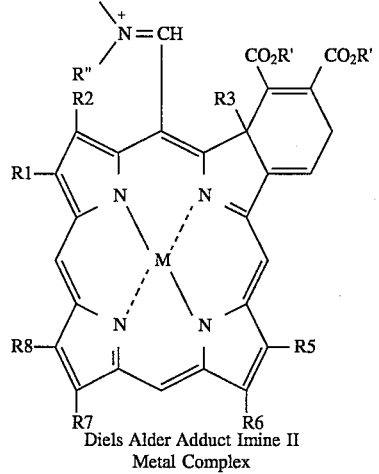
Diels Alder Adduct Imine II
Metal Complex
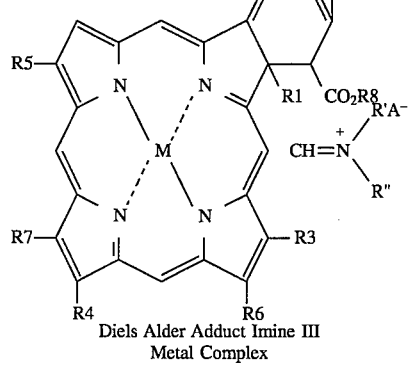
Diels Alder Adduct Imine III
Metal Complex
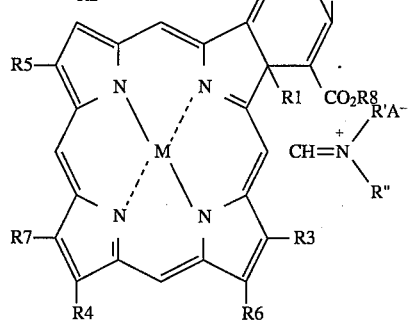
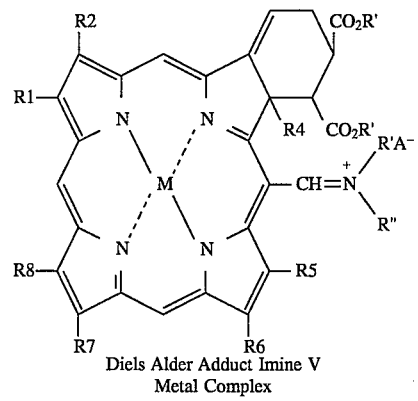
Diels Alder Adduct Imine IV
Metal Complex
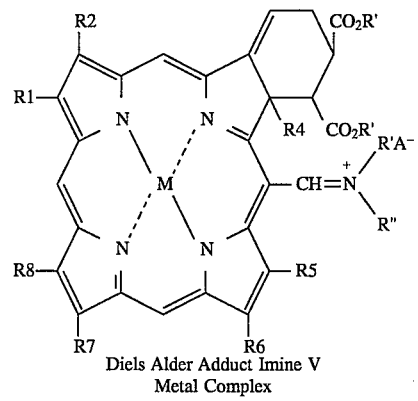
Diels Alder Adduct Imine V
Metal Complex
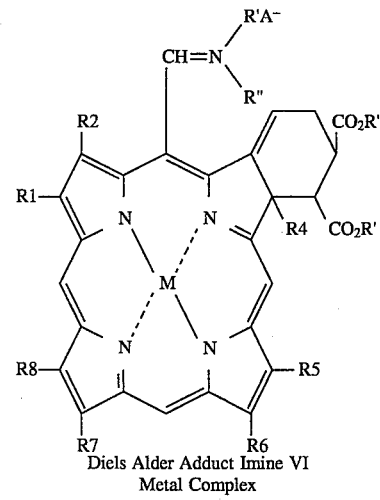
Diels Alder Adduct Imine VI
Metal Complex
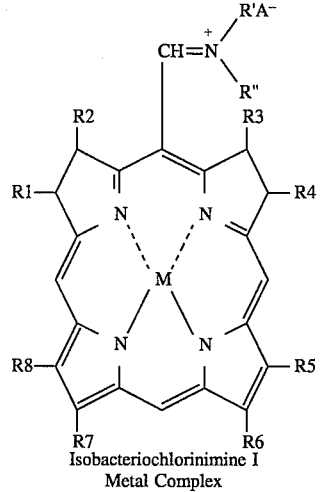
Isobacteriochlorinimine I
Metal Complex

101
-continued

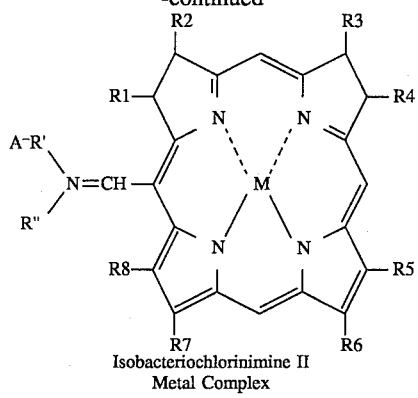

Isobacteriochlorinimine II
Metal Complex

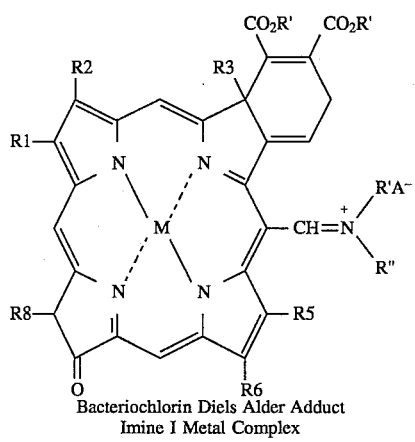

Bacteriochlorin Diels Alder Adduct
Imine I Metal Complex

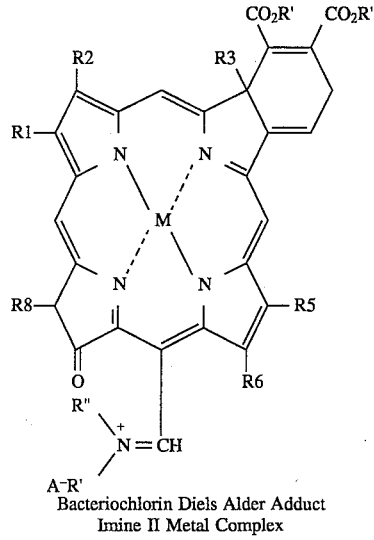

Bacteriochlorin Diels Alder Adduct
Imine II Metal Complex

102
-continued

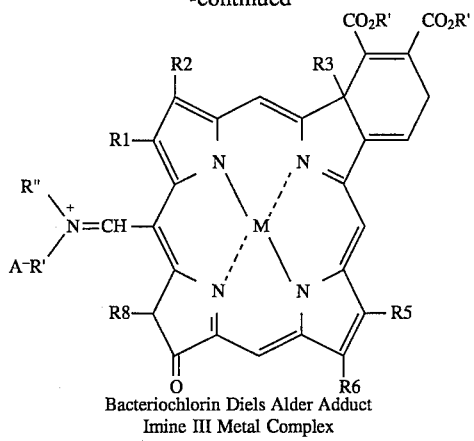

Bacteriochlorin Diels Alder Adduct
Imine III Metal Complex

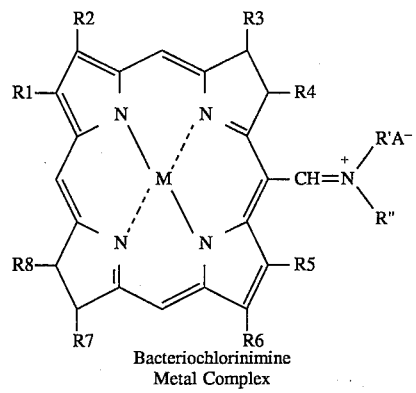

Bacteriochlorinimine
Metal Complex wherein

M comprises a metal cation that is complexed with two of the nitrogens of the benzochlorin and is Ag, Al, Ce, Co, Cr, Cu, Dy, Er, Eu, Fe, Ga, Gd, Hf, Ho, In, La, Lu, Mn, Mo, Nd, Pb, Pd, Pr, Pt, Rh, Sb, Sc, Sm, Sn, Tb, $^{99m}$Tc, Th, Ti, Tl, Tm, U, V, Y, Yb, Zn or Zr, A is a physiologically acceptable anion, R' and R" can be the same or different, and each is hydrogen or an alkyl group having from one to four carbon atoms, and each of R1 through R11 is H or CHO, an alkyl group other than t-butyl having from 1 to 4 atoms, an alkylene group having from 2 to 4 carbon atoms, a group having the formula $R_3N (R_4)_3 A$ where $R_3$ is a bivalent aliphatic hydrocarbon radical having from 1 to 4 carbon atoms, wherein any carbon to carbon bond is either a single or a double bond, and not more than one is a double bond; $R_4$ is hydrogen or an alkyl radical having 1 to 2 carbon atoms and the two $R_4$ groups can be the same or different, a group having the formula $R_3N(R_5)_3$ A where $R_3$ is a bivalent hydrocarbon radical having from 1 to 4 carbon atoms, wherein any carbon to carbon bond is either a single or a double bond, and not more than one is a double bond; A is a physiologically acceptable anion and $R_5$ is an alkyl group having from 1 to 2 carbon atoms and the three $R_5$ groups can be the same or different, a group having the formula $R_3OH$ where $R_3$ is a bivalent aliphatic hydrocarbon radical having from 1 to 4 carbon atoms, wherein any carbon to carbon bond is either a single or a double bond, and not more than one is a double bond, or $CO_2R'$, $CH_2CO_2R'$ or $CH_2CH_2CO_2R'$ where R' is H, or an alkyl group other than t-butyl having from one to four carbon atoms, with the provisos that R11 can be $SO_3H$ or a salt thereof, that, in the foregoing chlorinimines and metal complexes, either R3 or R4 can be a $CH_2$ group or O which, in either case, is bonded to the carbon of the pyrrole ring by a double bond, that, in the foregoing families of compounds which are designated Isobacteriochlorinimines I and Isobacteriochlorinimines II and their metal complexes, either R1 or R2 can be a CH2 group or O which, in either case, is bonded to the carbon of the pyrrole group ring by a double bond and, when either R1 or R2 is a $Ch_2$ or O, either R3 or R4 is also a $CH_2$ group or O which is bonded to the carbon of the pyrrole ring by and double bond, and that in the foregoing families of compounds which are designated bacteriochlorinimines and metal complexes, either R3 or R4 can be a $CH_2$ group or O which, in either case, is bonded to the carbon of the pyrrole ring by a double bond and, when either R3 or R4 is a $CH_2$ group or O, either R7 or 8 is also a $CH_2$ group or O which is bonded to the carbon of the pyrrole ring by and double bond.

\* \* \* \* \*

UNITED STATES PATENT AND TRADEMARK OFFICE
CERTIFICATE OF CORRECTION

PATENT NO. : 5,512,559
DATED : April 30, 1996
INVENTOR(S) : Dimitris Skalkos et al.

It is certified that error appears in the above-identified patent and that said Letters Patent is hereby corrected as shown below:

column 8, column 39, column 58, column 59, column 74, column 75, column 90 and column 91, Diels Alder Adduct Imine I and Diels Alder Adduct Imine II should have the following formulas:

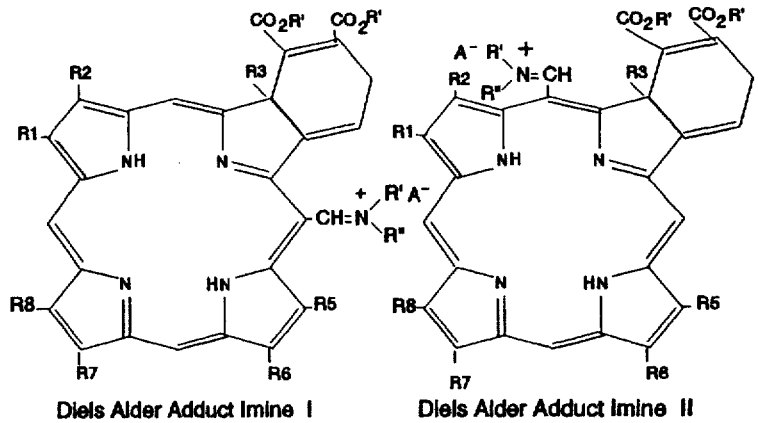

Diels Alder Adduct Imine I     Diels Alder Adduct Imine II

UNITED STATES PATENT AND TRADEMARK OFFICE
CERTIFICATE OF CORRECTION

PATENT NO. : 5,512,559
DATED : April 30, 1996
INVENTOR(S) : Dimitris Skalkos et al.

It is certified that error appears in the above-identified patent and that said Letters Patent is hereby corrected as shown below:

column 48. column 67, column 83, and column 99, Diels Alder Adduct Inime III Metal Complex and Diels Alder Adduct Imine IV Metal Complex should have the following formulas:

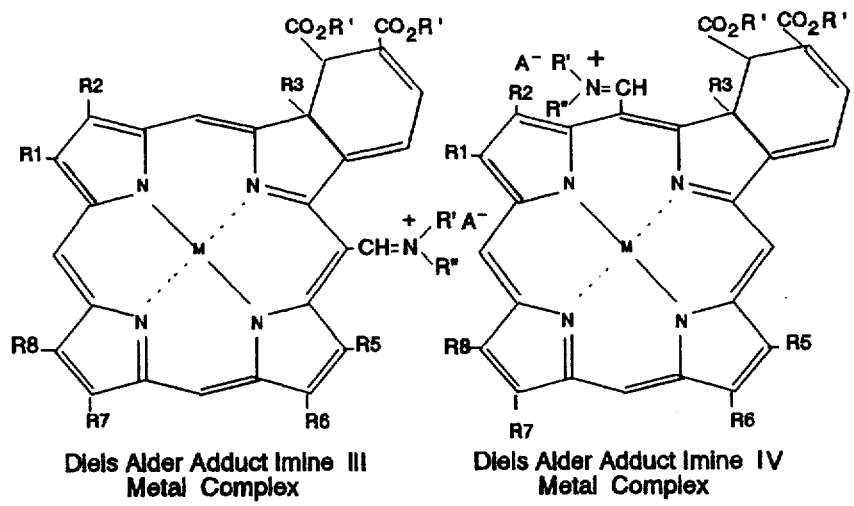

Diels Alder Adduct Imine III
Metal Complex

Diels Alder Adduct Imine IV
Metal Complex

UNITED STATES PATENT AND TRADEMARK OFFICE
CERTIFICATE OF CORRECTION

PATENT NO. : 5,512,559

DATED : April 30, 1996

INVENTOR(S) : Dimitris Skalkos et al.

It is certified that error appears in the above-identified patent and that said Letters Patent is hereby corrected as shown below:

Column 50, column 70, column 86 and column 102, the following formula and legend should be inserted after the formula and legend for Bacteriochlorin Diels Alder Adduct Imine III Metal Complex

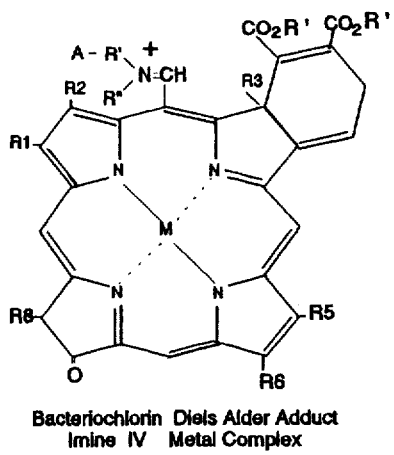

Bacteriochlorin Diels Alder Adduct
Imine IV Metal Complex

Signed and Sealed this

Tenth Day of February, 1998

*Attest:*

BRUCE LEHMAN

*Attesting Officer*     Commissioner of Patents and Trademarks